United States Patent
Dong

(10) Patent No.: US 10,517,875 B2
(45) Date of Patent: Dec. 31, 2019

(54) TARGETING DNA-PKCS AND B7-H1 TO TREAT CANCER

(71) Applicant: Mayo Foundation for Medical Education and Research, Rochester, MN (US)

(72) Inventor: Haidong Dong, Rochester, MN (US)

(73) Assignee: Mayo Foundation for Medical Engineering and Research, Rochester, MN (US)

(*) Notice: Subject to any disclaimer, the term of this patent is extended or adjusted under 35 U.S.C. 154(b) by 94 days.

(21) Appl. No.: 15/325,612

(22) PCT Filed: May 21, 2015

(86) PCT No.: PCT/US2015/032016
§ 371 (c)(1),
(2) Date: Jan. 11, 2017

(87) PCT Pub. No.: WO2016/014148
PCT Pub. Date: Jan. 28, 2016

(65) Prior Publication Data
US 2017/0173030 A1   Jun. 22, 2017

Related U.S. Application Data

(60) Provisional application No. 62/027,841, filed on Jul. 23, 2014.

(51) Int. Cl.
| | |
|---|---|
| *A61K 31/5377* | (2006.01) |
| *A61K 31/53* | (2006.01) |
| *A61K 31/00* | (2006.01) |
| *A61K 45/06* | (2006.01) |
| *A61K 31/4745* | (2006.01) |
| *A61K 31/704* | (2006.01) |
| *A61K 33/24* | (2019.01) |
| *G01N 33/574* | (2006.01) |
| *C07K 16/40* | (2006.01) |
| *C12Q 1/6886* | (2018.01) |

(52) U.S. Cl.
CPC ...... *A61K 31/5377* (2013.01); *A61K 31/4745* (2013.01); *A61K 31/704* (2013.01); *A61K 33/24* (2013.01); *A61K 45/06* (2013.01); *C07K 16/40* (2013.01); *C12Q 1/6886* (2013.01); *C12Y 207/11001* (2013.01); *G01N 33/574* (2013.01); *G01N 33/57415* (2013.01); *G01N 33/57492* (2013.01); *C07K 2317/76* (2013.01); *C12Q 2600/158* (2013.01); *G01N 2333/70532* (2013.01); *G01N 2333/70596* (2013.01); *G01N 2333/91205* (2013.01)

(58) Field of Classification Search
CPC ..... A61K 31/5377; A61K 31/53; A61K 31/00
USPC ...................................................... 424/130.1
See application file for complete search history.

(56) References Cited

U.S. PATENT DOCUMENTS

| | | |
|---|---|---|
| 3,687,808 A | 8/1972 | Merigan, Jr. et al. |
| 4,034,074 A | 7/1977 | Miles |
| 4,036,945 A | 7/1977 | Haber |
| 4,098,876 A | 7/1978 | Piasio et al. |
| 4,233,402 A | 11/1980 | Maggio et al. |
| 4,257,774 A | 3/1981 | Richardson et al. |
| 4,272,398 A | 6/1981 | Jaffe |
| 4,331,647 A | 5/1982 | Goldenberg |
| 4,376,110 A | 3/1983 | David et al. |
| 4,469,863 A | 9/1984 | Ts'o et al. |
| 4,650,764 A | 3/1987 | Temin et al. |
| 4,769,330 A | 9/1988 | Paoletti et al. |
| 4,816,567 A | 3/1989 | Cabilly et al. |
| 4,861,627 A | 8/1989 | Mathiowitz et al. |
| 4,861,719 A | 8/1989 | Miller |
| 4,925,673 A | 5/1990 | Steiner et al. |
| 4,935,496 A | 6/1990 | Kudo et al. |
| 4,946,778 A | 8/1990 | Ladner et al. |
| 4,980,289 A | 12/1990 | Temin et al. |
| 4,987,071 A | 1/1991 | Cech et al. |
| 5,013,556 A | 5/1991 | Woodle et al. |
| 5,124,263 A | 6/1992 | Temin et al. |
| 5,155,020 A | 10/1992 | Paoletti |
| 5,155,027 A | 10/1992 | Sledziewski et al. |
| 5,175,099 A | 12/1992 | Wills |
| 5,204,243 A | 4/1993 | Paoletti |
| 5,214,136 A | 5/1993 | Lin et al. |
| 5,218,105 A | 6/1993 | Cook et al. |
| 5,225,336 A | 7/1993 | Paoletti |
| 5,225,538 A | 7/1993 | Capon et al. |
| 5,235,033 A | 8/1993 | Summerton et al. |
| 5,240,846 A | 8/1993 | Collins et al. |
| 5,254,678 A | 10/1993 | Haseloff et al. |
| 5,278,056 A | 1/1994 | Bank et al. |

(Continued)

FOREIGN PATENT DOCUMENTS

| | | |
|---|---|---|
| EP | 1 074 617 | 2/2001 |
| EP | 1 537 878 | 6/2005 |

(Continued)

OTHER PUBLICATIONS

Dronca et al., "T cell Bim levels reflect responses to anti-PD-1 cancer therapy," *JCI Insight.*, 1(6): e86014, May 5, 2016, 14 pages.

(Continued)

*Primary Examiner* — Yan Xiao

(74) *Attorney, Agent, or Firm* — Fish & Richardson P.C.

(57) ABSTRACT

Materials and methods for treating potentially chemoresistant tumors (e.g., using DNA-PKcs inhibitors and anti-B7-H1 antibodies) are provided herein.

6 Claims, 17 Drawing Sheets

Specification includes a Sequence Listing.

(56) References Cited

U.S. PATENT DOCUMENTS

| | | |
|---|---|---|
| 5,284,656 A | 2/1994 | Platz et al. |
| 5,296,347 A | 3/1994 | LaMotte, III |
| 5,391,682 A | 2/1995 | Ogawa et al. |
| 5,451,569 A | 9/1995 | Wong et al. |
| 5,502,167 A | 3/1996 | Waldmann et al. |
| 5,521,288 A | 5/1996 | Linsley et al. |
| 5,530,101 A | 6/1996 | Queen et al. |
| 5,558,864 A | 9/1996 | Bendig et al. |
| 5,565,332 A | 10/1996 | Hoogenboom et al. |
| 5,567,584 A | 10/1996 | Sledziewski et al. |
| 5,585,089 A | 12/1996 | Queen et al. |
| 5,596,086 A | 1/1997 | Matteucci et al. |
| 5,639,641 A | 6/1997 | Pedersen et al. |
| 5,674,704 A | 10/1997 | Goodwin et al. |
| 5,675,848 A | 10/1997 | Kappel |
| 5,693,493 A | 12/1997 | Robinson et al. |
| 5,693,761 A | 12/1997 | Queen et al. |
| 5,693,762 A | 12/1997 | Queen et al. |
| 5,698,417 A | 12/1997 | Robinson et al. |
| 5,705,154 A | 1/1998 | Dalie et al. |
| 5,714,147 A | 2/1998 | Capon et al. |
| 5,733,743 A | 3/1998 | Johnson et al. |
| 5,750,078 A | 5/1998 | Shitara et al. |
| 5,750,375 A | 5/1998 | Sledziewski et al. |
| 5,750,666 A | 5/1998 | Caruthers et al. |
| 5,770,403 A | 6/1998 | Dalie et al. |
| 5,843,725 A | 12/1998 | Sledziewski et al. |
| 5,861,310 A | 1/1999 | Freeman et al. |
| 5,874,240 A | 2/1999 | Ni et al. |
| 5,928,893 A | 7/1999 | Kang et al. |
| 5,942,607 A | 8/1999 | Freeman et al. |
| 6,018,026 A | 1/2000 | Sledziewski et al. |
| 6,210,669 B1 | 4/2001 | Aruffo et al. |
| 6,291,212 B1 | 9/2001 | Sledziewski et al. |
| 6,291,646 B1 | 9/2001 | Sledziewski et al. |
| 6,297,008 B1 | 10/2001 | Okamoto et al. |
| 6,300,099 B1 | 10/2001 | Sledziewski et al. |
| 6,303,121 B1 | 10/2001 | Kwon |
| 6,323,323 B1 | 11/2001 | Sledziewski et al. |
| 6,355,779 B1 | 3/2002 | Goodwin et al. |
| 6,423,885 B1 | 7/2002 | Waterhouse et al. |
| 6,458,934 B1 | 10/2002 | Hong et al. |
| 6,630,575 B2 | 10/2003 | Coyle et al. |
| 6,635,750 B1 | 10/2003 | Coyle et al. |
| 6,740,493 B1 | 5/2004 | Long et al. |
| 6,743,619 B1 | 6/2004 | Tang et al. |
| 6,803,192 B1 | 10/2004 | Chen |
| 6,891,030 B2 | 5/2005 | Chen |
| 6,919,193 B2 | 7/2005 | Tang et al. |
| 6,943,150 B1 | 9/2005 | Altieri |
| 6,965,018 B2 | 11/2005 | Mikesell et al. |
| 7,029,674 B2 | 4/2006 | Carreno et al. |
| 7,030,219 B2 | 4/2006 | Pardoll et al. |
| 7,122,351 B2 | 10/2006 | Moore et al. |
| 7,279,567 B2 | 10/2007 | Mikesell et al. |
| 7,358,354 B2 | 4/2008 | Mikesell et al. |
| 7,368,531 B2 | 5/2008 | Rosen et al. |
| 7,381,794 B2 | 6/2008 | Moore et al. |
| 7,414,122 B2 | 8/2008 | Fox et al. |
| 7,432,059 B2 | 10/2008 | Freeman et al. |
| 7,432,062 B2 | 10/2008 | Coyle et al. |
| 7,432,351 B1 | 10/2008 | Chen |
| 7,449,300 B2 | 11/2008 | Chen et al. |
| 7,560,540 B2 | 7/2009 | Pardoll et al. |
| 7,563,869 B2 | 7/2009 | Honjo et al. |
| 7,582,439 B2 | 9/2009 | Cory et al. |
| 7,595,048 B2 | 9/2009 | Honjo et al. |
| 7,651,686 B2 | 1/2010 | Chen et al. |
| 7,709,214 B2 | 5/2010 | Freeman et al. |
| 7,723,479 B2 | 5/2010 | Mikesell et al. |
| 7,794,710 B2 | 9/2010 | Chen et al. |
| 7,892,540 B2 | 2/2011 | Chen et al. |
| 8,039,589 B1 | 10/2011 | Chen |
| 8,053,414 B2 | 11/2011 | Pardoll et al. |
| 8,053,558 B2 | 11/2011 | Pardoll et al. |
| 8,163,550 B2 | 4/2012 | Chen et al. |
| 8,268,635 B2 | 9/2012 | Ferrante et al. |
| 8,273,864 B2 | 9/2012 | Chen |
| 8,460,927 B2 | 6/2013 | Chen |
| 8,772,026 B2 | 7/2014 | Chen et al. |
| 8,981,063 B2 | 3/2015 | Chen |
| 9,302,005 B2 | 4/2016 | Dong et al. |
| 2002/0076409 A1 | 6/2002 | March et al. |
| 2002/0091246 A1 | 7/2002 | Pardoll et al. |
| 2002/0095024 A1 | 7/2002 | Mikesell et al. |
| 2002/0106730 A1 | 8/2002 | Coyle et al. |
| 2002/0107363 A1 | 8/2002 | Fox et al. |
| 2002/0110836 A1 | 8/2002 | Freeman et al. |
| 2002/0119121 A1 | 8/2002 | Vitiello et al. |
| 2002/0160395 A1 | 10/2002 | Altieri et al. |
| 2002/0160973 A1 | 10/2002 | Pero et al. |
| 2002/0164600 A1 | 11/2002 | Freeman et al. |
| 2002/0168719 A1 | 11/2002 | Kwon |
| 2002/0177551 A1 | 11/2002 | Terman |
| 2003/0039653 A1 | 2/2003 | Chen et al. |
| 2003/0142359 A1 | 7/2003 | Bean et al. |
| 2003/0171551 A1 | 9/2003 | Rosenblatt et al. |
| 2003/0208058 A1 | 11/2003 | Fiscella et al. |
| 2003/0223989 A1 | 12/2003 | Pluenneke |
| 2003/0232323 A1 | 12/2003 | Freeman et al. |
| 2004/0010134 A1 | 1/2004 | Rosen et al. |
| 2004/0109847 A1 | 6/2004 | Chen et al. |
| 2004/0180047 A1 | 9/2004 | Chen |
| 2004/0247563 A1 | 12/2004 | Lynch et al. |
| 2005/0013811 A1 | 1/2005 | Chen et al. |
| 2005/0228170 A1 | 10/2005 | Fox et al. |
| 2005/0260716 A1 | 11/2005 | Moore et al. |
| 2006/0034826 A1 | 2/2006 | Carreno et al. |
| 2006/0068386 A1 | 3/2006 | Slesarev et al. |
| 2006/0084794 A1 | 4/2006 | Rosen et al. |
| 2006/0110383 A1 | 5/2006 | Honjo et al. |
| 2006/0159685 A1 | 7/2006 | Mikesell et al. |
| 2006/0223088 A1 | 10/2006 | Rosen et al. |
| 2006/0276422 A1 | 12/2006 | Usman et al. |
| 2007/0037206 A1 | 2/2007 | Rosen et al. |
| 2007/0041963 A1 | 2/2007 | Rosen et al. |
| 2007/0065427 A1 | 3/2007 | Freeman et al. |
| 2007/0092504 A1 | 4/2007 | Carreno et al. |
| 2007/0099833 A1 | 5/2007 | Rosen et al. |
| 2007/0122378 A1 | 5/2007 | Freeman et al. |
| 2007/0224663 A1 | 9/2007 | Rosen et al. |
| 2007/0231344 A1 | 10/2007 | Leadbetter et al. |
| 2008/0025979 A1 | 1/2008 | Honjo et al. |
| 2008/0118511 A1 | 5/2008 | Freeman et al. |
| 2008/0226662 A1 | 9/2008 | Pardoll et al. |
| 2008/0241175 A1 | 10/2008 | Pardoll et al. |
| 2009/0042292 A1 | 2/2009 | Chen |
| 2009/0068193 A1 | 3/2009 | Chen et al. |
| 2009/0075338 A1 | 3/2009 | Moore et al. |
| 2009/0176317 A1 | 7/2009 | Kwon et al. |
| 2009/0215084 A1 | 8/2009 | Kwon et al. |
| 2009/0269783 A1 | 10/2009 | Coyle et al. |
| 2009/0304711 A1 | 12/2009 | Pardoll et al. |
| 2010/0015642 A1 | 1/2010 | Kwon et al. |
| 2010/0285039 A1 | 11/2010 | Chen |
| 2011/0020325 A1 | 1/2011 | Kwon et al. |
| 2011/0010409 A1 | 5/2011 | Strome et al. |
| 2012/0065374 A1 | 3/2012 | Pardoll et al. |
| 2012/0065385 A1 | 3/2012 | Pardoll et al. |
| 2012/0225043 A1 | 9/2012 | Chen et al. |
| 2013/0058936 A1 | 3/2013 | Bruenker et al. |
| 2013/0123566 A1 | 5/2013 | Lupold et al. |
| 2013/0251736 A1 | 9/2013 | Kwon et al. |
| 2013/0273656 A1 | 10/2013 | Hendrickson |
| 2014/0031260 A1 | 1/2014 | O'Donnel et al. |
| 2014/0242080 A1 | 8/2014 | Roche |
| 2014/0271674 A1 | 9/2014 | Dong |
| 2014/0329248 A1 | 11/2014 | Kwon et al. |
| 2014/0335541 A1 | 11/2014 | Kwon et al. |
| 2015/0111232 A1 | 4/2015 | Kwon |
| 2016/0153996 A1 | 6/2016 | Kwon et al. |
| 2016/0154000 A1 | 6/2016 | Kwon |
| 2016/0176967 A1 | 6/2016 | Dong et al. |

(56) References Cited

U.S. PATENT DOCUMENTS

| | | |
|---|---|---|
| 2016/0251437 A1 | 9/2016 | Dong et al. |
| 2017/0089918 A1 | 3/2017 | Dong |
| 2017/0363634 A1 | 12/2017 | Kwon et al. |

FOREIGN PATENT DOCUMENTS

| | | |
|---|---|---|
| WO | WO 1990/07861 | 7/1990 |
| WO | WO 1991/10741 | 7/1991 |
| WO | WO 1991/11465 | 8/1991 |
| WO | WO 1991/17271 | 11/1991 |
| WO | WO 1992/00092 | 1/1992 |
| WO | WO 1992/01047 | 1/1992 |
| WO | WO 1992/20791 | 11/1992 |
| WO | WO 1993/01222 | 1/1993 |
| WO | WO 1995/05464 | 2/1995 |
| WO | WO 1995/07707 | 3/1995 |
| WO | WO 1996/29348 | 9/1996 |
| WO | WO 1997/17613 | 5/1997 |
| WO | WO 1997/17614 | 5/1997 |
| WO | WO 1997/24447 | 7/1997 |
| WO | WO 1998/16249 | 4/1998 |
| WO | WO 1998/23635 | 6/1998 |
| WO | WO 1998/33914 | 8/1998 |
| WO | WO 1998/36096 | 8/1998 |
| WO | WO 1999/36093 | 7/1999 |
| WO | WO 1999/64597 | 12/1999 |
| WO | WO 2000/026342 | 5/2000 |
| WO | WO 2000/029445 | 5/2000 |
| WO | WO 2000/029582 | 5/2000 |
| WO | WO 2000/041508 | 7/2000 |
| WO | WO 2000/055375 | 9/2000 |
| WO | WO 2000/061612 | 10/2000 |
| WO | WO 2001/034629 | 5/2001 |
| WO | WO 2001/062905 | 8/2001 |
| WO | WO 2001/070979 | 9/2001 |
| WO | WO 2001/083750 | 11/2001 |
| WO | WO 2001/094413 | 12/2001 |
| WO | WO 2002/000692 | 1/2002 |
| WO | WO 2002/000730 | 1/2002 |
| WO | WO 2002/002587 | 1/2002 |
| WO | WO 2002/002891 | 1/2002 |
| WO | WO 2002/008279 | 1/2002 |
| WO | WO 2002/078731 | 1/2002 |
| WO | WO 2002/024891 | 3/2002 |
| WO | WO 2002/046449 | 6/2002 |
| WO | WO 2002/057453 | 7/2002 |
| WO | WO 2002/079474 | 10/2002 |
| WO | WO 2002/081731 | 10/2002 |
| WO | WO 2002/086083 | 10/2002 |
| WO | WO 2003/006632 | 1/2003 |
| WO | WO 2003/008583 | 1/2003 |
| WO | WO 2003/049755 | 6/2003 |
| WO | WO 2004/085418 | 10/2004 |
| WO | WO 2006/042237 | 4/2006 |
| WO | WO 2006/050172 | 5/2006 |
| WO | WO 2006/133396 | 12/2006 |
| WO | WO 2008/037080 | 4/2008 |
| WO | WO 2008/083174 | 7/2008 |
| WO | WO 2009/023566 | 2/2009 |
| WO | WO 2009/029342 | 3/2009 |
| WO | WO 2009/114110 | 9/2009 |
| WO | WO 2010/027423 | 3/2010 |
| WO | WO 2010/027827 | 3/2010 |
| WO | WO 2010/027828 | 3/2010 |
| WO | WO 2010/098788 | 9/2010 |
| WO | WO 2011/066342 | 6/2011 |
| WO | WO 2011/066389 | 6/2011 |
| WO | WO 2013/003112 | 2/2013 |
| WO | WO 2013/019906 | 2/2013 |
| WO | WO 2013/090552 | 6/2013 |
| WO | WO 2013/132044 | 9/2013 |
| WO | WO 2015/050663 | 4/2015 |
| WO | WO 2015/179654 | 11/2015 |

OTHER PUBLICATIONS

Dronca et al., "BCL-2-interacting mediator of cell death (Bim) is a novel biomarker for response to anti-PD-1 therapy in patients with advanced melanoma," Immunotherapy, 8(12)1351-1353, Dec. 1, 2016.

European Office Action in Application No. EP 14850189.3, dated Oct. 26, 2017, 11 pages.

Extended European Search Report in International Application No. 15825450.8, dated Feb. 21, 2018, 9 pages.

Academic Press Dictionary of Science and Technology (definition for the term "polyclonal"; Oxford: Elsevier Science & Technology (1996); retrieved Oct. 22, 2008, from http://www.credoreference.com/entry/3144515/.

Acsadi et al., "Direct gene transfer and expression into rat heart in vivo," New Biol., 3(1):71-81, Jan. 1991.

Adachi et al., "Enhanced and accelerated lymphoproliferation in Fas-null mice.," Proc Natl Acad Sci U S A., 93(5):2131-2136, Mar. 5, 1996.

Adachi et al., "Aberrant transcription caused by the insertion of an early transposable element in an intron of the Fas antigen gene of lpr mice," Proc Natl Acad Sci U S A., 90(5):1756-1760, Mar. 1, 1993.

Agata et al., "Expression of the PD-1 antigen on the surface of stimulated mouse T and B lymphocytes," Int Immunol., 8(5):765-772, May 1996.

Ahmadzadeh et al., "Tumor antigen-specific CD8 T cells infiltrating the tumor express high levels of PD-1 and are functionally impaired," Blood, 114(8):1537-1544, Epub May 7, 2009.

Ahonen et al., "Combined TLR and CD40 triggering induces potent CD8+ T cell expansion with variable dependence on type I IFN," J Exp Med., 199(6):775-784, Epub Mar. 8, 2004.

Alderson et al., "Molecular and biological characterization of human 4-1BB and its ligand," Eur J Immunol., 24(9):2219-2227, Sep. 1994.

Aldovini et al., "Humoral and cell-mediated immune responses to live recombinant BCG-HIV vaccines," Nature, 351(6326):479-482, Jun. 6, 1991.

Allie et al., "Programmed death 1 regulates development of central memory CD8 T cells after acute viral infection," J Immunol., 186(11):6280-6286, Epub Apr. 27, 2011.

Ambrosini et al., "A novel anti-apoptosis gene, survivin, expressed in cancer and lymphoma," Nat Med., 3(8):917-921, Aug. 1997.

Anderson, "Human gene therapy," Science, 256(5058):808-813, May 8, 1992.

Andorsky et al., "Programmed death ligand 1 is expressed by non-hodgkin lymphomas and inhibits the activity of tumor-associated T cells," Clin Cancer Res., 17(13):4232-4244, Epub May 3, 2011.

Anikeeva et al., "Distinct role of lymphocyte function-associated antigen-1 in mediating effective cytolytic activity by cytotoxic T lymphocytes," Proc Natl Acad Sci U S A., 102(18):6437-6442, Epub Apr. 25, 2005.

Ansari et al., "The programmed death-1 (PD-1) pathway regulates autoimmune diabetes in nonobese diabetic (NOD) mice," J Exp Med., 198(1):63-69, Jul. 7, 2003.

Anukam et al., "Augmentation of antimicrobial metronidazole therapy of bacterial vaginosis with oral probiotic Lactobacillus rhamnosus GR-1 and Lactobacillus reuteri RC-14: randomized, double-blind, placebo controlled trial," Microbes Infect., 8(6):1450-1454, Epub Mar. 29, 2006.

Attwood et al., "Genomics. The Babel of bioinformatics," Science, 290(5491):471-473, Oct. 20, 2000.

Azuma et al., "B7-H1 is a ubiquitous antiapoptotic receptor on cancer cells," Blood., 111(7):3635-3643, Epub Jan. 25, 2008.

Baitsch et al., "Exhaustion of tumor-specific CD8+T cells in metastases from melanoma patients," J Clin Invest., 121(6):2350-2360, Epub May 9, 2011.

Bajorath et al., "Molecular modeling of CD28 and three-dimensional analysis of residue conservation in the CD28/CD152 family," J Mol Graph Model., 15(2):135-9, 108-111, Apr. 1997.

(56) References Cited

OTHER PUBLICATIONS

Baldrick, "Pharmaceutical excipient development: the need for preclinical guidance," *Regul Toxicol Pharmacol.*, 32(2):210-218, Oct. 2000.
Banáth et al., "Residual gammaH2AX foci as an indication of lethal DNA lesions," *BMC Cancer.*, 10:4, Jan. 5, 2010.
Barber et al., "Restoring function in exhausted CD8 T cells during chronic viral infection," Nature, 439(7077):682-687, Epub Dec. 28, 2005.
BD PharmingenTM Technical Data Sheet, "Purified Rat Anti-Mouse Ly-6G (Gr-1) Monoclonal Antibody for Immunohistochemistry (IHC)" 1 page, 2003.
Benita et al., "Characterization of drug-loaded poly(d,l-lactide) microspheres," *J Pharm Sci.*, 73(12):1721-1724, Dec. 1984.
Benlalam et al., "Comprehensive analysis of the frequency of recognition of melanoma-associated antigen (MAA) by CD8 melanoma infiltrating lymphocytes (TIL) implications for immunotherapy," *Eur J Immunol.*, 31(7):2007-2015, Jul. 31, 2001.
Bennardo et al., "Alternative-NHEJ is a mechanistically distinct pathway of mammalian chromosome break repair," *PLoS Genet*, 4(6):e1000110, Jun. 27, 2008.
Berman et al., "The Protein Data Bank," *Nucleic Acids Res.*, 28(1):235-242, Jan. 1, 2000.
Berrien-Elliott et al., "Durable adoptive immunotherapy for leukemia produced by manipulation of multiple regulatory pathways of CD8+ T-cell tolerance," *Cancer Res.*, 73(2):605-616, Jan. 15, 2013.
Berthon et al., "In acute myeloid leukemia, B7-H1 (PD-L1) protection of blasts from cytotoxic T cells is induced by TLR ligands and interferon-gamma and can be reversed using MEK inhibitors," *Cancer Immunol Immunother.*, 59(12): 1839-1849, Epub Sep. 4, 2010.
Betts et al., "Sensitive and viable identification of antigen-specific CD8+ T cells by a flow cytometry assay for degranulation," *J Immunol Methods.*, 281(1-2):65-78, Oct. 1, 2003.
Bird et al., "Single-chain antigen-binding proteins," *Science*, 242(4877):423-426, Oct. 21, 1988.
Blank et al., "Blockade of PD-L1 (B7-H1) augments human tumor-specific T cell responses in vitro," *Int J Cancer*, 119(2):317-327, Jul. 15, 2006.
Blank et al., "Interaction of PD-L1 on tumor cells with PD-1 on tumor-specific T cells as a mechanism of immune evasion: implications for tumor immunotherapy," *Cancer Immunol Immunother.*, 54(4):307-3 14, Epub Dec. 15, 2004.
Blank et al., "PD-L1/B7H-1 inhibits the effector phase of tumor rejection by T cell receptor (TCR) transgenic CD8+ T cells," Cancer Res., 64(3):1140-1145, Feb. 1, 2004.
Blazar et al., "Infusion of anti-B7.1 (CD80) and anti-B7.2 (CD86) monoclonal antibodies inhibits mutine graft-versus-host disease lethality in part via direct effects on CD4+ and CD8+ T cells," J Immunol, 157(8):3250-3259, Oct. 15, 1996.
Block, "Medicated Applications," Remington's Pharmaceutical Sciences, 18th edition, Mack Publishing Company, Easton, PA, Chpt 87, pp. 1596-1614, 1990.
Bodine, "mTOR signaling and the molecular adaptation to resistance exercise," Med Sci Sports Exerc., 38(11):1950-1957, Nov. 2006.
Boggio et al., "Interleukin 12-mediated prevention of spontaneous mammary adenocarcinomas in two lines of Her-2/neu transgenic mice," J Exp Med., 188(3):589-596, Aug. 3, 1998.
Boise et al., "CD28 costimulation can promote T cell survival by enhancing the expression of Bcl-XL," *Immunity*, 3(1):87-98, Jul. 1995.
Boletta et al., "High efficient non-viral gene delivery to the rat kidney by novel polycationic vectors," *J Am Soc Nephrol.*, 7(9):1728, abstr A2409, Sep. 1, 1996.
Bona et al., "Immune response: Idiotype anti-idiotype network," *CRC Crit Rev Immunol.*, 33-81, Mar. 1981.
Bonfoco et al., "Inducible nonlymphoid expression of Fas ligand is responsible for superantigen-induced peripheral deletion of T cells," *Immunity*, 9(5):711-720, Nov. 1998.

Bonifaz et al., "Efficient targeting of protein antigen to the dendritic cell receptor DEC-205 in the steady state leads to antigen presentation on major histocompatibility complex class I products and peripheral CD8+ T cell tolerance," *J Exp Med.*, 196(12):1627-1638, Dec. 16, 2002.
Bonifaz et al., "In vivo targeting of antigens to maturing dendritic cells via the DEC-205 receptor improves T cell vaccination," *J Exp Med.*, 199(6):815-824, Mar. 15, 2004.
Bonni et al., "Cell survival promoted by the Ras-MAPK signaling pathway by transcription-dependent and -independent mechanisms," *Science*, 286(5443):1358-1362, Nov. 12, 1999.
Boon et al., "Human T cell responses against melanoma," *Annu Rev Immunol.*, 24:175-208, 2006.
Borson et al., "Brain-infiltrating cytolytic T lymphocytes specific for Theiler's virus recognize H2Db molecules complexed with a viral VP2 peptide lacking a consensus anchor residue," *J Virol.*, 71(7):5244-5250, Jul. 1997.
Bouillet and O'Reilly, "CD95, BIM and T cell homeostasis," *Nat Rev Immunol.*, 9(7):514-519, Jul. 2009.
Bowie et al, "Deciphering the message in protein sequences: tolerance to amino acid substitutions," *Science*, 247(4948):1306-1310, Mar. 16, 1990.
Brahmer et al., "Safety and activity of anti-PD-L1 antibody in patients with advanced cancer," *N Engl J Med.*, 366(26):2455-2465, Epub Jun. 2, 2012.
Braquet et al., "Effect of endothelin-1 on blood pressure and bronchopulmonary system of the guinea pig," *J Cardiovasc Pharmacol.*, 13 Suppl 5:S143-6; discussion S150, 1989.
Brinkmann et al., "FTY720: altered lymphocyte traffic results in allograft protection," Transplantation., 72(5):764-769, Sep. 15, 2001.
Britton et al., "Leprosy," *Lancet*, 363(9416):1209-1219, Apr. 10, 2004.
Brooks, "Translational genomics: the challenge of developing cancer biomarkers," *Genome Res.*, 22(2):183-187, Feb. 2012.
Brown et al., "Blockade of programmed death-1 ligands on dendritic cells enhances T cell activation and cytokine production.," *J Immunol.*, 170(3):1257-1266, Feb. 1, 2003.
Brozovic et al., "Activation of mitogen-activated protein kinases by cisplatin and their role in cisplatin-resistance," *Cancer Lett.*, 251(1):1-16. Epub Nov. 27, 2006.
Bubenik, "Genetically engineered dendritic cell-based cancer vaccines (Review)," *Int J Oncol.*, 18(3):475-478, Mar. 2001.
Burmer et al, "Frequency and spectrum of c-Ki-ras mutations in human sporadic colon carcinoma, carcinomas arising in ulcerative colitis, and pancreatic adenocarcinoma," *Environ Health Perspect*, 93:27-31, Jun. 1991.
Buskens et al, "Adenocarcinomas of the gastro-esophageal junction: A comparative study of the gastric cardia and the esophagus with respect to cyclooxygenase-2 expression," Digestive Disease Week Abstracts and Itinerary Planner, 2003, abstract No:850.
Butte et al., "Interaction of human PD-L1 and B7-1," *Mol Immunol.*, 45(13):3567-3572, Epub Jun. 27, 2008.
Butte et al., "PD-L1 interacts specifically with B7-1 to inhibit T cell proliferation," *Immunity*, 27:111-122, 2007.
Cairns et al., "Immortalization of multipotent growth-factor dependent hemopoietic progenitors from mice transgenic for GATA-1 driven SV40 tsA58 gene," *EMBO J.*, 13(19):4577-4586, Oct. 3, 1994.
Cannons et al., "4-1BB ligand induces cell division, sustains survival, and enhances effector function of CD4 and CD8 T cells with similar efficacy," *J Immunol.*, 167(3):1313-1324, Aug. 1, 2001.
Cao et al., "B7-H1 overexpression regulates epithelial-mesenchymal transition and accelerates carcinogenesis in skin," *Cancer Res.*, 71(4):1235-1243, Epub Dec. 15, 2010.
Carreno et al., "The B7 family of ligands and its receptors: new pathways for costimulation and inhibition of immune responses," *Annu Rev Immunol.*, 20:29-53, Epub Oct. 4, 2001.
Carter et al., "PD-1:PD-L inhibitory pathway affects both CD4(+) and CD8(+) T cells and is overcome by IL-2," *Eur J Immunol.*, 32(3):634-643, Mar. 2002.
Carter et al., "Humanization of an anti-p185HER2 antibody for human cancer therapy," *Proc Natl Acad Sci U S A.*, 89(10):4285-4289, May 15, 1992.

(56) References Cited

OTHER PUBLICATIONS

Chakrabarti et al., "Vaccinia virus expression vector: coexpression of beta-galactosidase provides visual screening of recombinant virus plaques," *Mol Cell Biol.*, 5(12):3403-3409, Dec. 1985.

Chambers et al., "Co-stimulation in T cell responses," *Curr Opin Immunol.*, 9(3):396-404, Jun. 1997.

Chan et al., "Autophosphorylation of the DNA-dependent protein kinase catalytic subunit is required for rejoining of DNA double-strand breaks," *Genes Dev.*, 16(18):2333-2338, Sep. 15, 2002.

Chapoval et al., "B7-H3: A costimulatory molecule for T cell activation and IFN-γ production," *Nat Immunol.*, 2(3):269-274, Mar. 2001.

Charman, "Lipids, lipophilic drugs, and oral drug delivery-some emerging concepts," *J. Pharm. Sci.*, 89(8):967-978, Aug. 2000.

Chaurand et al., "Peptide and Protein Identification by Matrix-Assisted Laser Desorption Ionization (MALDI) and MALDI-Post-Source Decay Time-of-Flight Mass Spectrometry," *J Am Soc Mass Spectrom.*, 10(2):91-103, Feb. 1999.

Chen et al., "CD44-deficient mice exhibit enhanced hepatitis after concanavalin A injection: evidence for involvement of CD44 in activation-induced cell death," *J Immunol*, 166(10):5889-5897, May 1, 2001.

Chen et al., "Costimulation of antitumor immunity by the B7 counterreceptor of the T lymphocyte molecules CD28 and CTLA-4," *Cell*, 71(7):1093-1102, Dec. 24, 1992.

Chen et al., "Tumor immunogenicity determines the effect of co-stimulation by B7 on T-cell mediated tumor immunity," *J Exp Med.*, 179(2):523-532, Feb. 1, 1994.

Chen, "Co-inhibitory molecules of the B7-CD28 family in the control of T-cell immunity," *Nat Rev Immunol.*, 4(5):336-347, May 2004.

Cheville et al., "Comparisons of outcome and prognostic features among histologic subtypes of renal cell carcinoma," *Am J Surg Pathol.*, 27(5):612-624, May 2003.

Choi et al., "Genomic Organization and expression Analysis of B7-H4, an Immune Inhibitory Molecule of the B7 Family," *J Immunol.*, 171(9):4650-4654, Nov. 1, 2003.

Cogoni et al. "Transgene silencing of the al-1 gene in vegetative cells of Neurospora is mediated by a cytoplasmic effector and does not depend on DNA-DNA interactions or DNA methylation," *EMBO J.*, 15(12):3153-3163, Jun. 17, 1996.

Cogoni et al., "Gene silencing in Neurospora crassa requires a protein homologous to RNA-dependent RNA polymerase," *Nature*, 399(6732):166-169, May 13, 1999.

Cohen et al., "Lpr and gld: Single Gene Models of Systemic Autoimmunity and Lymphoproliferative Disease," *Annu Rev Immunol.*, 9:243-269, 1991.

Cole et al., "The EBV-hybridoma technique and its application to human lung cancer," *Monoclonal Antibodies and Cancer Therapy*, 27:77-96, Jan.-Feb. 1985.

Collins et al., "The B7 family of immune-regulatory ligands," *Genome Biol.*, 6(6):223, 7 pages, Epub May 31, 2005.

Collis et al., "The life and death of DNA-PK," *Oncogene.*, 24(6):949-961, Feb. 3, 2005.

Conacci-Sorrell et al., "Autoregulation of E-cadherin expression by cadherin-cadherin interactions: the roles of beta-catenin signaling, Slug, and MAPK," *J Cell Biol.*, 163(4):847-857, Epub Nov. 17, 2003.

Cone et al., "High-efficiency gene transfer into mammalian cells: generation of helper-free recombinant retrovirus with broad mammalian host range," *Proc Natl Acad Sci U S A.*, 81(20):6349-6353, Oct. 1984.

Connolly, "Analytical molecular surface 1983 calculation," *J Appl Crystallogr.*, 16(5):548-558, Oct. 1, 1983.

Corpet, "Multiple sequence alignment with hierarchical clustering," *Nucleic Acids Res.*, 16(22):10881-10890, Nov. 25, 1988.

Cote et al., "Generation of human monoclonal antibodies reactive with cellular antigens," *Proc Natl Acad Sci U S A.*, 80(7):2026-2030, Apr. 1983.

Coyle et al., "The expanding B7 superfamily: increasing complexity in costimulatory signals regulating T cell function," *Nat Immunol.*, 2(3):203-209, Mar. 2001.

Crispe et al., "The liver as a site of T-cell apoptosis: graveyard, or killing field?" *Immunol Rev.*, 174:47-62, Apr. 2000.

Crispe, "Hepatic T cells and liver tolerance," *Nat Rev Immunol.*, 3(1):51-62, Jan. 2003.

Cristiano et al., "Molecular conjugates: a targeted gene delivery vector for molecular medicine," *J Mol Med (Berl).*, 73(10):479-486, Oct. 1995.

Crystal, "Gene therapy strategies for pulmonary disease" *Am J Med.*, 92(suppl 6A):44S-52S, Jun. 22, 1992.

Curiel et al., "Blockade of B7-H1 improves myeloid dendritic cell-mediated antitumor immunity," *Nat Med.*, 9(5):562-567, Epub Apr. 21, 2003.

Dao et al., "Involvement of CD1 in peripheral deletion of T lymphocytes is independent of NK T cells," *J Immunol.*, 166(5):3090-3097, Mar. 1, 2001.

Database EM-MUS [Online]EMBL; Accession No. AF142780.1 (version 1), Jun. 1, 1999, 2 pages.

Datta et al., "Akt phosphorylation of BAD couples survival signals to the cell-intrinsic death machinery," *Cell.*, 91(2):231-241, Oct. 17, 1997.

Davidson et al., "Phenotypic, functional, and molecular genetic comparisons of the abnormal lymphoid cells of C3H-lpr/lpr and C3H-gld/gld mice," *J Immunol.*, 136(11):4075-4084, Jun. 1, 1986.

Davidson et al., "Small Molecules, Inhibitors of DNA-PK, Targeting DNA Repair, and Beyond," *Front Pharmacol*, vol. 4, Article 5, pp. 1-7, Jan. 31, 2013.

de StGroth et al., "Production of monoclonal antibodies: strategy and tactics," *J Immunol Methods*, 35(1-2):1-21, 1980.

Debs et al., "Lung-specific delivery of cytokines induces sustained pulmonary and systemic immunomodulation in rats," *J Immunol.*, 140(10):3482-3488, May 15, 1988.

del Peso et al., "Interleukin-3-induced phosphorylation of BAD through the protein kinase Akt," *Science*, 278(5338):687-689, Oct. 24, 1997.

Dheda et al., "Lung remodeling in tuberculosis," *J Infect Dis.*, 192(7):1201-1209, Epub Aug. 29, 2005.

Diehl et al., "In vivo triggering through 4-1BB enables Th-independent priming of CTL in the presence of an intact CD28 costimulatmy pathway," *J Immunol.*, 168(8):3755-3762, Apr. 15, 2002.

Ding et al., "Release of reactive nitrogen intermediates and reactive oxygen intermediates from mouse peritoneal macrophages. Comparison of activating cytokines and evidence for independent production," *J Immunol.*, 141(7):2407-2412, Oct. 1, 1988.

Dini, "Recognizing death: liver phagocytosis of apoptotic cells," *Eur J Histochem.*, 44(3):217-227, 2000.

Doering et al., "Network analysis reveals centrally connected genes and pathways involved in CD8+ T cell exhaustion versus memory," *Immunity*, 37(6):1130-1144, Epub Nov. 15, 2012.

Dong et al., "B7-H1 determines accumulation and deletion of intrahepatic CD8(+) T lymphocytes," *Immunity.*, 20(3):327-336, Mar. 2004.

Dong et al., "B7-H1 pathway and its role in the evasion of tumor immunity" *J Mol Med (Berl).*, 81(5):281-287, Epub Apr. 30, 2003.

Dong et al., "B7-H1, a third member of the B7 family, co-stimulates T-cell proliferation and interleukin-10 secretion," *Nat Med.*, 5(12):1365-1369, Dec. 1999.

Dong et al., "Immune regulation by novel costimulatory molecules," *Immunol Res.*, 28(1):39-48, 2003.

Dong et al., "Immunoregulatory role of B7-H1 in chronicity of inflammatory responses," *Cell Mol Immunol.*, 3(3):179-187, Jun. 2006.

Dong et al., "Tumor-associated B7-H1 promotes T-cell apoptosis: a potential mechanism of immune evasion," *Nat Med.*, 8(8):793-800, Epub Jun. 24, 2002.

Dragoi et al., "DNA-PKcs, but not TLR9, is required for activation of Akt by CpG-DNA," *EMBO J.*, 24(4):779-789, Epub Jan. 27, 2005.

(56) References Cited

OTHER PUBLICATIONS

Dronca et al., "Soluble PD-L1 (sPD-L1) is associated with decreased survival in metastatic melanoma," Society for Melanoma Research 2015 Congress, San Francisco, CA, Nov. 18-21, 2015 [abstract].
Dudler et al., "Gene transfer of programmed death Ligand-1.Ig prolongs cardiac allograft survival," *Transplantation*, 82(12):1733-1737, Dec. 27, 2006.
Dunussi-Joannopoulos et al., "Gene therapy with B7.1 and GM-CSF vaccines in a murine AML model," *J Pediatr Hematol Oncol.*, 19(6):536-540, Nov-Dec. 1997.
Duraiswamy et al., "Replenish the source within Rescuing tumor-infiltrating lymphocytes by double checkpoint blockade," Oncol., 2:10, e25912, Oct. 2013.
Ehl et al., "Different susceptibility of cytotoxic T cells to CD95 (Fas/Apo-1) ligand-mediated cell death after activation in vitro versus in vivo," *J Immunol.*, 156(7):2357-2360, Apr. 1, 1996.
Elliott et al., "Mitoxantrone in combination with an inhibitor of DNA-dependent protein kinase: a potential therapy for high risk B-cell chronic lymphocytic leukaemia," *Br J Haematol*, 152(1):61-71, Epub Nov. 18, 2010.
EMBL-EBI Accession No. AF 142780.2 "Mus musculus butyrophilin-like protein (Btdc) mRNA, complete cds," created Jun. 1, 1999, 2 pages.
EMBL-EBI Accession No. Q9WUL5, "Programmed cell death 1 ligand 2," Nov. 1, 1999, 5 pages.
Engh et al., "Accurate bond and angle parameters for X-ray protein structure refinement," *Acta Cryst.*, A47(4):392-400, Jul. 1, 1991.
European Search Report for Application No. EP 02802551, 3 pages, completed Oct 14, 2004.
European Search Report for Application No. EP 14850189.3, dated Feb. 27, 2017, 5 pages.
Falkner et al., "pUV I: a new vaccinia virus insertion and expression vector," *Nucleic Acids Res.*, 15(17):7192, Sep. 11, 1987.
Farley et al., "p38 mitogen-activated protein kinase mediates the Fas-induced mitochondrial death pathway in CD8+ T cells," *Mol Cell Biol*, 26(6):2118-2129, Mar. 2006.
Fechteler et al., "Prediction of protein three-dimensional structures in insertion and deletion regions: a procedure for searching data bases of representative protein fragments using geometric scoring criteria," *J Mol Biol.*, 253(1):114-131, Oct. 13, 1995.
Feng et al., "Identification of a PKB/Akt hydrophobic motif Ser-473 kinase as DNA-dependent protein kinase," *J Biol Chem.*, 279(39):41189-41196, Epub Jul. 15, 2004.
Figlin et al., "Treatment of metastatic renal cell carcinoma with nephrectomy, interleukin-2 and cytokine-primed or CD8(+) selected tumor infiltrating lymphocytes from primary tumor," *J. Urol.*, 158(3 Pt 1):740-745, Sep. 1997.
Finck et al., "Treatment of Murine Lupus with CTLA4Ig," *Science*, 265(5176):1225-1227, Aug. 26, 1994..
Fire et al., "Potent and specific genetic interference by double-stranded RNA in Caenorhabditis elegans," *Nature*, 391(6669):806-811, Feb. 19, 1998.
Fleming et al., Selective expression of Ly-6G on myeloid lineage cells in mouse bone marrow. RB6-8C5 mAb to granulocyte-differentiation antigen (Gr-1) detects members of the Ly-6 family, *J Immunol.*, 151(5):2399-2408, Sep. 1, 1993.
Foell et al., "CD137 costimulatory T cell receptor engagement reverses acute disease in lupus-prone NZB x NZW F1 mice," *J Clin Invest.*, 111(10):1505-1518, May 2003.
Foell et al., "CD137-Mediated T Cell Co-Stimulation Terminates Existing Autoimmune Disease in SLE-Prone NZB/NZW F1 Mice," *Ann N Y Acad Sci.*, 987:230-235, Apr. 2003.
Fortugno et al., "Survivin exists in immunochemically distinct subcellular pools and is involved in spindle microtubule function," *J Cell Sci.*, 115(Pt 3):575-585, Feb. 1, 2002.
Frank et al., "An outcome prediction model for patients with clear cell renal cell carcinoma treated with radical nephrectomy based on tumor stage, size, grade and necrosis: the SSIGN score," *J Urol.*, 168(6):2395-2400, Dec. 2002.

Freeman et al., "B7, a new member of the Ig superfamily with unique expression on activated and neoplastic B cells," *J Immunol.*, 143(8):2714-2722, Oct. 15, 1989.
Freeman et al., "Cloning of B7-2: a CTLA-4 counter-receptor that co stimulates human T cell proliferation," *Science*, 262(5135):909-911, Nov. 5, 1993.
Freeman et al., "Engagement of the PD-1 Immunolnhibitory receptor by a novel B7 family member leads to negative regulation of lymphocyte activation," *J Exp Med.*, 192(7): 1027-1034, Oct. 2, 2000.
Freeman et al., "Structure, expression, and T cell proliferation costimulatory activity of the murine homologue of the human B lymphocyte activation antigen B7," *J Exp Med.*, 174(3):625-631, Sep. 1, 1991.
Friedmann et al., "Interaction of the epidermal growth factor receptor and the DNA-dependent protein kinase pathway following gefitinib treatment," *Mol Cancer Ther.*, 5(2):209-218, Feb. 2006.
Frigola et al., "Identification of a soluble form of B7-H1 that retains immunosuppressive activity and is associated with aggressive renal cell carcinoma," *Clin Cancer Res.*, 17(7): 1915-1923, Apr. 1, 2011.
Fuerst et al., "Transfer of the inducible lac repressor/operator system from *Escherichia coli* to a vaccinia expression vector," *Proc Natl Acad Sci U S A.*, 86(8):2549-2553, Apr. 1989.
Fyfe et al., "Results of treatment of 255 patients with metastatic renal cell carcinoma who received high-dose recombinant interleukin-2 therapy," *J Clin Oncol.*, 13(3):688-696, Mar. 1995.
GenBank Accession No. AAC51660 "apoptosis inhibitor survivin [*Homo sapiens*]," Sep. 2, 2004, 2 pages.
GenBank Accession No. AAP37283, "immune costimulatory protein B7-H4 [*Homo sapiens*]," Jun. 1, 2003, 1 page.
GenBank Accession No. AK001872.1, "*Homo sapiens* cDNA FLJ11010 fis, clone PLACE1003145," Feb. 22, 2000, 2 pages.
GenBank Accession No. AL162253, "Human DNA sequence from clone RP11-574F11 on chromosome 9 contains the gene for B7-H1 protein (PD-L1), the gene for programmed death ligand 2 (PDL2) (PDCD1L2) and a novel gene, complete seguence" Feb. 24, 2008, 35 pages.
GenBank Accession No. AY280972, "*Homo sapiens* immune costimulatory protein B7-H4 mRNA, complete cds," Jun. 1, 2003, 1 page.
GenBank Accession No. NM_005191.3 (GI No. 113722122), "*Homo sapiens* CD80 molecule (CD80), mRNA," Jun. 15, 2013, 5 pages.
GenBank Accession No. NP_005182.1 (GI No. 4885123), "T-lymphocyte activation antigen CD80 precursor [*Homo sapiens*]," Jun. 15, 2013, 3 pages.
GenBank Accession No. U75285 "*Homo sapiens* apoptosis inhibitor survivin gene, complete cds," Sep. 2, 2004, 5 pages.
GenBank® Accession No. AAF25807 (GI No. 6708119), "B7-H1 [*Homo sapiens*]," Jan. 18, 2000, 2 pages.
GenBank® Accession No. AAH74740.1, GI No. 49902307, "Programmed cell death 1 [*Homo sapiens*]," Jul. 15, 2006, 2 pages.
GenBank® Accession No. AAX29153.1, GI No. 60652917, "integrin alpha L, partial [synthetic construct]," Mar. 29, 2005, 2 pages.
GenBank® Accession No. AF177937 (GI No. 6708118), "*Homo sapiens* B7-H1 mRNA, complete cds," Jan. 18, 2000, 1 page.
GenBank® Accession No. BC008777.2, GI No. 33870544, "*Homo sapiens* integrin, alpha L (antigen CD11A (p180), lymphocyte function-associated antigen 1; alpha polypeptide), mRNA (cDNA clone MGC:1714 IMAGE:3142951), complete cds," Jul. 28, 2005, 4 pages.
GenBank® Accession No. BC074740.2, GI No. 50960296, "*Homo sapiens* programmed cell death 1, mRNA (cDNA clone MGC:103817 IMAGE:30915198), complete cds," Jul. 15, 2006, 3 pages.
Gerdes et al. "Cell cycle analysis of a cell proliferation-associated human nuclear antigen defined by the monoclonal antibody Ki-67," *J Immunol*, 133(4):1710-1715, Oct. 1984.
Gerstmayer et al., "Costimulation of T cell proliferation by a chimeric B7-2 antibody fusion protein specifically targeted to cells expressing the erbB2 proto-oncogene," *J Immunol*, 158(10):4584-4590, May 15, 1997.
Gerstmayer et al., "Costimulation of T-cell proliferation by a chimeric B7 antibody fusion protein," *Cancer Immunol Innunother.*, 45(3-4):156-158, Nov.-Dec. 1997.

(56) References Cited

OTHER PUBLICATIONS

Gevaert et al., "Protein identification based on matrix assisted laser desorption/ionization-post source decay-mass spectrometry," *Electrophoresis*, 22(9):1645-1651, May 2001.

Ghebeh et al., "Doxorubicin downregulates cell surface B7-H1 expression and upregulates its nuclear expression in breast cancer cells: role of B7-H1 as an anti-apoptotic molecule," *Breast Cancer Res.*, 12(4):R48, Epub Jul. 13, 2010.

Ghebeh et al., "The B7-H1 (PD-L1) T lymphocyte-inhibitory molecule is expressed in breast cancer patients with infiltrating ductal carcinoma: correlation with important high risk prognostic factors," *Neoplasia*, 8(3):190-198, Mar. 2006.

Gibbons et al., "B7-H1 limits the entry of effector CD8(+) T cells to the memory pool by upregulating Bim," Oncoimmunology, 1(7):1061-1073, Oct. 1, 2012.

Gillings et al., "Apoptosis and autophagy: BIM as a mediator of tumour cell death in response to oncogene-targeted therapeutics," *FEBS J.*, 276(21):6050-6062, Epub Sep. 29, 2009.

Gimmi et al., "B-cell surface antigen B7 provides a costimulatory signal that induces T cells to proliferate and secrete interleukin 2," *Proc Natl Acad Sci U S A.*, 88(9):3671-3675, May 1, 1991.

Goodwin et al., "Molecular cloning and expression of the type 1 and type 2 murine receptors for tumor necrosis factor," *Mol Cell Biol.*, 11(6):3020-3026, Jun. 1991.

Goodwin et al., "Molecular cloning of a ligand for the inducible T cell gene 4-1BB: a member of an emerging family of cytokines with homology to tumor necrosis factor," *Eur J Immunol.*, 23(10):2631-2641, Oct. 1993.

Green et al., "Activation-induced cell death in T cells," *Immunol Rev.*, 193:70-81, Jun. 2003.

Green et al., "Antigen-specific human monoclonal antibodies from mice engineered with human Ig heavy and light chain YACs," *Nat Genet.*, 7(1):13-21, May 1994.

Greenwald et al., "The B7 family revisited," *Annu Rev Immunol.*, 23:515-548, 2005.

Grivennikov et al. "Immunity, inflammation, and cancer," *Cell.*, 140(6):883-899, Mar. 19, 2010.

Guatelli et al., "Isothermal, in vitro amplification of nucleic acids by a multi enzyme reaction modeled after retroviral replication," *Proc Natl Acad Sci U S A.*, 87(5):1874-1878, Mar. 1990.

Guinn et al., "4-1BBL cooperates with B7-1 and B7-2 in converting a B cell lymphoma cell line into a long-lasting antitumor vaccine," *J Immunol.*, 162(8):5003-5010, Apr. 15, 1999.

Gunn et al., "Correct end use during end joining of multiple chromosomal double strand breaks is influenced by repair protein RAD50, DNA-dependent protein kinase DNA-PKcs, and transcription context," *J Biol Chem.*, 286(49):42470-42482, Epub Oct. 24, 2011.

Guo et al., "A novel fusion protein of IP1 O-scFv retains antibody specificity and chemokine function," *Biochem Biophys Res Commun.*, 320(2):506-513, Jul. 23, 2004.

Haendeler et al., "Nitric Oxide and Apoptosis," *Vitam Horm.*, 57:49-77, 1999.

Hansen et al., "Monoclonal antibodies identifying a novel T-cell antigen and Ia antigens of human lymphocytes," *Immunogenetics*, 10(1-4):247-260, Feb. 1, 1980.

Harlow and Lane., "Antibodies: A Laboratory Manual," Cold Spring Harbor Laboratory Press, Cold Spring Harbor, NY, pp. 553, 555-582, 584-589, 591-612, 1988.

Harrington et al., "Differentiating between memory and effector CD8 T cells by altered expression of cell surface O-glycans," J Exp Med., 191(7):1241-1246, Apr. 3, 2000.

Hatzoglou et al., "Hepatic gene transfer in animals using retroviruses containing the promoter from the gene for phosphoenolpyruvate carboxykinase" *J Biol Chem.*, 265(28):17285-17293, Oct. 5, 1990.

Haugland et al, "Unit 16.5 antibody conjugates for cell biology," *Current Protocosl in cell biology.*, 6:16.5:16.5-16.5.22, Epub May 1, 2001.

Hawiger et al., "Dendritic cells induce peripheral T cell unresponsiveness under steady state conditions in vivo," *J Exp Med.*, 194(6):769-779, Sep. 17, 2001.

Hayakawa et al., "Inhibition of BAD phosphorylation either at serine 112 via extracellular signal-regulated protein kinase cascade or at serine 136 via Akt cascade sensitizes human ovarian cancer cells to cisplatin," *Cancer Res.*, 60(21):5988-5994, Nov. 1, 2000.

He et al., "Identification of a novel splice valiant of human PD-L1 mRNA encoding an isofonn-lacking IgV-like domain," *Acta Pharmacol Sin.*, 26(4):462-468, Apr. 2005.

Hellstrom et al., "T cell immunity to tumor antigens," *Crit Rev Immunol.*, 18(1-2):1-6, 1998.

Henry et al., "Cloning, structural analysis, and mapping of the B30 and B7 multigenic families to the major histocompatibility complex (MHC) and other chromosomal regions," *Immunogenetics*, 46(5):383-395, 1997.

Henry et al., "Structure and evolution of the extended B7 family," *Immunol Today*, 20(6):285-288, Jun. 1999.

Hentikoff, "Amino acid substitution matrices from protein blocks," *Proc Natl Acad Sci U S A.*, 89(22):10915-10919, Nov. 15, 1992.

Hestdal et al., "Characterization and regulation of RB6-8C5 antigen expression on murine bone marrow cells," *J Immunol.*, 147(1):22-28, Jul. 1, 1991.

Hildeman et al., "Activated T cell death in vivo mediated by proapoptotic bcl-2 family member bim," *Immunity*, 16(6):759-767, Jun. 2002.

Hirano et al., "Blockade of B7-H1 and PD-1 by monoclonal antibodies potentiates cancer therapeutic immunity," *Cancer Res.*, 65(3):1089-1096, Feb. 1, 2005.

Hiroishi et al., "Interferon-alpha gene therapy in combination with CDS0 transduction reduces tumorigenicity and growth of established tumor in poorly immunogenic tumor models," *Gene Ther.*, 6(12):1988-1994, Dec. 1999.

Hochman et al., "An active antibody fragment (Fv) composed of the variable portions of heavy and light chains," *Biochemistry*, 12(6):1130-1135, Mar. 13, 1973.

Hock et al., "Retrovirus-mediated transfer and expression of drug resistance genes in human haematopoietic progenitor cells," *Nature*, 320:275-277, 1986.

Hoffman, "T Cells in the Pathogenesis of Systemic Lupus Erythematosus," *Front Biosci.*, 6:D1369-D1378, Oct. 1, 2001.

Hoiseth et al., "Aromatic-dependent *Salmonella* typhimurium are non-virulent and effective as live vaccines," *Nature*, 291(5812):238-239, May 21, 1981.

Hollinger et al., "Diabodies": small bivalent and bispecific antibody fragments, *Proc Natl Acad Sci U S A.*, 90(14):6444-6448, Jul. 15, 1993.

Holt et al., "Domain antibodies: proteins for therapy," *Trends Biotechnol.*, 21(11):484-490, Nov. 2003.

Hori et al., "B7-H1-induced apoptosis as a mechanism of immune privilege of corneal allografts," *J Immunol.*, 177(9):5928-5935, Nov. 1, 2006.

Huai et al., "Inducible gene expression with the Tet-on system in CD4+ T cells and thymocytes of mice," *Genesis*, 45(7):427-431, Jul. 2007.

Huang et al., "The liver eliminates T cells undergoing antigen-niggered apoptosis in vivo," *Immunity*, 1(9):741-749, Dec. 31, 1994.

Huang, "Structural chemistry and therapeutic intervention of protein-protein interactions in immune response, human immunodeficiency virus entry, and apoptosis," *Pharmacol Ther.*, 86(3):201-215, Jun. 2000.

Hubbard et al., "Anti-neutrophil-elastase defenses of the lower respiratory tract in alpha 1-antitrypsin deficiency directly augmented with an aerosol of alpha I-antitrypsin," *Ann Intern Med*, 111(3):206-212, Aug. 1, 1989.

Hunter, "Diabetes in pregnancy," Effective Care in Pregnancy and Childbirth, Chalmers et al. (eds.), Oxford University Press, vol. 1, pp. 578-593, 1989.

Huse et al., "Generation of a large combinatorial library of the immunoglobulin repertoire in phage lambda," *Science*, 246(4935):1275-1281, Dec. 8, 1989.

(56) References Cited

OTHER PUBLICATIONS

Huston et al., "Protein engineering of antibody binding sites: recovery of specific activity in an anti-digoxin single-chain Fv analogue produced in *Escherichia coli,*" *Proc Natl Acad Sci U S A.*, 85(16):5879-5883, Aug. 1988.
Hutloff et al., "ICOS is an inducible T-cell co-stimulator structurally and functionally related to CD28," *Nature*, 397(6716):263-266, Jan. 21, 1999.
Hyrup et al., "Peptide nucleic acids (PNA): synthesis, properties and potential applications," *Bioorg Med Chem.*, 4(1):5-23, Jan. 31, 1996.
Ichikawa and Chen, "Role of B7-H1 and B7-H4 molecules in down-regulating effector phase of T-cell immunity: novel cancer escaping mechanisms," *Front Biosci.*, 10:2856-2860, Sep. 1, 2005.
Ikemizu et al., "Structure and dimerization of a soluble form of B7-1," *Immunity*, 12(1):51-60, Jan. 2000.
Ikonomidis, "Delivery of a viral antigen to the class I processing and presentation pathway by Listeria monocytogenes," *J Exp Med.*, 180(6):2209-2218, Dec. 1, 1994.
Inman et al. "PD-L1 (B7-H1) expression by urothelial carcinoma of the bladder and BCG-induced granulomata: associations with localized stage progression," *Cancer*, 109(8):1499-1505, Apr. 15, 2007.
Inman et al., "Questionable relevance of gamma delta T lymphocytes in renal cell carcinoma," *J Immunol.*, 180(5):3578-3584, Mar. 1, 2008.
International Preliminary Report on Patentability for PCT/US2014/053870, dated Apr. 5, 2016, 7 pages.
International Preliminary Report on Patentability in International Application No. PCT/US03/22029, dated Mar. 25, 2005, 5 pages.
International Preliminary Report on Patentability in International Application No. PCT/US07/060133, dated Oct. 30, 2008, 8 pages.
International Preliminary Report on Patentability in International Application No. PCT/US07/60150, dated Sep. 18, 2008, 5 pages.
International Preliminary Report on Patentability in International Application No. PCT/US2007/066970, dated Oct. 30, 2008, 8 pages.
International Preliminary Report on Patentability in International Application No. PCT/US2015/031993, dated Nov. 22, 2016, 11 pages.
International Preliminary Report on Patentability in International Application No. PCT/US2015/032016, dated Jan. 24, 2017, 11 pages.
International Preliminary Report on Patentability re PCT/US2009/035495, dated Sep. 10, 2010, 5 pages.
International Search Report and Written Opinion for PCT/US16/58852, dated Apr. 28, 2017, 15 pages.
International Search Report and Written Opinion for PCT/US2014/053870, dated Feb. 4, 2015, 12 pages.
International Search Report and Written Opinion for PCT/US2015/031993, dated Sep. 29, 2015, 18 pages.
International Search Report and Written Opinion for PCT/US2015/032016, dated Aug. 26, 2015, 17 pages.
International Search Report and Written Opinion in International Application No. PCT/US07/60133, dated Sep. 25, 2008, 13 pages.
International Search Report and Written Opinion in International Application No. PCT/US07/60150, dated Jul. 7, 2008, 8 pages.
International Search Report and Written Opinion in International Application No. PCT/US2007/066970, dated Oct. 5, 2007, 13 pages.
International Search Report and Written Opinion of the International Search Authority re PCT/US2009/035495, dated Oct. 6, 2009, 7 pages.
International Search Report for PCT/US2002/32364, dated Mar. 25, 2003, 2 pages.
International Search Report in International Application No. PCT/US03/22029, dated Dec. 2, 2004, 5 pages.
Invitation to Pay for PCT/US2014/053870, dated Nov. 19, 2014, 3 pages.

Ishida et al., "Differential expression of PD-L1 and PD-L2, ligands for an inhibitory receptor PD-1, in the cells of lymphohematopoietic tissues," *Immunol Lett.*, 84(1):57-62, Oct. 21, 2002.
Ishida et al., "Induced expression of PD-1, a novel member of the immunoglobulin gene superfamily, upon programmed cell death," *EMBO J.*, 11(11):3887-3895, Nov. 1992.
Iwai et al., "Involvement of PD-L1 on tumor cells in the escape from host immune system and tumor immunotherapy by PD-L1 blockade," Proc Natl Acad Sci U S A., 99(19):12293-12297, Epub Sep. 6, 2002.
Iwai et al., "PD-1 inhibits antiviral immunity at the effector phase in the liver," *J Exp Med.*, 198(1):39-50, Jul. 7, 2003.
Jacinto et al., "SIN1/MIP1 maintains rictor-mTOR complex integrity and regulates Akt phosphogylation and substrate specificity," *Cell*, 127(1):125-137, Epub. Sep. 7, 2006.
Jacobson et al., "Unique site of IgG2a and rheumatoid factor production in MRL/lpr mice," *Immunol Rev.*, 156:103-110, Apr. 1997.
Janeway et al. "Immunobiology: the Immune System in Health and Disease," *Elsevier Science.*, 4:36, 1999.
Jayaraman, "Flow cytometric determination of mitochondrial membrane potential changes during apoptosis of T lymphocytic and pancreatic beta cell lines: comparison of tetramethylrhodamineethylester (TMRE), chloromethyl-X-rosamine (HZ-CMX-Ros) and MitoTracker Red 580 (MTR580)," *J Immunol Methods.*, 306(1-2):68-79, Epub Sep. 29, 2005.
Jeannin et al., "Soluble CD86 is a costimulatory molecule for human T lymphocytes," *Immunity*, 13(3):303-312, Sep. 2000.
Jemal et al., "Cancer Statistics, 2005," *CA Cancer J Clin*, 55(1):10-30, Jan.-Feb. 2005.
Jerne, "Towards a network theory of the immune system," *Ann Immunol (Paris).*, 125C(1-2):373-389, Jan. 1974.
Jiang et al., "Genome-wide association study for biomarker identification of Rapamycin and Everolimus using a lymphoblastoid cell line system," *Front Genet.*, 4:166, Aug. 30, 2013.
Johnston et al., "Biolistic transformation of animal tissue," *In Vitro Cell Dev Biol Anim.*, 27P: 11-14 (1991).
Jones et al., "Replacing the complementarity-determining regions in a human antibody with those from a mouse," *Nature*, 321(6069):522-525, May 29-Jun. 4, 1986.
Kabat et al., Sequences of Proteins of Immunological Interest, Fifth Edition, U.S. Department of Health and Human Services, NIH Publication No. 91-3242, Table of Contents, 20 pages, 1991.
Kaleko et al., "Persistent gene expression after retroviral gene transfer into liver cells in Vivo," *Hum Gene Ther.*, 2(1):27-32, Spring 1991.
Kaliyaperumal et al., "Antigen-specific therapy of murine lupus nephritis using nucleosomal peptides: tolerance spreading impairs pathogenic function of autoimmune T and B cells," *J Immunol.*, 162(10):5775-5783, May 15, 1999.
Kalled et al., "Anti-CD40 ligand antibody treatment of SNF1 mice with established nephritis: preservation of kidney function," *J Immunol.*, 160(5):2158-2165, Mar. 1, 1998.
Kanai et al., "Blockade of B7-H1 suppresses the development of chronic intestinal inflammation," *J Immunol.*, 171(8):4156-4163, Oct. 15, 2003.
Kaneko et al., "Augmentation of Va14 NKT cell-mediated cytotoxicity by interleukin 4 in an autocrine mechanism resulting in the development of concanavalin A-induced hepatitis," *J Exp Med.*, 191(1):105-114, Jan. 3, 2000.
Karakhanova et al., "ERK/p38 MAP-kinases and PI3K are involved in the differential regulation of B7-H1 expression in DC subsets," *Eur J Immunol*, 40(1):254-266, Jan. 2010.
Kataoka et al., "Flow cytometiic analysis of phosphorylated histone H2AX following exposure to ionizing radiation in human microvascular endothelial cells," *J Radiat Res.*, 47 (3-4):245-257 , Epub Sep. 2006.
Katou et al., "Differing phenotypes between intraepithelial and stromal lymphocytes in early-stage tongue cancer," Cancer Res., 67(23):11195-11201, Dec. 1, 2007.
Kaufman et al., "A phase I trial of intra lesional RV-B7.1 vaccine in the treatment of malignant melanoma," *Hum Gene Ther.*, 11(7):1065-1082, May 1, 2000.

(56) References Cited

OTHER PUBLICATIONS

Kawabe et al., "Programmed cell death and extrathymic reduction of Vβ8+ CD4+ T cells in mice tolerant to Staphylococcus aureus enterotoxin B," Nature, 349(6306):245-248, Jan. 17, 1991.
Keir et al., "PD-1 and its ligands in tolerance and immunity," Annu Rev Immunol., 26:677-704, 2008.
Kelley et al., "Cytokines in the Pathogenesis of Systemic Lupus Erythematosus," Semin Nephrol., 19(1):57-66, Jan. 1999.
Kennerdell et al., "Use of dsRNA-mediated genetic interference to demonstrate that frizzled and frizzled 2 act in the wingless pathway," Cell, 95(7):1017-1026, Dec. 23, 1998.
Khalbanda et al., "Translocation of SAPK/JNK to mitochondria and interaction with Bcl-x(L) in response to DNA damage," J Biol Chem., 275(1):322-327, Jan. 7, 2000.
Kiessling et al., "High-throughput mutation profiling of CTCL samples reveals KRAS and NRAS mutations sensitizing tumors toward inhibition of the RAS/RAF/MEK signaling cascade," Blood, 117(8):2433-2440, Epub Jan. 5, 2011.
Kim et al., "Features of responding T cells in cancer and chronic infection," Curr Opin Immunol., 22(2):223-230, Epub Mar. 6, 2010.
Kim et al., "Therapeutic potential of 4-1BB (CD137) as a regulator for effector CD8(+) T cells," J Hematother Stem Cell Res., 10(4):441-449, Aug. 2001.
Köhler et al., "Continuous cultures of fused cells secreting antibody of predefined specificity," Nature, 256(5517):495-497, Aug. 7, 1975.
Kohn et al. "Gene therapy for genetic diseases," Cancer Invest., 7(2):179-192, 1989.
Konieczny et al., "The combination of IgM subunits and proteolytic IgG fragment by controlled formation of interchain disulphides," Haematologia (Budap)., 14(1):95-99, 1981.
Korkola et al, "Gene expression-based classification of nonseminomatous male germ cell tumors," Oncogene, 24(32):5101-5107, Jul. 28, 2005.
Kosari et al, "Clear cell renal cell carcinoma: gene expression analyses identify a potential signature for tumor aggressiveness," Clin Cancer Res., 11(14):5128-5139, Jul. 15, 2005.
Kozbor et al. "The production of monoclonal antibodies from human lymphocytes," Immunology Today, 4(3):72-79, Mar. 1, 1983.
Krempski et al., "Tumor-infiltrating programmed death receptor-1+ dendritic cells mediate immune suppression in ovarian cancer," J Immunol., 186(12):6905-6913, Epub May 6, 2011.
Kruege et al., "The role of CD95 in the regulation of peripheral T-cell apoptosis," Immunol Rev., 193:58-69, Jun. 2003.
Krummel et al., "CTLA-4 engagement inhibits IL-2 accumulation and cell cycle progression upon activation of resting T cells," J Exp Med., 183(6):2533-2540, Jun. 1, 1996.
Kuiper et al., "B7.1 and Cytokines: Synergy in cancer gene therapy," Adv Exp Med Biol., 465:381-390, 2000.
Kusmartsev et al., "Gr-1+ myeloid cells derived from tumor-bearing mice inhibit primary T cell activation induced through CD3/CD28 costimulation," J Immunol., 165(2):779-785, Jul. 15, 2000.
Kwon et al., "4-1BB: Still in the Midst of Darkness," Mol Cells., 10(2):119-126, Apr. 30, 2000.
LaBaer, "So, you want to look for biomarkers (introduction to the special biomarkers issue)," J Proteome Res., 4(4):1053-1059, Jul.-Aug. 2005.
Larrubia et al., "Bim-mediated apoptosis and PD-1/PD-L1 pathway impair reactivity of PD1(+)/CD127(−) HCV-specific CD8(+) cells targeting the virus in chronic hepatitis C virus infection," Cell Immunol., 269(2):104-114, Epub Mar. 17, 2011.
Latchman et al., "PD-L2 is a second ligand for PD-1 and inhibits T cell activation," Nat Immunol., 2(3):261-268, Mar. 2001.
Lawson et al., "Treatment of murine lupus with cDNA encoding IFN-gammaR/Fc," J Clin Invest., 106(2):207-215, Jul. 2000.
Lazarevic and Glimcher, "T-bet in disease," Nat Immunol., 12(7):597-606, Jun. 20, 2011.
Lee et al., "Survivin expression and its clinical significance in pancreatic cancer," BMC Cancer, 5:127, Oct. 4, 2005.

Lee et al., "Increased vaccine-specific T cell frequency after peptide-based vaccination correlates with increased susceptibility to in vitro stimulation but does not lead to tumor regression," J Immunol., 163(11):6292-6300, Dec. 1, 1999.
Leibovich et al., "Prediction of progression after radical nephrectomy for patients with clear cell renal cell carcinoma: a stratification tool for prospective clinical trials," Cancer, 97(7): 1663-1671, Apr. 1, 2003.
Lenardo et al., "Mature T lymphocyte apoptosis—immune regulation in a dynamic and unpredictable antigenic environment," Annu Rev Immunol., 17:221-253, 1999.
Lenschow et al., "CD28/B7 system of T cell costimulation," Annu Rev Immunol., 14:233-258, 1996.
Levitt, "Accurate modeling of protein conformation by automatic segment matching," J Mol Biol., 226(2):507-533, Jul. 20, 1992.
Lewinski, et al., Retroviral DNA integration: viral and cellular determinants of target-site selection, PLoS Pathog., 2(6):e60, Epub Jun. 23, 2006.
Lewis et al., "Surrogate tumor antigen vaccination induces tumor-specific immunity and the rejection of spontaneous metastases," Cancer Res, 65(7):2938-2946, Apr. 1, 2005.
Lewis, "PCR's Competitors Are Alive and Well and Moving Rapidly Towards Commercialization," Genetic Engineering News, vol. 12, 3 pages, 1992.
Li et al., "Anti-programmed death-1 synergizes with granulocyte macrophage colony-stimulating factor—secreting tumor cell immunotherapy providing therapeutic benefit to mice with established tumors," Clin Cancer Res., 15(5):1623-1634, Epub Feb. 10, 2009.
Li et al., "Gemcitabine and arabinosylcytosin pharmacogenomics: genome-wide association and drug response biomarkers," PLoS One., 4(11):e7765, Nov. 9, 2009.
Liang et al., "Autoantibody responses and pathology regulated by B7-1 and B7-2 costimulation in MRL/lpr lupus," J Immunol., 165(6):3436-3443, Sep. 15, 2000.
Linsley et al., "Binding of the B cell activation antigen B7 to CD28 costimulates T cell proliferation and interleukin 2 mRNA accumulation" J Exp Med., 173(3):721-730, Mar. 1, 1991.
Linsley et al., "Extending the B7 (CD80) gene family," Protein Sci., 3(8):1341-1343, Aug. 1994.
Linsley et al., "T-cell antigen CD28 mediates adhesion with B cells by interacting with activation antigen 87188-1," Proc Natl Acad Sci U S A., 87(13):5031-5035, Jul. 1990.
Liu et al., "B7DC/PDL2 promotes tumor immunity by a PD-1-independent mechanism," J Exp Med., 197(12):1721-1730, Jun. 16, 2003.
Liu et al., "B7-H3 silencing increases paclitaxel sensitivity by abrogating Jak2/Stat3 phosphorylation," Mol Cancer Ther., 10(6):960-971, Epub Apr. 25, 2011.
Liu et al., "Endogenous tumor-reactive CD8+ T cells are differentiated effector cells expressing high levels of CD11a and PD-1 but are unable to control tumor growth," Oncoimmunology., 2(6):e23972, Epub Jun. 6, 2013.
Liu et al., "Fas-mediated apoptosis causes elimination of Virus-specific cytotoxic T cells in the virus-infected liver," J Immunol, 166(5):3035-3041, Mar. 1, 2001.
Liu et al., "Plasma cells from multiple myeloma patients express B7-H1 (PD-L1) and increase expression after stimulation with IFN-{gamma} and TLR ligands via a MyD88−, TRAF6−, and MEK-dependent pathway," Blood, 110(1):296-304, Epub Mar. 15, 2007.
Lonberg et al., "Antigen-specific human antibodies from mice compiising four distinct genetic modifications," Nature, 368(6474):856-859, Apr. 28, 1994.
Losman et al., "Baboon anti-idiotype antibodies mimic a carcinoembryonic antigen epitope," Int J Cancer, 46(2):310-314, Aug. 15, 1990.
Lu et al., "EGF-IL-18 fusion protein as a potential anti-tumor reagent by induction of immune response and apoptosis in cancer cells," Cancer Lett., 260(1-2):187-197, Epub Dec. 21, 2007.

(56) References Cited

OTHER PUBLICATIONS

Luciano et al., "Phosphorylation of Bim-EL by Erk1/2 on serine 69 promotes its degradation via the proteasome pathway and regulates its proapoptotic function," *Oncogene.*, 22(43):6785-6793, Oct. 2, 2003.
Luettig et al., "Naive and memory T lymphocytes migrate in comparable numbers through normal rat liver: activated T cells accumulate in the periportal field," *J Immunol.*, 163(8):4300-4307, Oct. 15, 1999.
Lunsford et al., "Targeting LFA-1 and cd154 suppresses the in vivo activation and development of cytolytic (cd4-Independent) CD8+ T cells," J Immunol., 175(12):7855-7866, Dec. 15, 2005.
Ma et al., "The DNA-dependent protein kinase catalytic subunit phosphorylation sites in human Artemis," *J Biol Chem*, 280(40):33839-33846, Epub Aug. 10, 2005.
Ma et al., "The Role of PD-1 Ligand in Immune Evasion by Breast Cancer," Dana-Farber Cancer Institute Annual Summary Report May 1, 2002-Apr. 30, 2005, pp. 5-6, 9, 11, report date: May 2005.
Mah et al., "gammaH2AX: a sensitive molecular marker of DNA damage and repair," *Leukemia*, 24(4):679-686, Epub Feb. 4, 2010.
Mahotka et al., "Distinct in vivo expression patterns of survivin splice variants in renal cell carcinomas," *Int J Cancer*, 100(1):30-36, Jul. 1, 2002.
Mann et al., "Construction of a retrovirus packaging mutant and its use to produce helper-free defective retrovirus" *Cell*, 33(1):153-159, May 1983.
Martin et al. "Combination gene therapy with CD86 and the MHC Class II transactivator in the control of lung tumor growth," *J Immunol.*, 162(11):6663-6670, Jun. 1, 1999.
Metzler et al., "Solution structure of human CTLA-4 and delineation of a CD80/CD86 binding site conserved in CD28," *Nat Struct Biol.*, 4(7):527-531, Jul. 1997.
Miller et al., "Gene transfer by retrovirus vectors occurs only in cells that are actively replicating at the time of infection," *Mol Cell Biol.*, 10(8):4239-4242, Aug. 1990.
Miller et al., "Generation of helper-free amphotropic retroviruses that transduce a dominant-acting, methotrexate-resistant dihydrofolate reductase gene," *Mol Cell Biol.*, 5(3):431-437, Mar. 1985.
Miller et al., "Redesign of retrovirus packaging cell lines to avoid recombination leading to helper virus production," *Mol Cell Biol.*, 6(8):2895-2902, Aug. 1986.
Miller, "Human gene therapy comes of age," *Nature*, 357(6378):455-460, Jun. 11, 1992.
Misquitta et al., "Targeted disruption of gene function in Drosophila by RNA interference (RNA-i): A role for nautilus in embryonic somatic muscle formation," *Proc Natl Acad Sci U S A*., 96(4):1451-1456, Feb. 16, 1999.
Mizuhara et al., "T cell activation-associated hepatic injury: mediation by tumor necrosis factors and protection by interleukin 6," *J Exp Med.*, 179(5):1529-1537, May 1, 1994.
Mohan et al., "Interaction between CD40 and its ligand gp39 in the development of murine lupus nephritis," *J Immunol.*, 154(3):1470-1480, Feb. 1, 1995.
Montesano et al, "Genetic alterations in esophageal cancer and their relevance to etiology and pathogenesis: a review," *Int J Cancer.*, 69(3):225-235, Jun. 21, 1996.
Morrison et al., "Chimeric human antibody molecules: mouse antigen-binding domains with human constant region domains," *Proc Natl Acad Sci U S A*., 81(21):6851-6855, Nov. 1984.
Morse et al., "Abnormalities induced by the mutant gene Ipr: expansion of a unique lymphocyte subset," *J Immunol.*, 129(6):2612-2615, Dec. 1982.
Moss, "Poxvirus expression vectors," *Curr Top Microbiol Immunol.*, 158:25-38, 1992.
Moss, "Poxvirus vectors: cytoplasmic expression of transferred genes," *Curr Opin Genet Dev.*, 3(1):86-90, Feb. 1993.
Moss, "Use of vaccinia virus as an infectious molecular cloning and expression vector," *Gene Amplif Anal.*, 3:201-213, 1983.
Moss, "Vaccinia virus vectors," Biotechnology, 20:345-362, 1992.
Moss, "Vaccinia virus: a tool for research and vaccine development," *Science*, 252(5013):1662-1667, Jun. 21, 1991.
Motzer et al., "Renal Cell Carcinoma," *N Engl J Med.*, 335(12):865-75, Sep. 19, 1996.
Mukherjee et al., "DNA-PK phosphorylates histone H2AX during apoptotic DNA fragmentation in mammalian cells," *DNA Repair (Amst).*, 5(5):575-590, Epub Mar. 29, 2006.
Mumprecht et al., "Programmed death 1 signaling on chronic myeloid leukemia-specific T cells results in T-cell exhaustion and disease progression," *Blood.*, 114(8):1528-1536. Epub May 6, 2009.
Muyldermans, "Single domain camel antibodies: current status," *J Biotechnol.*, 74(4):277-302, Jun. 2001.
Nabel et al., "Recombinant gene expression in vivo within endothelial cells of the arterial wall," *Science*, 244(4910):1342-1344, Jun. 16, 1989.
Mathiowitz et al., "Morphology of poly anhydride microsphere delivery systems," *Scanning Microsc.*, 4(2):329-340, Jun. 1990.
Mathiowitz et al., "Polyanhydride microspheres as drug carriers. I. Hot-melt microencapsulation," *J. Controlled Release*, 5(1):13-22, Jun. 1, 1987.
Mathiowitz et al., "Polyanhydride microspheres. IV. Morphology and characterization of systems made by spray drying," *J. Appl. Polymer Sci.* 45(1): 125-134, May 5, 1992.
Mathiowitz, Novel microcapsules for delivery systems, *Reactive Polymers*, 6(2):275-283, Oct. 31, 1987.
Mathiowitz, "Polyanhydride microspheres as drug carriers, II. Microencapsulation by solvent removal," *J. Appl. Polymer Sci.*, 35(3): 755-774, Feb. 20, 1988.
Mayo Clinic, "Mayo Clinic Discovers Potential Marker for Aggressive Kidney Cancer," Science Daily, Retrieved from the Internet: <URL: https://www.sciencedaily.com/releases/2004/11/041130200858. htm>, 2 pages, Dec. 9, 2004.
McCubrey et al., "Roles of the Raf/MEK/ERK pathway in cell growth, malignant transformation and drug resistance," *Biochim Biophys Acta.*, 1773(8):1263-1284, Epub Oct. 7, 2006.
McDermott et al., "PD-1 as a potential target in cancer therapy," Cancer Med., 2(5):662-673. Epub Jul. 21, 2013.
McLachlin et al., "Retroviral-mediated gene transfer," *Prog Nucleic Acid Res Mol Biol.*, 38:91-135, 1990.
Mehal et al., "Antigen presentation by liver cells controls intrahepatic T cell trapping, whereas bone marrow-derived cells preferentially promote intrahepatic T cell apoptosis," *J Immunol*, 167(2):667-673, Jul. 15, 2001.
Mehal et al., "TCR ligation on CD8+ T cells creates double-negative cells in vivo," *J Immunol.*, 161(4):1686-1693, Aug. 15, 1998.
Melero et al., "Amplification of tumor immunity by gene transfer of the co-stimulatory 4-1BB ligand: synergy with the CD28 co-stimulatory pathway," *Eur J Immunol.*, 28(3):1116-1121, Mar. 1998.
Melero et al., "Monoclonal antibodies against the 4-1BB T-cell activation molecule eradicate established tumors," *Nat Med.*, 3(6):682-685, Jun. 1997.
Melero et al., "NK1.1 cells express 4-1BB (CDw137) costimulatory molecule and are required for tumor immunity elicited by anti-4-1BB monoclonal antibodies," *Cell Immunol*, 190(2):167-172, Dec. 15, 1998.
Melief et al., "Strategies for immunotherapy of cancer," *Advances in immunology*, 75:235-282, Jan. 1, 2000.
Mendez-Fernandez et al., "Clearance of Theiler's Virus infection depends on the ability to generate a CD8+ T cell response against a single immunodominant viral peptide," *Eur J Immunol.*, 33(9):2501-2510, Sep. 2003.
Merrill, "Emergence of targeted immune therapies for systemic lupus," *Expert Opin Emerg Drugs*, 10(1):53-65, Feb. 2005.
Merritt et al., "Activation of p38 mitogen-activated protein kinase in vivo selectively induces apoptosis of CD8(+) but not CD4(+) T cells," *Mol Cell Biol.*, 20(3):936-946, Feb. 2000.
National Cancer Institute, "Fact Sheet: Tumor Markers," cancer.gov [online] Dec. 7, 2011 [retrieved on Apr. 3, 2014]. Retrieved from the Internet: <URL: http://www.cancer.gov/cancertopics/factsheet/ detection/tumor-markers/print>, 8 pages.

(56) References Cited

OTHER PUBLICATIONS

Nava-Parada et al., "Peptide vaccine given with a Toll-like receptor agonist is effective for the treatment and prevention of spontaneous breast tumors," Cancer Res., 67(3):1326-1334, Feb. 1, 2007.
Nechiporuk et al., "The mouse SCA2 gene: cDNA sequence, alternative splicing and protein expression," Hum Mol Genet., 7(8):1301-1309, Aug. 1998.
Needleman et al., "A general method applicable to the Search for similarities in the amino acid sequence of two proteins," J Mol Biol., 48(3):443-453, Mar. 1970.
Nelson et al., "Tumor progression despite efficient tumor antigen cross-presentation and effective "arming" of tumor antigen-specific CTL," J Immunol., 166(9):5557-5566, May 1, 2001.
Neves et al., "Surgical treatment of renal cancer with vena cava extension," Br J Urol., 59(5):390-395, May 1987.
Newmark et al., "Preparation and properties of adducts of streptokinase and streptokinase-plasmin complex with poly ethylene glycol and pluronic polyol F38," J Appl Biochem., 4:185-189, 1982.
Nicolau et al., "In vivo expression of rat insulin after intravenous administration of the liposome-entrapped gene for rat insulin I," Proc Natl Acad Sci U S A., 80(4):1068-1072, Feb. 1983.
Nielsen et al., "Melanoma vaccines: the paradox of T cell activation without clinical response," Cancer Chemother Pharmacol., 46 Suppl:S62-S66, 2000.
Nielsen et al., "Peptide nucleic acid (PNA). A DNA mimic with a peptide backbone," Bioconjug Chem., 5(1):3-7, Jan.-Feb. 1994.
Nielsen et al., "Sequence-selective recognition of DNA by strand displacement with a thymine-substituted polyamide," Science, 254(5037):1497-1500, Dec. 6, 1991.
Nishimura et al., "Autoimmune dilated cardiomyopathy in PD-1 receptor-deficient mice," Science, 291(5502):319-322, Jan. 12, 2001.
Nishimura et al., "Development of lupus-like autoimmune diseases by disruption of the PD-1 gene encoding an ITIM motif-carrying immunoreceptor," Immunity, 11(2):141-151, Aug. 1999.
Nishimura et al., "Immunological studies on PD-1-deficient mice: implication of PD-1 as a negative regulator for B cell responses," Int Immunol., 10(10):1563-1572, Oct. 1998.
Nisonhoff et al., "Separation of univalent fragments from the bivalent rabbit antibody molecule by reduction of disulfide bonds," Arch Biochem Biophys., 89:230-244, Aug. 1960.
Ohigashi et al., "Clinical significance of programmed death-1 ligand-1 and programmed death-1 ligand-2 expression in human esophageal cancer," Clin Cancer Res., 11(8):2947-2953, Apr. 15, 2005.
Okazaki et al., "PD-1 and PD-1 ligands: from discovery to clinical application," Int Immunol., 19(7):813-824, Epub Jul. 2, 2007.
Opferman al., "Linear differentiation of cytotoxic effectors into memory T lymphocytes," Science, 283(5408):1745-1748, Mar. 12, 1999.
O'Reilly et al., "MEK/ERK-mediated phosphorylation of Bim is required to ensure survival of T and B lymphocytes during mitogenic stimulation," J Immunol., 183(1):261-269, Jul. 1, 2009.
Orlandi et al., "Cloning immunoglobulin variable domains for expression by the polymerase chain reaction," Proc Natl Acad Sci U S A., 86(10):3833-3837, May 1989.
Ostrov et al., "Structure of murine CTLA-4 and its role in modulating T cell responsiveness," Science, 290(5492):816-819, Oct. 27, 2000.
Ozkaynak et al., "Programmed death-1 targeting can promote allograft survival," J Immunol., 169(11):6546-6553, Dec. 1, 2002.
Panta et al., "ATM and the catalytic subunit of DNA-dependent protein kinase activate NF-kappaB through a common MEK/extracellular signal-regulated kinase/p90(rsk) signaling pathway in response to distinct forms of DNA damage," Mol Cell Biol., 24(5):1823-1835, Mar. 2004.
Pantuck et al., "The changing natural history of renal cell carcinoma," J Urol., 166(5):1611-1623, Nov. 2001.
Pardoll, "Spinning molecular immunology into successful immunotherapy," Nat Rev Immunol., 2(4):227-238, Apr. 2002.
Pardoll., "The Blockade of Immune Checkpoints in Cancer Immunotherapy," Nat Review., 12:252-264, Apr. 2012.
Park et al., "B7-H1/CD80 interaction is required for the induction and maintenance of peripheral T-cell tolerance," Blood., 116(8):1291-1298, Epub May 14, 2010.
Parker et al., "Potential utility of uroplakin III, thrombomodulin, high molecular weight cytokeratin, and cytokeratin 20 in noninvasive, invasive, and metastatic urothelial (transitional cell) carcinomas," Am J Surg Pathol., 27(1):1-10, Jan. 2003.
Parsa et al., "Loss of tumor suppressor PTEN function increases B7-H1 expression and immunoresistance in glioma," Nat Med., 13(1):84-88, Epub Dec. 10, 2006.
Paterson et al., "The PD-L1:B7-1 pathway restrains diabetogenic effector T cells in vivo," J Immunol., 187(3):1097-1105, Aug. 1, 2011.
Patsoukis et al., "Selective effects of PD-1 on Akt and Ras pathways regulate molecular components of the cell cycle and inhibit T cell proliferation," Sci Signal., 5(230):ra46, Jun. 26, 2012.
Pavelko et al., "The epitope integration site for vaccine antigens determines virus control while maintaining efficacy in an engineered cancer vaccine," Mol Ther., 21(5): 1087-1095, Epub Apr. 9, 2013.
Peach et al., "Both extracellular immunoglobulin-like domains of CD80 contain residues critical for binding T cell surface receptors CTLA-4 and CD28," J Biol Chem., 270(36):21181-21187, Sep. 8, 1995.
Pece and Gutkind, "Signaling from E-cadherins to the MAPK pathway by the recruitment and activation of epidermal growth factor receptors upon cell-cell contact formation," J Biol Chem., 275(52):41227-41233, Dec. 29, 2000.
Pedraza-Alva et al., "Activation of p38 MAP kinase by DNA double-strand breaks in V(D)J recombination induces a G2/M cell cycle checkpoint," EMBO J., 25(4):763-773, Epub Feb. 2, 2006.
Peghini et al, [Immunophaenotyping in the diagnosis of lymphoma]. Praxis (Bern 1994)., 93(41): 1687-1692, Oct. 6, 2004, Article in German, English abstract included.
Pei et al., "FKBP51 affects cancer cell response to chemotherapy by negatively regulating Akt," Cancer Cell., 16(3):259-266, Sep. 8, 2009.
Penix et al., "Two essential regulatory elements in the human interferon gamma promoter confer activation specific egression in T cells," J Exp Med., 178(5): 1483-1496, Nov. 1, 1993.
Perriman et al., "Effective ribozyme delivery in plant cells," Proc Natl Acad Sci U S A., 92(13):6175-6179, Jun. 20, 1995.
Petroff et al., "B7 family molecules: novel immunomodulators at the maternal-fetal interface," Placenta, 23 Suppl A:S95-101, Apr. 2002.
Piccini, "Vaccinia: virus, vector, vaccine," Adv Virus Res., 34:43-64, 1988.
Plückthun et al., "Expression of functional antibody Fv and Fab fragments in Escherichia coli," Methods Enzymol., 178:497-515, 1989.
Plückthun, "Antibodies from Escherichia coli." The Pharmacology of Monoclonal Antibodies. Handbook of Experimental Pharmacology, Springer Berlin Heidelberg, pp. 269-315, 1994.
Poirier, "Protective immunity evoked by oral administration of attenuated aroA Salmonella typhimurium expressing cloned streptococcal M protein," J Exp. Med., 168(1):25-32, Jul. 1, 1988.
Pollok et al., "4-1BB T-cell antigen binds to mature B cells and macrophages, and costimulates anti-mu-primed splenic B cells," Eur J Immunol, 24(2):367-374, Feb. 1994.
Pollok et al., "Inducible T Cell Antigen 4-1BB," J Immunol., 150(3):771-781, Feb. 1, 1993.
Ponder et al., "Tertiary templates for proteins. Use of packing criteria in the enumeration of allowed sequences for different structural classes," J Mol Biol., 193(4):775-791, Feb. 20, 1987.
Porter, "The hydrolysis of rabbit γ-globulin and antibodies with crystalline papain," Biochem J., 73:119-126, Sep. 1959.
Powell et al., "Compendium of excipients for parenteral formulations," PDA J Pharm Sci Technol., 52(5):238-311, Sep.-Oct. 1998.
Prasad et al., "B7S1, a novel B7 family member that negatively regulates T cell activation," Immunity, 18(6):863-873, Jun. 2003.

(56) References Cited

OTHER PUBLICATIONS

Presta, "Antibody engineering," *Curr Opin Biotechnol.*, 2(4):593-596, 1992.
Presta, "Antibody engineering," *Curr Opin Biotechnol.*, 3(4):394-398, Aug. 1992.
Prévost-Blondel et al., "Tumor-infiltrating lymphocytes exhibiting high ex vivo cytolytic activity fail to prevent murine melanoma tumor growth in vivo," *J Immunol.*, 161(5):2187-2194, Sep. 1, 1998.
Pulko et al., "B7-h1 expressed by activated CD8 T cells is essential for their survival," *J Immunol.*, 187(11):5606-5614, Epub Oct. 24, 2011.
Pulko et al., "TLR3-stimulated dendritic cells up-regulate B7-H1 expression and influence the magnitude of CD8 T cell responses to tumor vaccination," *J Immunol.*, 183(6):3634-3641, Epub Aug. 26, 2009.
Qi et al., "Evidence that Ser87 of BimEL is phosphorylated by Akt and regulates BimEL apoptotic function," *J Biol Chem.*, 281(2):813-823, Epub Nov. 10, 2005.
Radhakrishnan et al., "Dendritic cells activated by cross-linking B7-DC (PD-L2) block inflammatory airway disease," *J Allergy Clin Immunol.*, 116(3):668-674, Sep. 2005.
Rai et al., "Tracking the total CD8 T cell response to infection reveals substantial discordance in magnitude and kinetics between inbred and outbred hosts," J Immunol., 183(12):7672-7681, Dec. 15, 2009.
Rajewsky et al., "Genetics, expression, and function of idiotypes," *Annu Rev Immunol.*, 1:569-607, 1983.
Rathmell et al., "The central effectors of cell death in the immune system," *Annu. Rev. Immunol.*, 17:781-828, 1999.
Razi-Wolf, "Expression and function of the murine B7 antigen, the major costimulatory molecule expressed by peritoneal exudate cells," *Proc Natl Acad Sci U S A.*, 89(9):4210-4214, May 1, 1992.
Renauld et al., "Expression cloning of the murine and human interleukin 9 receptor cDNAs," *Proc Natl Acad Sci U S A.*, 89(12):5690-5694, Jun. 15, 1992.
Riechmann et al., "Reshaping human antibodies for therapy," *Nature*, 332(6162):323-327, Mar. 24, 1988.
Rincon et al., "JNK and p38 MAP kinases in CD4+ and CD8+ T cells," *Immunol Rev.*, 192:131-142, Apr. 2003.
Ritz et al., "Bioassay analysis using R," *J Stat Softw.*, 12(5):1-22, Jan. 19, 2005.
Rivoltini et al., "Immunity to cancer: attack and escape in T lymphocyte-tumor cell interaction," *Immunol Rev.*, 188:97-113, Oct. 2002.
Robison-Cox, "Multiple estimation of concentrations in immunoassay using logistic models," *J Immunol Methods*, 186(1):79-88, Oct. 12, 1995.
Romano et al., "Quelling: transient inactivation of gene expression in Neurospora crassa by transformation with homologous sequences," *Mol Microbiol.*, 6(22):3343-3353, Nov. 1992.
Romero et al., "Ex vivo staining of metastatic lymph nodes by class I major histocompatibility complex tetramers reveals high numbers of antigen-experienced tumor-specific cytolytic T lymphocytes," *J Exp Med.*, 188(9):1641-1650, Nov. 2, 1998.
Rosenberg, "Progress in human tumor immunology and immunotherapy," *Nature*, 411(6835):380-384, May 17, 2001.
Rosenfeld et al., "Adenovirus-mediated transfer of a recombinant alpha 1-antitrypsin gene to the lung epithelium in vivo," *Science*, 252(5004):431-434, Apr. 19, 1991.
Rousseaux et al, "Optimal conditions for the preparation of proteolytic fragments from monoclonal IgG of different rat IgG subclasses," *Methods Enzymol.*, 121:663-669, 1986.
Rowe et al., "PDL-1 blockade impedes T cell expansion and protective immunity primed by attenuated Listeria monocytogenes," *J Immunol.*, 180(11):7553-7557, Jun. 1, 2008.
Sadoff, "Oral *salmonella* typhimurium vaccine expressing circumsporozoite protein protects against malaria," *Science*, 240(4850):336-338, Apr. 15, 1988.

Salama et al., "Critical role of the programmed death-1 (PD-1) pathway in regulation of experimental autoimmune encephalomyelitis," *J Exp Med.*, 198(1):71-78, Jul. 7, 2003.
Salib et al., "Utilization of sodium alginate in drug microencapsulation," *Pharm Ind.*, 40(11a):1230-1234, 1978.
Salih et al., "4-1 BB ligand—just another costimulating molecule?," *Int J Clin Pharmacol Ther.*, 40(8):348-353, Aug. 2002.
Salih et al., "The role of leukemia-derived B7-H1 (PD-L1) in tumor-T-call interactions in humans," *Exp Hematol.*, 34(7):888-894, Jul. 2006.
Salomon et al., "Complexities of CD28/B7: CTLA-4 costimulatory pathways in autoimmunity and transplantation," *Annu Rev Immunol.*, 19:225-252, 2001.
Samulski, "Targeted integration of adenoassociated virus (AAV) into human chromosome 19," *EMBO J.*, 10(12):3941-3950, Dec. 1991.
Sandhu, "Protein engineering of antibodies," *Crit Rev Biotechnol.*, 12(5-6):437-462, 1992.
Sanni et al., "Evolution of aminoacyl-tRNA synthetase quaternary structure and activity: *Saccharomyces cerevisiae* mitochondrial phenylalanyl-tRNA synthetase," *Proc Natl Acad Sci U S A.*, 88(19):8387-8391, Oct. 1, 1991.
Sarbassov et al., "Phosphorylation and regulation of Akt/PKB by the rictor-mTOR complex," *Science*, 307(5712):1098-1101, Feb. 18, 2005.
Sawhney et al., "Bioerodible hydrogels based on photopolymerized poly(ethylene glycol)-co-poly(.alpha.-hydroxy acid) diacrylate macromere," *Macromolecules*, 26(4):581-587, Jul. 1993.
Schafer, "Induction of a cellular immune response to a foreign antigen by a recombinant Listeria monocytogenes vaccine," *J Immunol.*, 149(1):53-59, Jul. 1, 1992.
Schmid et al, "Expression of AMPA receptor subunit flip/flop splice variants in the rat auditory brainstem and inferior colliculus," *J Comp Neurol.*, 430(2):160-171, Feb. 5, 2001.
Schmidt et al., "Extreme CD8 T cell requirements for anti-malarial liver-stage immunity following immunization with radiation attenuated sporozoites," *PLoS Pathog*, 6(7):e1000998, Jul. 15, 2010.
Schmits et al., "LFA-1-deficient mice show normal CTL responses to virus but fail to reject immunogenic tumor," *J Exp Med.*, 183(4):1415-1426, Apr. 1, 1996.
Schurich et al., "The third signal cytokine IL-12 rescues the anti-viral function of exhausted HBV-specific CD8 T cells," *PLoS Pathog.*, 9(3):e1003208, Epub Mar. 14, 2013.
Schwartz et al, "Costimulation of T lymphocytes: the role of CD28, CTLA-4, and B7/BBI in interluekin-2 production and immunotherapy," *Cell*, 71(7):1065-1068, Dec. 24, 1992.
Schwartz et al., "Structural basis for co-stimulation by the human CTLA-4/B7-2 complex," *Nature*, 410(6828):604-608, Mar. 29, 2001.
Schwartz et al., "Structural mechanisms of costimulation," *Nat Immunol.*, 3(5):427-434, May 2002.
Sedletska et al., "Cisplatin is a DNA-damaging antitumour compound triggering multifactorial biochemical responses in cancer cells: importance of apoptotic pathways," *Curr Med Chem Anticancer Agents.*, 5(3):251-265, May 2005.
Seki et al., "Tumor-specific CTL kill murine renal cancer cells using both perforin and Fas ligand-mediated lysis in vitro, but cause tumor regression in vivo in the absence of perforin," J Immunol., 168(7):3484-3492, Apr. 1, 2002.
Selenko-Gebauer et al., "B7-H1 (programmed death-1 ligand) on dendritic cells is involved in the induction and maintenance of T cell anergy," *J Immunol.*, 170(7):3637-3644, Apr. 1, 2003.
Seo et al., "Blockade of endogenous B7-H1 suppresses antibacterial protection after primary Listeria monocytogenes infection," *Immunology*, 123(1):90-99, Epub Oct. 25, 2007.
Shaknovich et al., "The promyelocytic leukemia zinc finger protein affects myeloid cell growth, differentiation, and apoptosis," *Mol Cell Biol.*, 18(9):5533-5545, Sep. 1998.
Shao et al., "Deficiency of the DNA repair enzyme ATM in rheumatoid arthritis," *J Exp Med.*, 206(6):1435-1449, Epub May 18, 2009.
Shao et al., "DNA-dependent protein kinase catalytic subunit mediates T-cell loss in rheumatoid arthritis," *EMBO Mol Med.*, 2(10):415-427, Oct. 2010.

(56) References Cited

OTHER PUBLICATIONS

Sharon et al., "Preparation of Fv fragment from the mouse myeloma XRPC-25 immunoglobulin possessing anti-dinitrophenyl activity," *Biochemistry*, 15(7):1591-1594, Apr. 6, 1976.
Sheather, "Density Estimation," *Statistical Sci.*, 19(4):588-597, 2004.
Shin et al., "Cooperative B7-1/2 (CD80/CD86) and B7-DC costimulation of CD4+ T cells independent of the PD-1 receptor," *J Exp Med.*, 198(1):31-38, Jul. 7, 2003.
Sica et al., "B7-H4, a molecule of the B7 family, negatively regulates T cell immunity," *Immunity*, 18(6):849-861, Jun. 2003.
Sica et al., "Biochemical and immunological characteristics of 4-1BB (CD137) receptor and ligand and potential applications in cancer therapy," *Arch Immunol Ther Exp (Warsz).*, 47 (5):275-279, 1999.
Siddiqui et al., "Tumor-infiltrating Foxp3-CD4+CD25+ T cells predict poor survival in renal cell carcinoma," *Clin Cancer Res.*, 13(7):2075-2081, Apr. 1, 2007.
Simon et al., "B7-h4 is a novel membrane-bound protein and a candidate serum and tissue biomarker for ovarian cancer," *Cancer Res.*, 66(3):1570-1575, Feb. 1, 2006.
Singer et al., "Optimal humanization of 1B4, an Anti-CD18 murine monoclonal antibody, is achieved by correct choice of human v-region framework sequences," *J Immunol.*, 150(7):2844-2857, Apr. 1, 1993.
Skerra et al., "Assembly of a functional immunoglobulin Fv fragment in *Escherichia coli*," *Science*, 240(4855):1038-1041, May 20, 1988.
Skolnick et al., "From genes to protein structure and function: novel applications of computational approaches in the genomic era," *Trends Biotechnol.*, 18(1):34-39, Jan. 2000.
Smith et al., Differential outcome of IL-2/anti-IL-2 complex therapy on effector and memory CD8+ T cells following vaccination with an adenoviral vector encoding EBV epitopes, J Immunol., 186(10):5784-5790, Epub Apr. 11, 2011.
Smith et al., "Pulmonary deposition and clearance of aerosolized alpha-1-proteinase inhibitor administered to dogs and to sheep," *J Clin Invest.*, 84(4):1145-1154, Oct. 1989.
Sneller et al., "A novel lymphoproliferative/autoimmune syndrome resembling murine lpr/gld disease,"*J Clin Invest.*, 90(2):334-341, Aug. 1992.
Solier et al., "Death receptor-induced activation of the Chk2- and histone H2AX-associated DNA damage response pathways," *Mol Cell Biol.*, 29(1):68-82, Epub Oct. 27, 2008.
Sorge et al., "Amphotropic retrovirus vector system for human cell gene transfer," *Mol Cell Biol.*, 4(9):1730-1737, Sep. 1984.
Soriano, "Targeted and nontargeted liposomes for in vivo transfer to rat liver cells of a plasmid containing the preproinsulin I gene," *Proc Natl Acad Sci U S A.*, 80(23):7128-7131, Dec. 1983.
Soubeyrand et al., "Artemis phosphorylated by DNA-dependent protein kinase associates preferentially with discrete regions of chromatin," *J Mol Biol.*, 358(5): 1200-1211, Epub Mar. 20, 2006.
Stammers et al., "BIL-II: A polymorphic locus with homology to the butyrolphilin gene family, located at the border of the major histocompatibility complex class II and class III regions in human and mouse," *Immunogenetics*, 51(4-5):373-382, Apr. 2000.
Stamper et al., "Crystal structure of the B7-1/CTLA-4 complex that inhibits human immune responses," *Nature*, 410(6828):608-611, Mar. 29, 2001.
Strome et al., "B7-H1 blockade augments adoptive T-cell immunotherapy for squamous cell carcinoma," *Cancer Res.*, 63(19):6501-6505, Oct. 1, 2003.
Strome et al., "Enhanced therapeutic potential of adoptive immunotherapy by in vitro CD28/4-1BB costimulation of tumor-reactive T cells against a poorly immunogenic, major histocompatibility complex class I-negative A9P melanoma," *J Immunother.*, 23(4):430-437, Jul.-Aug. 2000.
Subudhi et al., "Local expression of B7-H1 promotes organ-specific autoimmunity and transplant rejection," *J Clin Invest.*, 113(5):694-700, Mar. 2004.

Suda et al., "Why do defects in the Fas-Fas ligand system cause autoimmunity?" *J Allergy Clin Immunol.*, 100(6 Pt 2):S97-S101, Dec. 1997.
Summerton et al., "Morpholino antisense oligomers: design, preparation, and properties," *Antisense Nucleic Acid Drug Dev.*, 7(3):187-195, Jun. 1997.
Sun et al., "Administration of agonistic anti-4-1BB monoclonal antibody leads to the amelioration of expetimental autoimmune encephalomyelitis," *J Immunol.*, 168(3):1457-1465, Feb. 1, 2002.
Sun et al., "Costimulatory molecule-targeted antibody therapy of a spontaneous autoimmune disease," *Nat Med.*, 8(12):1405-1413, Epub Nov. 11, 2002.
Sun et al., "Signaling of 4-1BB Leads to Amelioration of Experimental Autoimmune Encephalomyelitis," *FASEB J.*, vol. 5, p. A1210 Abstract 950.9, 2001.
Supplementary European Search Report in International Application No. 03764649.4-2107, dated Oct. 6, 2006, 5 pages.
Sutter et al., "Nonreplicating vaccinia vector efficiently expresses recombinant genes," *Proc Natl Acad Sci U S A.*, 89(22):10847-10851, Nov. 15, 1992.
Suzuki et al., "T cell-specific loss of Pten leads to defects in central and peripheral tolerance," *Immunity*, 14(5):523-534, May 2001.
Suzuki et al., "The dual functions of fas ligand in the regulation of peripheral CD8+ and CD4+ T cells," *Proc Natl Acad Sci U S A.*, 97(4):1707-1712, Feb. 15, 2000.
Swallow et al., "B7h, a novel costimulatory homolog of B7.1 and B7.2, is induced by TNFalpha," *Immunity*, 11(4):423-432, Oct. 1999.
Takahashi et al., "Cutting edge: 4-1BB is a bona fide CD8 T cell survival signal," *J Immunol.*, 162(9):5037-5040, May 1, 1999.
Takeda et al., "Critical contribution of liver natural killer T cells to a murine model of hepatitis," *Proc Natl Acad Sci U S A.*, 97(10):5498-5503, May 9, 2000.
Tamura et al., "B7-H1 costimulation preferentially enhances CD28-indepenent T-helper cell function," *Blood*, 97(6): 1809-1816, Mar. 15, 2001.
Tamura et al., "Marrow stromal cells induce B7-H1 expression on myeloma cells, generating aggressive characteristics in multiple myeloma," *Leukemia*, 27(2):464-472, 2013.
Taylor et al., "Human imrnuno globulin transgenes undergo rearrangement, somatic mutation and class switching in mice that lack endogenous IgM," *Int Immunol.*, 6(4):579-591, Apr. 1994.
Tazi-Ahnini et al., "Cloning, localization, and structure of new members of the butyrophilin gene family in the juxtatelomenc region of the major histocompatibility complex," *Immunogenetics*, 47(1):55-63, 1997.
Temin, "Safety considerations in somatic gene therapy of human disease with retrovirus vectors," *Hum Gene Ther.*, 1(2):111-123, Summer 1990.
Templeton et al., "Improved DNA: liposome complexes for increased systemic delivery and gene expression," *Nat Biotechnol.*, 15(7):647-652, Jul. 1997.
Theofilopoulos et al., "Tumour necrosis factor and other cytokines in murine lupus," *Ann Rheum Dis.*, 58(suppl 1):I49-55, Nov. 1, 1999.
Theofilopoulos et al., "Etiopathogenesis of Murine SLE," *Immunol Rev.*, 55:179-216, 1981.
Thompson et al., "cis-acting sequences required for inducible interleukin-2 enhancer function bind a novel Ets-related protein, Elf-1," *Mol Cell Biol.*, 12(3):1043-1053, Mar. 1992.
Thompson et al., "Costimulatory B7-H1 in renal cell carcinoma patients: Indicator of tumor aggressiveness and potential therapeutic target," *Proc Natl Acad Sci U S A*, 101(49):17174-17179. Epub Nov. 29, 2004.
Thompson et al., "Costimulatory molecule B7-H1 in primary and metastatic clear cell renal cell carcinoma," *Cancer*, 104(10):2084-2091, Nov. 15, 2005.
Thompson et al., "PD-1 is expressed by tumor-infiltrating immune cells and is associated with poor outcome for patients with renal cell carcinoma," Clin Cancer Res., 13(6):1757-1761, Mar. 15, 2007.
Thompson et al., "Tumor B7-H1 is associated with poor prognosis in renal cell carcinoma patients with long-term follow-up," Cancer Res., 66(7):3381-3385, Apr. 1, 2006.

(56) References Cited

OTHER PUBLICATIONS

Thompson et al., "Tumor masses support naive T cell infiltration, activation, and differentiation into effectors," J Exp Med., 207(8):1791-1804, Epub Jul. 26, 2010.
Tian et al., "The relationship between the down-regulation of DNA-PKcs or Ku70 and the chemosensitization in human cervical carcinoma cell line HeLa," Oncol Rep., 18(4):927-932, Oct. 2007.
Tiegs et al., "A T cell-dependent experimental liver injury in mice inducible by concanavalin A," J Clin Invest., 90(1):196-203, Jul. 1992.
Titomirov, "In vivo electroporation and stable transformation of skin cells of newborn mice by plasmid DNA," Biochim Biophys Acta., 1088(1):131-134, Jan. 17, 1991.
Todd et al., "Transcription of the interleukin 4 gene is regulated by multiple promoter elements," J Exp Med., 177(6):1663-1674, Jun. 1, 1993.
Topalian et al., "Safety, activity, and immune correlates of anti-PD-1 antibody in cancer," The New England Journal of Medicine., 368(26):2443-2454, Jun. 28, 2012.
Townsend et al., "Tumor rejection after direct costimulation of CD8+ T cells by B7-transfected melanoma cells," Science, 259(5093):368-370, Jan. 15, 1993.
Trabattoni et al. "B7-H1 is up-regulated in HIV infection and is a novel surrogate marker of disease progression" Blood, 101(7):2514-2520, Epub Dec. 5, 2002.
Tringler et al., "B7-h4 is highly expressed in ductal and lobular breast cancer," Clin Cancer Res., 11(5):1842-1848, Mar. 1, 2005.
Truneh et al., "Early steps of lymphocyte activation bypassed by synergy between calcium ionophores and phorbol ester," Nature., 313(6000):318-320, Jan. 24-30, 1985.
Tseng et al., "B7-DC, a new dendritic cell molecule with potent costimulatory properties for T cells," J Exp Med., 193(7):839-846, Apr. 2, 2001.
Ueda et al., "Sequence-specific DNA damage induced by reduced mitomycin C and 7-N-(p-hydroxyphenyl)mitomycin C.," Nucleic Acids Res., 12(17):6673-6683, Sep. 11, 1984.
Verhoeyen et al., "Reshaping human antibodies: grafting an antilysozyme activity," Science, 239(4847):1534-1536, Mar. 25, 1988.
Vesely et al., "Natural innate and adaptive immunity to cancer," Annu Rev Immunol., 29:235-271, 2011.
Veuger et al., "Radiosensitization and DNA repair inhibition by the combined use of novel inhibitors of DNA-dependent protein kinase and poly(ADP-ribose) polymerase-1," Cancer Res., 63(18):6008-6015, Sep. 15, 2003.
Vinay et al., "Role of 4-1BB in immune responses," Semin Immunol., 10(6):481-489, Dec. 1998.
Wahl et al., "Improved radioimaging and tumor localization with monoclonal F(ab')2" J Nucl Med., 24(4):316-25, Apr. 1983.
Walunas et al., "CTLA-4 ligation blocks CD28-dependent T cell activation," J Exp Med., 183(6):2541-2550, Jun. 1, 1996.
Wang et al., "Costimulation of T cells by B7-H2, a B7-like molecule that binds ICOS," Blood, 96(8):2808-2813, Oct. 15, 2000.
Wang et al., "Doxorubicin induces apoptosis in normal and tumor cells via distinctly different mechanisms. intermediacy of H(2)O(2)- and p53-dependent pathways," J Biol Chem., 279(24):25535-25543, Epub Mar. 30, 2004.
Wang et al., "Ligand binding sites of inducible costimulator and high avidity mutants with improved function," J Exp Med., 195(8):1033-1041, Apr. 15, 2002.
Wang et al., "Molecular modeling and functional mapping of B7-H1 and B7-DC uncouple costimulatory function from PD-1 interaction," J Exp Med., 197(9):1083-1091, Epub Apr. 28, 2003.
Wang, "Lyophilization and development of solid protein pharmaceuticals," Int J Pharm, 203(1-2):1-60, Aug. 10, 2000.
Wang, "pH-sensitive immunoliposomes mediate target-cell-specific delivery and controlled expression of a foreign gene in mouse," Proc Natl Acad Sci U S A., 84(22):7851-7855, Nov. 1987.
Ward et al., "Binding activities of a repertoire of single immunoglobulin variable domains secreted from Escherichia coli," Nature, 341(6242):544-546, Oct. 12, 1989.
Webster et al., "Targeting molecular and cellular inhibitory mechanisms for improvement of antitumor memory responses reactivated by tumor cell vaccine," J Immunol., 179(5):2860-2869, Sep. 1, 2007.
Weiss, "Hot Prospect for New Gene Amplifier: Ligase chain reaction, a combination DNA amplifier and genetic screen could do for DNA diagnostics what PCR has done for basic molecular biology," Science, 254(5036):1292-1293, Nov. 29, 1991.
Wherry et al., "Lineage relationship and protective immunity of memory CD8 T cell subsets," Nat Immunol., 4(3):225-234, Epub Feb. 3, 2003.
Wick et al., "The hepatic immune system," Crit Rev Immunol., 22(1):47-103, 2002.
Wilcox et al., "Provision of antigen and CD137 signaling breaks immunological ignorance, promoting regression of poorly immunogenic tumors," J Clin Invest., 109(5):651-659, Mar. 2002.
Williams et al., "Introduction of foreign genes into tissues of living mice by DNA-coated microprojectiles," Proc Natl Acad Sci U S A., 88(7):2726-2730, Apr. 1, 1991.
Williams et al., "The immunoglobulin superfamily—domains for cell surface recognition," Annu Rev Immunol., 6:381-405, 1988.
Williams et al., "Nitric oxide synthase plays a signaling role in TCR-triggered apoptotic death," J Immunol., 161(12):6526-6531, Dec. 15, 1998.
Willmore et al., "A novel DNA-dependent protein kinase inhibitor, NU7026, potentiates the cytotoxicity of topoisomerase II poisons used in the treatment of leukemia," Blood, 103(12):4659-4665, Epub Mar. 9, 2004.
Winter et al., "Man-made antibodies," Nature, 349(6307):293-299, Jan. 24, 1991.
Winter et al., "Making antibodies by phage display technology," Annu Rev Immunol., 12:433-455, 1994.
Wintterle et al., "Expression of the B7-related molecule B7-H1 by glioma cells: a potential mechanism of immune paralysis," Cancer Res., 63(21):7462-7467, Nov. 1, 2003.
Wofsy et al., "The proliferating cells in autoimmune MRL/lpr mice lack L3T4, an antigen on "helper" T cells that is involved in the response to class II major histocompatibility antigens," J Immunol., 132(6):2686-2689, Jun. 1984.
Wofsy, "Treatment of murine lupus with anti-CD4 monoclonal antibodies," Immunol Ser., 59:221-236, 1993.
Wolff, "Direct gene transfer into mouse muscle in vivo," Science, 247(4949 Pt 1):1465-1468, Mar. 23, 1990.
Wong et al., "Human GM-CSF: molecular cloning of the complementary DNA and purification of the natural and recombinant proteins," Science, 228(4701):810-815, May 17, 1985.
Wu et al., The double-edged sword of activation-induced cytidine deaminase, J Immunol., 174(2):934-941, Jan. 15, 2005.
Wu, "Receptor-mediated gene delivery and expression in vivo," J Biol Chem., 263(29):14621-14624, Oct. 15, 1988.
Wu, "Targeting genes: delivery and persistent expression of a foreign gene driven by mammalian regulatory elements in vivo," J Biol Chem., 264(29):16985-16987, Oct. 15, 1989.
Xu et al., "A potential new pathway for PD-L1 costimulation of the CD8-T cell response to Listeria monocytogenes infection," PLoS One, 8(2):e56539, Epub Feb. 11, 2013.
Xu et al., "The inducible expression of the tumor suppressor gene PTEN promotes apoptosis and decreases cell size by inhibiting the PI3K/Akt pathway in Jurkat T cells," Cell Growth Differ., 13(7):285-296, Jul. 2002.
Yamamoto et al., "B7-H1 expression is regulated by MEK/ERK signaling pathway in anaplastic large cell lymphoma and Hodgkin lymphoma," Cancer Sci., 100(11):2093-2100, Epub Aug. 1, 2009.
Yamazaki et al., "Expression of programmed death 1 ligands by murine T cells and APC," J Immunol., 169(10):5538-5545, Nov. 15, 2002.
Yang et al., "In vitro priming of tumor-reactive cytolytic T lymphocytes by combining IL-10 with B7-CD28 costimulation," J Immunol., 155(8):3897-3903, Oct. 15, 1995.
Yang et al., "In vivo and in vitro gene transfer to mammalian somatic cells by particle bombardment," Proc Natl Acad Sci U S A., 87(24):9568-9572, Dec. 1990.

(56) References Cited

OTHER PUBLICATIONS

Yang, "Gene transfer into mammalian somatic cells in vivo," *Crit Rev Biotechnol.*, 12(4):335-356, 1992.

Yoshinaga et al., "T-cell co-stimulation through B7RP-1 and ICOS," *Nature*, 402(6763):827-832, Dec. 16, 1999.

Yotsumoto et al., "Endosomal translocation of CpG-oligodeoxynucleotides inhibits DNA-PKcs-dependent IL-10 production in macrophages," *J Immunol.*, 180(2):809-816, Jan. 15, 2008.

Youngnak et al., "Differential binding properties of B7-H1 and B7-DC to programmed death-1," *Biochem Biophys Res Commun.*, 307(3):672-677, Aug. 1, 2003.

Yuan et al., "Focus on histone variant H2AX: to be or not to b," *FEBS Lett.*, 584(17):3717-3724, Epub May 21, 2010.

Zang et al., "B7X: a widely expressed b7 family member that inhibits T cell activation," *Proc Natl Acad Sci U S A.*, 100(18):10388-10392, Epub Aug. 14, 2003.

Zang et al., "The B7 family and cancer therapy: costimulation and coinhibition," *Clin Cancer Res.*, 13(18 Pt 1):5271-5279, Sep. 15, 2007.

Zelenin et al., "Genetic transformation of mouse cultured cells with the help of high-velocity mechanical DNA injection," *FEBS Lett.*, 244(1):65-67, Feb. 13, 1989.

Zelenin et al., "High-velocity mechanical DNA transfer of the chloramphenicolacetyl transferase gene into rodent liver, kidney and mammary gland cells in organ explants and in vivo," *FEBS Lett.*, 280(1):94-96, Mar. 11, 1991.

Zhang et al., "PD-1/PD-L1 interactions inhibit antitumor immune responses in a murine acute myeloid leukemia model," *Blood*, 114(8):1545-1552, Epub May 5, 2009.

Zhang et al., "Theiler's Virus-infected L-selectin-deficient mice have decreased infiltration of CD8(+) T lymphocytes in central nervous system but clear the virus," *J Neuroimmunol.*, 116(2):178-187, Jun. 1, 2001.

Zhou et al., "Inducible-costimulator-mediated suppression of human immunodeficiency Virus type 1 replication in CD4+ T lymphocytes," *Virology*, 325(2):252-263, Aug. 1, 2004.

Zou et al., "Inhibitory B7-family molecules in the tumour microenvironment," *Nat Rev Immunol.*, 8(6):467-477, Jun. 2008.

Zula et al., "The role of cell type-specific responses in IFN-β therapy of multiple sclerosis," *Proc Natl Acad Sci U S A.*, 108(49):19689-19694, Epub Nov. 21, 2011.

Zumla et al. "Granulomatous infections: etiology and classification," *Clin Infect Dis.*, 23(1):146-158, Jul. 1996.

Zwiebel et al., "Drug delivery by genetically engineered cell implants," *Ann N Y Acad Sci.*, 618:394-404, 1991.

FIG. 12

```
  1 atgaggatat ttgctgtctt tatattcatg acctactggc atttgctgaa cgcattact
 61 gtcacggttc ccaaggacct atatgtggta gagtatggta gcaatatgac aattgaatgc
121 aaattcccag tagaaaaaca attagacctg gctgcactaa ttgtctattg ggaatggag
181 gataagaaca ttattcaatt tgtgcatgga gaggaagacc tgaaggttca gcatagtagc
241 tacagacaga gggcccggct gttgaaggac cagctctccc tgggaaatgc tgcacttcag
301 atcacagatg tgaaattgca ggatgcaggg gtgtaccgct gcatgatcag ctatgtggt
361 gccgactaca agcgaattac tgtgaaagtc aatgccccat acaacaaaat caaccaaaga
421 atttggttg tggatccagt caccctgaa catgaactga catgtcaggc tgagggctac
481 cccaaggccg aagtcatctg gacaagcagt gaccatcaag tcctgagtgg taagaccacc
541 accaccaatt ccaagagaga ggagaagctt ttcaatgtga ccagcacact gagaatcaac
601 acaacaacta atgagatttt ctactgcact tttaggagat ctggcacatc ctccaaatga ggaaaaccat
661 acagctgaat tggtcatccc agaactacct cttggtgtag cactgacatt catcttccgt
721 ttggtaattc tgggagccat cttattatgc cttggtgtag cactgacatt catcttccgt
781 ttaagaaaag ggagaatgat ggatgtgaaa aatgtggca tccaagatac aaactcaaag
841 aagcaaagtg atacacattt ggaggagacg taa (SEQ ID NO:14)

1 MRIFAVFIFM TYWHLLNAFT VTVPKDLYVV EYGSNMTIEC KFPVEKQLDL AALIVYWEME
 61 DKNIIQFVHG EEDLKVQHSS YRQRARLLKD QLSLGNAALQ ITDVKLQDAG VYRCMISYGG
121 ADYKRITVKV NAPYNKINQR ILVVDPVTSE HELTCQAEGY PKAEVIWTSS DHQVLSGKTT
181 TTNSKREEKL FNVTSTLRIN TTTNEIFYCT FRRLDPEENH TAELVIPELP LAHPPNERTH
241 LVILGAILLC LGVALTFIFR LRKGRMMDVK KCGIQDTNSK KQSDTHLEET (SEQ ID NO:15)
```

FIG. 13

```
  1 gcctgagcag tggagaaggc ggcactctgg tgggctgct ccaggcatgc agatcccaca
 61 ggcgccctgg ccagtcgtct gggcggtgct acaactgggc tgcggccag gatgttctt
121 agactcccca gacaggccct gaaccccc ccttctcc ccagcccct tcgtggtgac
181 cgaaggggac aacgccacct tcacctgcag cttctccaac acatcggaga gcttcgtgct
241 aaactggtac cgcatgagcc ccagcaacca gacgacaag ctggccgctt tccccgagga
301 ccgcagccag cccggccagg actgccgctt ccgtgtcaca caactgccca acgggcgtga
361 cttccacatg agcgtggtca gggcccggc caatgacagc ggcacctacc tctgtgggc
421 catctccctg gcccccaagg cgcagatcaa agagagcctg cgggcagagc tcagggtgac
481 agagagaagg gcagaagtgc ccacagccca cccagcccc tcacccaggc cagccggcca
541 gttccaaacc ctggtggttg gtgtcgtggg cgtgtcgtgg ggcagcctgg tgctgctagt
601 ctgggtcctg gccgtcatct gctcccggc acgagagg acaataggag ccaggcgcac
661 cggccagccc ctgaaggagg cccctcagc cgtgcctgtg ttctctgtgg actatgggga
721 gctggatttc cagtggcgag agaagaccc ggagccccc gtgcctgtg tccctgagca
781 gacggagtat gccaccattg tcttttcctag cggaatgggc acctcatccc ccgcccag
841 gggctcagcc gacggccctc ggagtgccca gccactgagg gccactgagg gacactgctc
901 ttggccctc tgaccggctc ccttggccac cagtgttctg cagaccct (SEQ ID NO:16)
```

```
  1 MQIPQAPWPV VWAVLQLGWR PGWFLDSPDR PWNPPTFSPA LLVVTEGDNA TFTCSFSNTS
 61 ESFVLNWYRM SPSNQTDKLA AFPEDRSQPG QDCRFRVTQL PNGRDFHMSV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO:17)
```

FIG. 14A

```
   1 gacaagtact gagtgaactc aaaccctctg taaagtaaca gaagttagaa gggaaatgt cgcctctctg aagattaccc
  81 aaagaaaaag tgatttgtca ttgctttata gactgtaaga agagaacatc tcagaagtgg agtcttaccc tgaaatcaaa
 161 ggatttaaag aaaaagtgga attttcttc agcaagctgt gaaactaaat ccacaaccct tggagaccca ggaacaccct
 241 ccaatctctg tgtgttttgt aaacatcact ggagggtctt ctacgtgagc aattggattg tcatcagccc tgcctgtttt
 321 gcacctggga agtgccctgg tcttacttgg gtccaaattg ttggcttca ctttgaccc taagcatctg aagccatggg
 401 ccacacacgg aggcaggaa catcaccatc caagtgtcca tacctcaatt tcttcagct ctggtgctg gctggtcttt
 481 ctcacttctg ttcaggtgtt atccacgtga ccaaggaagt gaaagaagtg gcaacgctgt cctgtggtca caatgtttct
 561 gttgaagagc tggcacaaac tcgcatctac tggcaaaagg agaagaaaat ggtgctgact atgatgtctg gggacatgaa
 641 tatatggccc gagtacaaga accggaccat ctttgatatc actaataacc tctccattgt gatcctggct ctgcgcccat
 721 ctgacgaggg cacatacgag tgtgttgttc tgaagtatga aaaagacgct ttcaagcggg aacacctggc tgaagtgacg
 801 ttatcagtca aagctgactt ccctacacct agtatatctg actttgaaat tccaacttct aatattagaa ggataatttg
 881 ctcaacctct ggaggttttc cagagcctca cctctcctgg ttgaaaatg gagaagaatt aaatgccatc aacacaacag
 961 tttcccaaga tcctgaaact gagctctatg ctgttagcag caaactgat ttcaatatga caaccaacca cagcttcatg
1041 tgtctcatca agtatgaca tttaagagtg aatcagacct tcaactgaa tacaaccaag caagagcatt ttcctgataa
1121 cctgctccca tcctgggcca ttacttaaat ctcagtaaat ggaattttg tgatatgct cctgacctac tgctttgccc
1201 caagatgcag agagagaagg aggaatgaga gattgagaag ggaaagtgta cgccctgtat aacagtgtcc gcaagaagcaa
1281 gggctgaaa agatctgaag gtcccacctc catttgcaat tgacctcttc tgggaacttc ctcagatgga caagattacc
1361 ccaccttgcc ctttacgtat ctgctcttag gtgcttcttc acttcagttg ctttgcagga agtgctaga ggaatatggt
1441 gggcacagaa gtagctctgg tgaccttgat caaggtgttt caaggtgact gaaatgcag aattcttgag ttctggaagg gacttagag
1521 aataccagtg ttattaatga caaggcact gaggccagg gaggtgaccc gaattataa gccagcgcc agaaccaga
1601 tttctaact ctggtgctct ttcccttat ttgtccaata cagttgact gtgcctgtt aactggtata tacatatata tgtcaggcaa
1681 agtgctgctg gaagtagaat ttgtccaata agcccaatgt ttcagagact aagtatggca ttcgatttc ctaatgtcag agtagaagat
1761 tttatgctgc tgtttacaaa tcccagtat tccatttttt tcattgtgtt ctctattgct tgaacatctt taggagacta atgaaatat
1841 tattggtgtt tacccagtat tatccaaac taattcctc tgacatgtaa gacgaatgat ttaggtacgt caaagcagta ggtacagcag
1921 aaaggagaac tatccaaaac taactggttc atattggact gataatctct ttaaatggct ttatgctagt gtcaaggagg
2001 aaaggatag tccaaagact agtctcatt taaatgaga tcgttgttta cagtgtatgt ttgacctcat
2081 ttgtaaaata tttatgaaa tttccatagg gctccttag atccctaaga tggctttttc actaagcagt aagctatctt
2161 caaatgtcta agtagtaac tttcatagg gctccttag atccctaaga tggctttttc tccttgtat ttctggtctt
2241 ttctgacatc agcagagaac tgaaaagaca tagcaactg ctgttcatgt tactcatgac tcctttctct aaaactgcct
2321 tccacaattc actagaccag aagtggacgc aacttaagct gggataatca cattatcatc tgaaaatctg gagttgaaca
2401 gcaaagaag acaacatttc tcaaatgcac atctcatggc agctaagcca catggctggg atttaaagcc tttagagcca
2481 gcccatggct ttagctacct cactatgctg cttcacaaac cttgctcctg tgtaaaacta tattctcagt gtagggcaga
2561 gaggtctaac accaacataa ggtactagca gtgtttcccg tattgacagg aatacttaac tcaataattc tttttcttttc
2641 cattagtaa cagttgtgat gactatgttt ctattcctaa taattcctgt attctacagc agatactttg tcagcaatac
2721 taagggaaga aacaaagttg aaccgttttct ttaataa (SEQ ID NO:18)
```

FIG. 14B

```
  1 MGHTRRQGTS PSKCPYLNFF QLLVLAGLSH FCSGVIHVTK EVKEVATLSC GHNVSVEELA
 61 QTRIYWQKEK KMVLTMMSGD MNIWPEYKNR TIFDITNNLS IVILALRPSD EGTYECVVLK
121 YEKDAFKREH LAEVTLSVKA DFPTPSISDF EIPTSNIRRI ICSTSGGFPE PHLSWLENGE
181 ELNAINTTVS QDPETELYAV SSKLDFNMTT NHSFMCLIKY GHLRVNQTFN WNTTKQEHFP
241 DNLLPSWAIT LISVNGIFVI CCLTYCFAPR CRERRRNERL RRESVRPV (SEQ ID NO:19)
```

TARGETING DNA-PKCS AND B7-H1 TO TREAT CANCER

CROSS-REFERENCE TO RELATED APPLICATIONS

This application is a National Stage application under 35 U.S.C. § 371 of International Application No. PCT/US2015/032016 having an International Filing Date of May 21, 2015, which claims benefit of priority from U.S. Provisional Application No. 62/027,841, filed on Jul. 23, 2014.

TECHNICAL FIELD

This document relates to materials and methods for treating potentially chemoresistant tumors, and particularly to materials and methods for treating such tumors with DNA-PKcs inhibitors.

BACKGROUND

The development of resistance to chemotherapy and immunotherapy is a major obstacle in prolonging survival of cancer patients. The emergence of chemoresistance and immunoresistance were traditionally viewed as parallel and unrelated events, but more recent evidence indicates that overexpression of some immune checkpoint molecules may negatively influence antitumor immunity and also render tumor cells resistant to chemotherapeutic agents (Tamura et al., Leukemia: Official Journal of the Leukemia Society of America, Leukemia Research Fund, UK 27:464-472, 2013; Ghebeh et al., Breast Cancer Res 12:R48, 2010; and Liu et al., Molecular Cancer Ther 10:960-971, 2011).

SUMMARY

Cancer therapies using checkpoint blockades can blunt the immune-suppressive function of ligands (e.g., B7-H1 on tumor cells) by blocking interaction with their receptors (e.g., PD-1 on T cells) (Zang and Allison, Clin Cancer Res 13:5271-5279, 2007; and Dong and Chen, J Mol Med 81:281-287, 2003). While such therapies can contribute to enhanced antitumor immunity, blocking the binding of B7-H1 to PD-1 may not overcome B7-H1-mediated chemoresistance.

The therapeutic methods described herein can be used to target B7-H1's intrinsic signaling pathway in relation to chemoresistance. These methods are based on the results of experiments that elucidated a molecular mechanism underlying B7-H1-mediated tumor chemoresistance, as described below, thus providing new therapeutic targets to defuse this mechanism. For example, this document is based at least in part on the discovery that DNA-PKcs is a B7-H1 binding protein, and that DNA-PKcs can be targeted to reduce B7-H1-mediated chemoresistance. This discovery was unexpected, as DNA-PKcs is a nuclear protein involved in DNA damage repair (Collis et al., Oncogene 24:949-961, 2005), while B7-H1 is an immunoregulatory molecule mainly expressed on the cell surface of tumor cells (Dong et al., Nat Med 8:793-800, 2002).

In one aspect, this document features a method for treating a cancer patient. The method can include (a) identifying a cancer patient to be treated with a chemotherapeutic agent that causes DNA damage, (b) administering to the patient a molecule targeted to DNA-PKcs, wherein the molecule is administered in an amount sufficient to reduce the interaction of DNA-PKcs with B7-H1, and (c) administering the chemotherapeutic agent to the patient. The patient can be a human. The chemotherapeutic agent can be cisplatin, doxorubicin, SN38, paclitaxel, protein-bound paclitaxel, temozolomide, or carboplatin. The molecule targeted to DNA-PKcs can be NU7026, NU7441, IC86621, IC87102, IC87361, OK-1035, SU11752, vanillin, or IC486241, or can be an anti-DNA-PKcs antibody. The molecule targeted to DNA-PKcs and the chemotherapeutic agent can be administered simultaneously or sequentially.

In another aspect, this document features a method for treating a cancer patient, where the method can include (a) identifying the patient as having a tumor with cells that express B7-H1, and (b) administering to the patient a DNA-PKcs inhibitor and an anti-B7-H1 blocking antibody. The cancer patient can be a human. The cancer patient can be identified based on the level of B7-H1 protein in a sample obtained from the tumor, or based on the level of B7-H1 mRNA in a sample obtained from the tumor. The cancer can be a melanoma cancer, a breast cancer, a lung cancer, a renal cell carcinoma cancer, a pancreas cancer, a prostate cancer, a colon cancer, a brain cancer, a liver cancer, or an ovarian cancer. The DNA-PKcs inhibitor and the anti-B7-H1 blocking antibody can be administered to the cancer patient simultaneously or sequentially.

In another aspect, this document features a method for treating cancer, where the method can include administering a DNA-PKcs inhibitor and an anti-B7-H1 antibody to a mammal identified as having a tumor containing cells with an elevated level of B7-H1, where the DNA-PKcs inhibitor and the anti-B7-H1 antibody are administered under conditions in which the interaction of naturally-occurring B7-H1 with DNA-PKcs and the interaction of naturally-occurring B7-H1 with PD-1 or CD80 in the mammal is reduced after the administering. The mammal can be a human. The elevated level B7-H1 can be based on the level of B7-H1 protein in a sample obtained from the tumor, or based on the level of B7-H1 mRNA in a sample obtained from the tumor. The cancer can be a melanoma cancer, a breast cancer, a lung cancer, a renal cell carcinoma cancer, a pancreas cancer, a prostate cancer, a colon cancer, a brain cancer, a liver cancer, or an ovarian cancer. The DNA-PKcs inhibitor and the anti-B7-H1 blocking antibody can be administered to the mammal simultaneously or sequentially.

In still another aspect, this document features a composition containing a pharmaceutically acceptable carrier and a molecule targeted to DNA-PKcs for use in treating a cancer patient who also is to be treated with a chemotherapeutic agent that causes DNA damage, wherein the composition is to be administered in an amount sufficient to reduce the interaction of DNA-PKcs with B7-H1. The patient can be a human. The chemotherapeutic agent can be cisplatin, doxorubicin, SN38, paclitaxel, protein-bound paclitaxel, temozolomide, or carboplatin. The molecule targeted to DNA-PKcs can be NU7026, NU7441, IC86621, IC87102, IC87361, OK-1035, SU11752, vanillin, or IC486241, or can be an anti-DNA-PKcs antibody. The chemotherapeutic agent and the composition containing the molecule targeted to DNA-PKcs can be for simultaneous or sequential administration.

In another aspect, this document features a composition containing a pharmaceutically acceptable carrier and a DNA-PKcs inhibitor for use in treating cancer in a patient identified as having a tumor with cells that express B7-H1, wherein the patient also is to be treated with an anti-B7-H1 blocking antibody. The cancer patient can be a human. The cancer patient can be identified based on the level of B7-H1 protein in a sample obtained from the tumor, or based on the level of B7-H1 mRNA in a sample obtained from the tumor. The cancer can be a melanoma cancer, a breast cancer, a lung cancer, a renal cell carcinoma cancer, a pancreas cancer, a prostate cancer, a colon cancer, a brain cancer, a liver cancer, or an ovarian cancer. The anti-B7-H1 blocking antibody and the composition containing the DNA-PKcs inhibitor can be for simultaneous or sequential administration.

In still another aspect, this document features a composition containing a pharmaceutically acceptable carrier and a DNA-PKcs inhibitor for use in treating cancer in a mammal identified as having a tumor containing cells with an elevated level of B7-H1, wherein the mammal also is to be treated with an anti-B7-H1 antibody, and wherein the composition containing the DNA-PKcs inhibitor and the anti-B7-H1 antibody are to be administered under conditions in which the interaction of naturally-occurring B7-H1 with DNA-PKcs and the interaction of naturally-occurring B7-H1 with PD-1 or CD80 in the mammal are reduced after the administering. The mammal can be a human. The elevated level B7-H1 can be based on the level of B7-H1 protein in a sample obtained from the tumor, or based on the level of B7-H1 mRNA in a sample obtained from the tumor. The cancer can be a melanoma cancer, a breast cancer, a lung cancer, a renal cell carcinoma cancer, a pancreas cancer, a prostate cancer, a colon cancer, a brain cancer, a liver cancer, or an ovarian cancer. The anti-B7-H1 blocking antibody and the composition containing the DNA-PKcs inhibitor can be for simultaneous or sequential administration.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a series of graphs plotting relative survival of Mock/624mel (triangles) and B7-H1/624mel (squares) cells treated with the indicated drugs, as determined by MTS (3-(4,5-dimethylthiazol-2-yl)-5-(3-carboxymethoxyphenyl)-2-(4-sulfophenyl)-2H-tetrazolium) assay. The p-value for area under the curve (dose-response curves) was significant (p<0.01) for treatment with cisplatin (left), doxorubicin (center), and SN38 (right). One of three experiments is shown. Apoptosis of tumor cells treated with doxorubicin (1.5 ug/ml, 48 hr.) was analyzed by tetramethylrhodamine ethyl ester (TMRE) and Annexin V staining (FIG. 1B), and by intracellular staining for active caspase-3 (FIG. 1C). Numbers are percentages of gated population.

FIG. 2A: Anti-B7-H1 Ab, but not control Ab, co-precipitated a protein band in B7-H1 transfected 624mel cells. FIG. 2B: Co-immunoprecipitation (IP) and Western blotting (WB) using cell lysate as input. FIG. 2C: Human primary T cells were activated by phytohemagglutinin (PHA) for 48 hours. B7-H1 was pulled down by anti-B7-H1 antibody but not control antibody. The association of B7-H1 with DNA-PKcs was detected by Western blotting using anti-DNA-PKcs antibody.

FIG. 8A is a picture (top) and a graph (bottom) showing the results of an antibody array assay of phosphorylation of molecules in the MAPK/ERK pathway. The levels of phospho-ERK and total ERK were analyzed by Western blotting (FIG. 8B) and flow cytometry (FIG. 8C). Numbers are mean fluorescence intensity (MFI).

FIG. 12 contains representative nucleic acid (top) and amino acid (bottom) sequences for human B7-H1 (SEQ ID NOS:14 and 15, respectively).

FIG. 13 contains representative nucleic acid (top) and amino acid (bottom) sequences for human PD-1 (SEQ ID NOS:16 and 17, respectively).

FIGS. 14A and 14B contain representative nucleic acid (14A) and amino acid (14B) sequences for human CD80 (SEQ ID NOS:18 and 19, respectively).

FIG. 15A shows an immuno-precipitation assay, demonstrating that NU7026 abolished the association of B7-H1 with DNA-PKcs. FIG. 15B is a series of pictures from an immunofluorescence assay in which the cells treated with doxorubicin, NU7026, or both, and stained for DNA-PKcs, DNA, or B7-H1. Doxorubicin-induced co-localization (arrow, upper right panel) of B7-H1 and DNA-PKcs at the nucleus was blocked by NU7026 (lower right panel).

DETAILED DESCRIPTION

Figure 1:
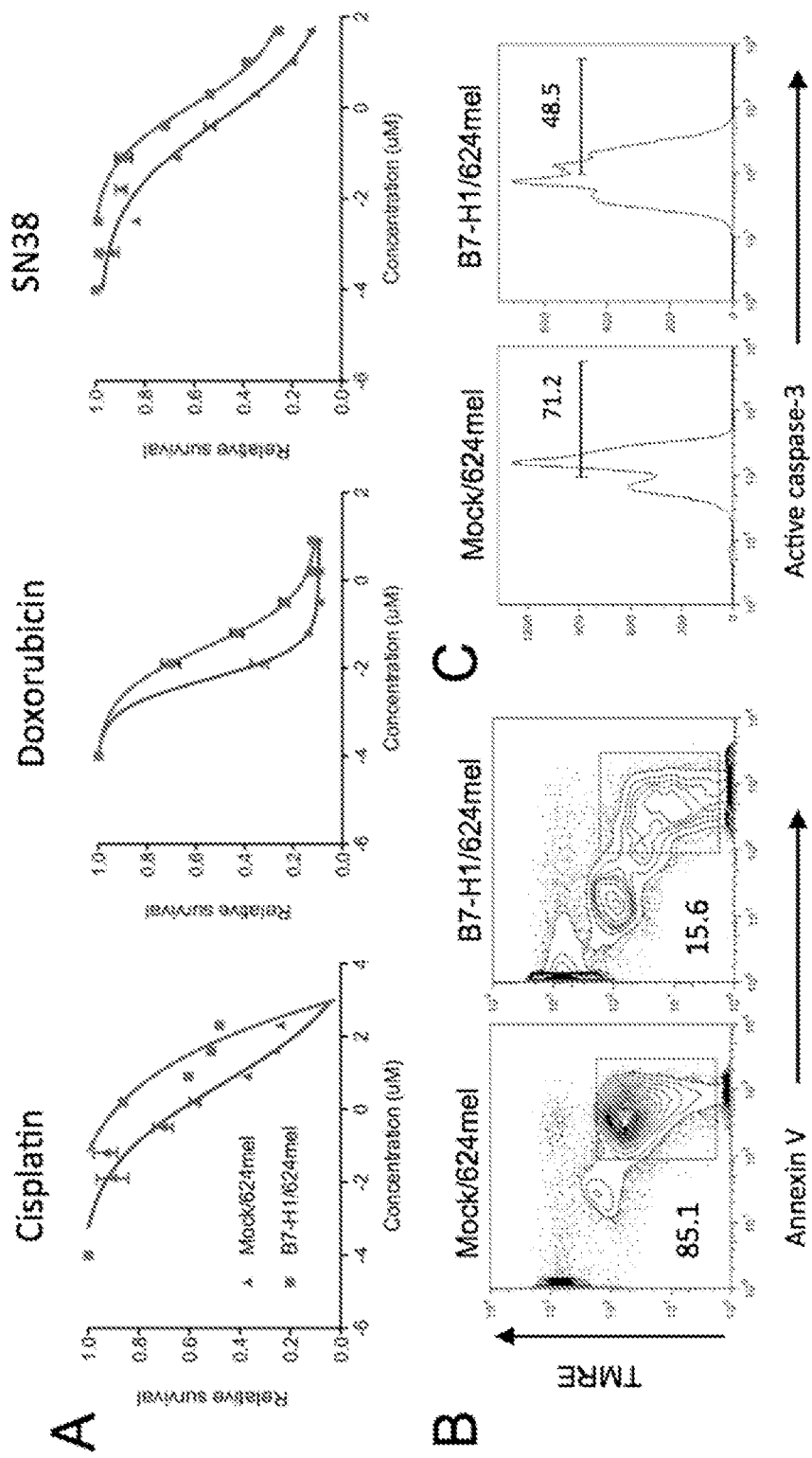
FIGS. 1A-1C demonstrate that B7-H1 confers tumor cell resistance to cytotoxic drugs.

This document provides methods and materials for treating cancer in patients with tumors that are chemoresistant or are at risk of becoming chemoresistant. For example, this document provides methods and materials for identifying a cancer patient (e.g., a mammal such as a human, non-human primate, cow, sheep, pig, dog, rabbit, rat, or mouse) as having a tumor that expresses B7-H1 at an elevated level, and treating the patient with a molecule that can interfere with the interaction between B7-H1 and DNA-PKcs. In some embodiments, the methods provided herein also can include treating the patient with a molecule that can interfere with the interaction between B7-H1 and PD-1, and/or the interaction between B7-H1 and CD80 (e.g., an antibody against B7-H1, PD-1, or CD80, or a fusion protein containing a portion of PD-1 or a portion of CD80 fused to an immunoglobulin (Ig) Fc domain).

The term "elevated level" as used herein with respect to a level of B7-H1 refers to a level that is greater (e.g., 50% greater, 2-fold greater, 3-fold greater, or more than 3-fold greater) than a reference level of B7-H1. The term "reference level" as used herein with respect to B7-H1 can refer to the level of B7-H1 typically observed in cells from healthy subjects without cancer. In some embodiments, for example, a reference level of B7-H1 can be the average level of B7-H1 present in samples obtained from a random sampling of 50 humans free of cancer. In some embodiments, B7-H1 levels can be determined based on cell staining, and "elevated" and "reference" levels can set based on the percentage of evaluated cells that stain positive for B7-H1. For example, in some embodiments, samples (e.g., tumor samples) in which five percent or less (e.g., five percent, four percent, three percent, two percent, one percent, or less than one percent) of the cells stain positive for B7-H1 can be considered B7-H1 negative. In some embodiments, samples (e.g., tumor samples) in which ten percent or more (e.g., ten percent, 20 percent, 25 percent, 30 percent, 40 percent, 50 percent, or more than 50 percent) of the cells stain positive for B7-H1 can be considered to have elevated levels of B7-H1 expression.

The presence of an elevated level of B7-H1 can be determined by measuring, for example, B7-H1 protein levels or B7-H1 nucleic acid levels. For example, the level of B7-H1 protein can be measured in a tumor sample from a mammal with cancer using cell staining, western blotting, or other immunological techniques. The level of B7-H1 expression also can be measured at the nucleic acid level, using Northern blotting, or any other method suitable for determining mRNA levels of CD274, which encodes the B7-H1 protein. In some cases, B7-H1 protein or nucleic acid levels can be measured in ascites samples, or lymphoid organ samples. It will be appreciated that levels from comparable samples are used when determining whether or not a particular level is an elevated level.

A representative example of a human B7-H1 nucleic acid has the sequence set forth in GENBANK® Accession No. AF177937 (GI No. 6708118) (SEQ ID NO:14; FIG. 12), and a representative human B7-H1 polypeptide has the sequence set forth in GENBANK® Accession No. AAF25807 (GI No. 6708119) (SEQ ID NO:15; FIG. 12).

A representative example of a human PD-1 nucleic acid can have the sequence set forth in GENBANK® Accession No. BC074740.2 (GI No. 50960296) (SEQ ID NO:16; FIG. 13), and representative example of a human PD-1 polypeptide has the sequence set forth in GENBANK® Accession No. AAH74740.1 (GI No. 49902307) (SEQ ID NO:17; FIG. 13).

A representative example of a human CD80 nucleic acid has the sequence set forth in NCBI Reference No. NM_005191.3 (GI No. 113722122) (SEQ ID NO:18; FIG. 14A), and a representative example of a human CD80 polypeptide has the sequence set forth in NCBI Reference No. NP_005182.1 (GI No. 4885123) (SEQ ID NO:19; FIG. 14B).

After the level of B7-H1 within a tumor sample from a mammal is determined, the level can be compared to a reference level, and the mammal can be classified as having or not having an elevated level of B7-H1. If the mammal is identified as having an elevated level of B7-H1, the mammal can be treated with a first molecule that inhibits the interaction between B7-H1 and DNA-PKcs. For example, a small molecule DNA-PKcs inhibitor such as NU7026, NU7441, IC86621, IC87102, IC87361, OK-1035, SU11752, vanillin, or IC486241 can be administered to the mammal. For the structures of these molecules, see, e.g., Davidson et al., *Front Pharmacol* 4:1-7, 2013. In some embodiments, an anti-DNA-PKcs antibody can be administered to block the interaction between B7-H1 and DNA-PKcs. Further, B7-H1 peptides can be useful. Such peptides can be fragments of B7-H1 (e.g., fragments containing about 10-20, about 20-50, or about 50-100 amino acids) that include the DNA-PKcs binding domain, such that they can inhibit the interaction between B7-H1 and DNA-PKcs. Such peptides can be referred to as "interfering B7-H1 small peptides."

In some embodiments, the mammal also can be treated with a second molecule that inhibits the interaction between B7-H1 and PD-1 and/or the interaction between B7-H1 and CD80. Examples of such second molecules include, without limitation, antibodies (e.g., anti-B7-H1 antibodies, anti-PD-1 antibodies, or anti-CD80 antibodies), and fusion proteins (e.g., PD-1 fusion proteins or CD80 fusion proteins). Such fusion proteins can contain, for example, the extracellular domain of PD-1 fused to an IgG Fc domain, or the extracellular domain of CD80 fused to an IgG Fc domain. Binding of the fusion proteins to B7-H1 can reduce or block the ability of B7-H1 to interact with PD-1 and/or CD80.

The term "antibody" includes monoclonal antibodies, polyclonal antibodies, recombinant antibodies, humanized antibodies (Jones et al. (1986) *Nature* 321:522-525; Riechmann et al. (1988) *Nature* 332:323-329; and Presta (1992) *Curr. Op. Struct. Biol.* 2:593-596), chimeric antibodies (Morrison et al. (1984) *Proc. Natl. Acad. Sci. USA* 81:6851-6855), multispecific antibodies (e.g., bispecific antibodies) formed from at least two antibodies, and antibody fragments. The term "antibody fragment" comprises any portion of the afore-mentioned antibodies, such as their antigen binding or variable regions. Examples of antibody fragments include Fab fragments, Fab' fragments, F(ab')2 fragments, Fv fragments, diabodies (Hollinger et al. (1993) *Proc. Natl. Acad. Sci. USA* 90:6444-6448), single chain antibody molecules (Plückthun in: *The Pharmacology of Monoclonal Antibodies* 113, Rosenburg and Moore, eds., Springer Verlag, N.Y. (1994), 269-315) and other fragments as long as they exhibit the desired capability of binding to their target (e.g., B7-H1, PD-1, or CD80).

Examples of anti-human B7-H1 antibodies include, without limitation, anti-human B7-H1 antibodies commercially available from Biolegend (e.g., Catalog No. 329701 or 329702; San Diego, Calif.) or eBioscience (e.g., Catalog No. 14-5983-80 or 14-5983-82).

Examples of anti-human PD-1 antibodies include, without limitation, anti-human PD-1 antibodies commercially available from Biolegend (e.g., Catalog No. 329904 or 329905) or eBioscience (Catalog No. 12-2799-42; San Diego, Calif.).

Examples of anti-human CD80 antibodies include, without limitation, anti-human CD8 antibodies commercially available from Biolegend (e.g., Catalog No. 305201 or 305202) or eBioscience (e.g., Catalog No. 14-0809-80 or 14-0809-82).

The term "antibody," as used herein, also includes antibody-like molecules that contain engineered sub-domains of antibodies or naturally occurring antibody variants. These antibody-like molecules may be single-domain antibodies such as $V_H$-only or $V_L$-only domains derived either from natural sources such as camelids (Muyldermans et al. (2001) *Rev. Mol. Biotechnol.* 74:277-302) or through in vitro display of libraries from humans, camelids or other species (Holt et al. (2003) *Trends Biotechnol.* 21:484-90). In certain embodiments, the polypeptide structure of the antigen binding proteins can be based on antibodies, including, but not limited to, minibodies, synthetic antibodies (sometimes referred to as "antibody mimetics"), human antibodies, antibody fusions (sometimes referred to as "antibody conjugates"), and fragments thereof, respectively.

An "Fv fragment" is the minimum antibody fragment that contains a complete antigen-recognition and -binding site. This region consists of a dimer of one heavy chain variable domain and one light chain variable domain in tight, non-covalent association. It is in this configuration that the three CDR's of each variable domain interact to define an antigen-binding site on the surface of the VH-VL dimer. Collectively, the six CDR's confer antigen-binding specificity to the antibody. However, even a single variable domain (or half of an Fv comprising only three CDR's specific for an antigen) has the ability to recognize and bind the antigen, although usually at a lower affinity than the entire binding site. The "Fab fragment" also contains the constant domain of the light chain and the first constant domain ($C_H1$) of the heavy chain. The "Fab fragment" differs from the "Fab' fragment" by the addition of a few residues at the carboxy terminus of the heavy chain $C_H1$ domain, including one or more cysteines from the antibody hinge region. The "F(ab')2 fragment" originally is produced as a pair of "Fab' fragments" which have hinge cysteines between them. Methods of preparing such antibody fragments, such as papain or pepsin digestion, are known to those skilled in the art.

An antibody can be of the IgA-, IgD-, IgE, IgG- or IgM-type, including IgG- or IgM-types such as, without limitation, IgG1-, IgG2-, IgG3-, IgG4-, IgM1- and IgM2-types. For example, in some cases, an antibody can be of the IgG1-, IgG2- or IgG4-type.

In some embodiments, antibodies as used in the methods described herein can be fully human or humanized antibodies. Human antibodies can avoid certain problems associated with xenogeneic antibodies, such as antibodies that possess murine or rat variable and/or constant regions. First, because the effector portion is human, it can interact better with other parts of the human immune system, e.g., to destroy target cells more efficiently by complement-dependent cytotoxicity or antibody-dependent cellular cytotoxicity. Second, the human immune system should not recognize the antibody as foreign. Third, the half-life in human circulation will be similar to naturally occurring human antibodies, allowing smaller and less frequent doses to be given. Methods for preparing human antibodies are known in the art.

In addition to human antibodies, "humanized" antibodies can be used, and can have many advantages. Humanized antibodies generally are chimeric or mutant monoclonal antibodies from mouse, rat, hamster, rabbit or other species, bearing human constant and/or variable region domains or specific changes. Techniques for generating humanized antibodies are well known to those of skill in the art. For example, controlled rearrangement of antibody domains joined through protein disulfide bonds to form new, artificial protein molecules or "chimeric" antibodies can be utilized (Konieczny et al. (1981) *Haematologia (Budap.)* 14:95). Recombinant DNA technology can be used to construct gene fusions between DNA sequences encoding mouse antibody variable light and heavy chain domains and human antibody light and heavy chain constant domains (Morrison et al. (1984) *Proc. Natl. Acad. Sci. USA* 81:6851).

DNA sequences encoding antigen binding portions or complementarity determining regions (CDR's) of murine monoclonal antibodies can be grafted by molecular means into DNA sequences encoding frameworks of human antibody heavy and light chains (Jones et al. (1986) *Nature* 321:522; Riechmann et al. (1988) *Nature* 332:323). Expressed recombinant products are called "reshaped" or humanized antibodies, and comprise the framework of a human antibody light or heavy chain and antigen recognition portions, CDR's, of a murine monoclonal antibody.

Other methods for designing heavy and light chains and for producing humanized antibodies are described in, for example, U.S. Pat. Nos. 5,530,101; 5,565,332; 5,585,089; 5,639,641; 5,693,761; 5,693,762; and 5,733,743. Yet additional methods for humanizing antibodies are described in U.S. Pat. Nos. 4,816,567; 4,935,496; 5,502,167; 5,558,864; 5,693,493; 5,698,417; 5,705,154; 5,750,078; and 5,770,403, for example.

Molecules that interfere with the interaction between B7-H1 and DNA-PKcs, the interaction between B7-H1 and PD-1, and/or the interaction between B7-H1 and CD80, as described herein (e.g., small molecule inhibitors of DNA-PKcs, antibodies against B7-H1, DNA-PKcs, PD-1, and CD80, and fusion proteins containing portions of PD-1 or CD80 linked to an Ig Fc domain), can be incorporated into pharmaceutical compositions for treatment of cancer. Thus, this document also provides the use of such molecules in the manufacture of medicaments for treating cancer. The compositions further can include one or more pharmaceutically acceptable carriers, diluents and/or adjuvants.

A "pharmaceutically acceptable carrier" (also referred to as an "excipient" or a "carrier") is a pharmaceutically acceptable solvent, suspending agent, stabilizing agent, or any other pharmacologically inert vehicle for delivering one or more therapeutic compounds to a subject, which is nontoxic to the cell or mammal being exposed thereto at the dosages and concentrations employed. Pharmaceutically acceptable carriers can be liquid or solid, and can be selected with the planned manner of administration in mind so as to provide for the desired bulk, consistency, and other pertinent transport and chemical properties, when combined with one or more of therapeutic compounds and any other components of a given pharmaceutical composition. Typical pharmaceutically acceptable carriers include, by way of example and not limitation: water, saline solution, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Pharmaceutically acceptable carriers also include aqueous pH buffered solutions or liposomes (small vesicles composed of various types of lipids, phospholipids and/or surfactants which are useful for delivery of a drug to a mammal). Further examples of pharmaceutically acceptable carriers include buffers such as phosphate, citrate, and other organic acids, antioxidants such as ascorbic acid, low molecular weight (less than about ten residues) polypeptides, proteins such as serum albumin, gelatin, or immunoglobulins, hydrophilic polymers such as polyvinylpyrrolidone, amino acids such as glycine, glutamine, asparagine, arginine or lysine, monosaccharides, disaccharides, and other carbohydrates including glucose, mannose or dextrins, chelating agents such as EDTA, sugar alcohols such as mannitol or sorbitol, salt-forming counterions such as sodium, and/or nonionic surfactants such as TWEEN™, polyethylene glycol (PEG), and PLURONICS™.

Pharmaceutical compositions can be formulated by mixing one or more active agents (e.g., a DNA-PKcs inhibitor or an anti-B7-H1 blocking antibody) with one or more physiologically acceptable carriers, diluents, and/or adjuvants, and optionally other agents that are usually incorporated into formulations to provide improved transfer, delivery, tolerance, and the like. Pharmaceutical compositions can be formulated, e.g., in lyophilized formulations, aqueous solutions, dispersions, or solid preparations, such as tablets, dragees or capsules. A multitude of appropriate formulations can be found in the formulary known to pharmaceutical chemists: *Remington's Pharmaceutical Sciences* (18th ed, Mack Publishing Company, Easton, Pa. (1990)), particularly Chapter 87 by Block, Lawrence, therein. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies as described herein, provided that the active agent in the formulation is not inactivated by the formulation and the formulation is physiologically compatible and tolerable with the route of administration. See, also, Baldrick (2000) *Regul. Toxicol. Pharmacol.* 32:210-218; Wang (2000) *Int. J. Pharm.* 203: 1-60; Charman (2000) *J. Pharm. Sci.* 89:967-978; and Powell et al. (1998) *PDA J. Pharm. Sci. Technol.* 52:238-311), and the citations therein for additional information related to formulations, excipients and carriers well known to pharmaceutical chemists.

Pharmaceutical compositions include, without limitation, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Compositions and formulations can include sterile aqueous solutions, which also can contain buffers, diluents and other suitable additives (e.g., penetration enhancers, carrier compounds and other pharmaceutically acceptable carriers). Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions provided herein, such as dyes, flavoring agents, preservatives, antioxidants, opacifiers, thickening agents and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the polypeptide components within the compositions provided herein. The formulations can be sterilized if desired.

In some embodiments, a composition containing a DNA-PKcs inhibitor and/or an antibody or fusion protein as provided herein (e.g., an anti-B7-H7, anti-DNA-PKcs, anti-PD-1, or anti-CD80 antibody, or a PD-1-Fc or CD80-Fc fusion protein) can be in the form of a solution or powder with or without a diluent to make an injectable suspension. The composition may contain additional ingredients including, without limitation, pharmaceutically acceptable vehicles, such as saline, water, lactic acid, mannitol, or combinations thereof, for example.

Methods for using an agent (e.g., a small molecule inhibitor of DNA-PKcs, an antibody against B7-H1, DNA-PKcs, PD-1, or CD80, or a PD-1-Fc or CD80-Fc fusion protein) or a composition containing such an agent to treat cancer patients also are provided herein. The methods can include, for example, administering an agent or composition to a subject identified as being in need thereof. In some embodiments, a method as provided herein can further include steps such as identifying a mammal (e.g., a human cancer patient) that is to be treated with a chemotherapeutic agent (e.g., cisplatin, doxorubicin, SN38, paclitaxel, protein-bound paclitaxel (e.g., ABRAXANE®), temozolomide (e.g., TEMODAR®), or carboplatin) that causes DNA damage, or identifying a mammal as having a tumor with cells that express B7-H1. For example, a method can include identifying a mammal to be treated with a chemotherapeutic agent that causes DNA damage, and treating the mammal with an agent that inhibits the interaction between B7-H1 and DNA-PKcs. In some cases, a method can further include the step of administering the chemotherapeutic agent that causes DNA damage.

Any appropriate method can be used to administer a molecule as described herein to a mammal. Administration can be, for example, parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). In some embodiments, administration can be topical (e.g., transdermal, sublingual, ophthalmic, or intranasal), pulmonary (e.g., by inhalation or insufflation of powders or aerosols), or oral. In addition, a composition containing an antibody or fusion protein as described herein can be administered prior to, after, or in lieu of surgical resection of a tumor.

Compositions containing an antibody (e.g., an anti-B7-H1 antibody, an anti-DNA-PKcs antibody, an anti-PD-1 antibody, or an anti-CD80 antibody), a small molecule (e.g., NU7026) or a fusion protein (e.g., a PD-1-Fc fusion or a CD80-Fc fusion) can be administered to a mammal in any appropriate amount, at any appropriate frequency, and for any appropriate duration effective to achieve a desired outcome (e.g., to increase progression-free survival, or to reduce progression of the cancer). Combination therapies, in which a DNA-PKcs inhibitor and an anti-B7-H1 blocking antibody are administered to a mammal, can be particularly useful, as such therapies can target both chemoresistance and immunoresistance. For example, a first composition containing a DNA-PKcs inhibitor and a second composition containing an anti-B7-H1 antibody can be administered, either simultaneously (e.g., via simultaneous administration of separate compositions, or via administration of a composition containing both agents), or sequentially.

In some embodiments, a DNA-PKcs inhibitor and an anti-B7-H1 antibody can be administered to a mammal having cancer to reduce the progression rate of the cancer by 5, 10, 25, 50, 75, 100, or more percent. For example, the progression rate can be reduced such that no additional cancer progression is detected. In some embodiments, a DNA-PKcs inhibitor and an anti B7-H1 antibody can be administered to a mammal having cancer under conditions where progression-free survival is increased (e.g., by 5, 10, 25, 50, 75, 100, or more percent) as compared to the median progression-free survival of corresponding mammals having untreated cancer or the median progression-free survival of corresponding mammals having cancer and treated with other therapies (e.g., immune or chemotherapeutic agents alone). Progression-free survival can be measured over any length of time (e.g., one month, two months, three months, four months, five months, six months, or longer). Any appropriate method can be used to determine whether or not the progression rate of cancer is reduced. For skin cancer (e.g., melanoma), for example, the progression rate can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of cancer after treatment can be determined and compared to the stage before treatment to determine whether or not the progression rate has been reduced.

An effective amount of a composition containing an antibody as provided herein can be any amount that reduces a symptom of the condition being treated, without significant toxicity. With cancer, for example, an effective amount can reduce the progression rate of the cancer, increase the progression-free survival rate, or increase the median time to progression. Optimum dosages can vary depending on the relative potency of individual polypeptides (e.g., antibodies and fusion proteins), and can generally be estimated based on $EC_{50}$ found to be effective in in vitro and in vivo animal models. Typically, dosage is from 0.01 µg to 100 g per kg of body weight. For example, an effective amount of an antibody or fusion protein can be from about 1 mg/kg to about 100 mg/kg (e.g., about 5 mg/kg, about 10 mg/kg, about 20 mg/kg, about 50 mg/kg, or about 75 mg/kg). If a particular subject fails to respond to a particular amount, then the amount of the antibody can be increased by, for example, two fold. After receiving this higher concentration, the subject can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the clinical condition may require an increase or decrease in the actual effective amount administered.

The frequency of administration can be any frequency that reduces the progression rate of cancer, increases the progression-free survival rate, or increases the median time to progression without producing significant toxicity to the mammal. For example, the frequency of administration can be once or more daily, biweekly, weekly, monthly, or even less. The frequency of administration can remain constant or can be variable during the duration of treatment. A course of treatment can include rest periods. For example, a composition containing one or more agents (e.g., a small molecule, antibody, or fusion protein as provided herein) can be administered over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the cancer may require an increase or decrease in administration frequency.

An effective duration for administering a composition provided herein can be any duration that reduces the progression rate of cancer, increases the progression-free survival rate, or increases the median time to progression without producing significant toxicity to the mammal. Thus, the effective duration can vary from several days to several weeks, months, or years. In general, the effective duration for the treatment of cancer can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the cancer.

After administering one or more agents as provided herein to a mammal, the mammal can be monitored to determine whether or not the treatment was effective. For example, a mammal can be assessed after treatment to determine whether or not the progression rate of the cancer has been reduced. Any method, including those that are standard in the art, can be used to assess progression and survival rates.

The invention will be further described in the following examples, which do not limit the scope of the invention described in the claims.

EXAMPLES

Example 1—B7-H1 Renders Tumor Cells Resistant to Drugs that Cause DNA Damage Experiments were conducted to test whether B7-H1-expressing tumors would show resistance to drugs that cause DNA damage. Along with cisplatin, which crosslinks DNA, doxorubicin (a topoisomerase II inhibitor that leads to generation of free radicals) and SN38 (a topoisomerase I inhibitor) were tested. Drug sensitivity in B7-H1- and Mock-transfected 624mel melanoma cells was examined in cultures with varying concentrations of the drugs. After 72 hours of culture, tumor cell survival was measured with a MTS assay (Pei et al., Cancer Cell 16:259-266, 2009). As shown in FIG. 1A, B7-H1/624mel cells were more resistant than Mock/624mel cells to cisplatin, doxorubicin, and SN38. Consistent with a previous pharmacogenetic analysis, these data supported the idea that B7-H1 renders tumor cells resistant to cytotoxic chemotherapeutic agents. Since a mechanism of action of most cytotoxic drugs is to induce apoptosis (Sedletska et al., Curr Med Chem Anti-cancer Agents 5:251-265, 2005; and Wang et al., J Biol Chem 279:25535-25543, 2004), apoptosis of B7-H1/624mel and Mock/624mel tumor cells was measured and compared after treatment with doxorubicin. Specifically, apoptosis was measured based on the binding of Annexin V (AV) and the levels of tetramethylrhodamine ethyl ester (TMRE), a marker for mitochondria membrane potential (Jayaraman, J Immunolog Meth 306:68-79, 2005). As shown in FIG. 1B, B7-H1/624mel cells had 5-fold less apoptosis compared to Mock/624mel cells following treatment with doxorubicin. The level of active caspase-3 (an executive molecule of apoptosis) also was lower in B7-H1/624mel cells compared with Mock/624mel cells (FIG. 1C). Thus, B7-H1 may render tumor cells resistant to cytotoxic drugs by reducing their apoptotic potential to cytotoxic condition.

Example 2—B7-H1 is Associated with DNA-PKcs

Figure 2:
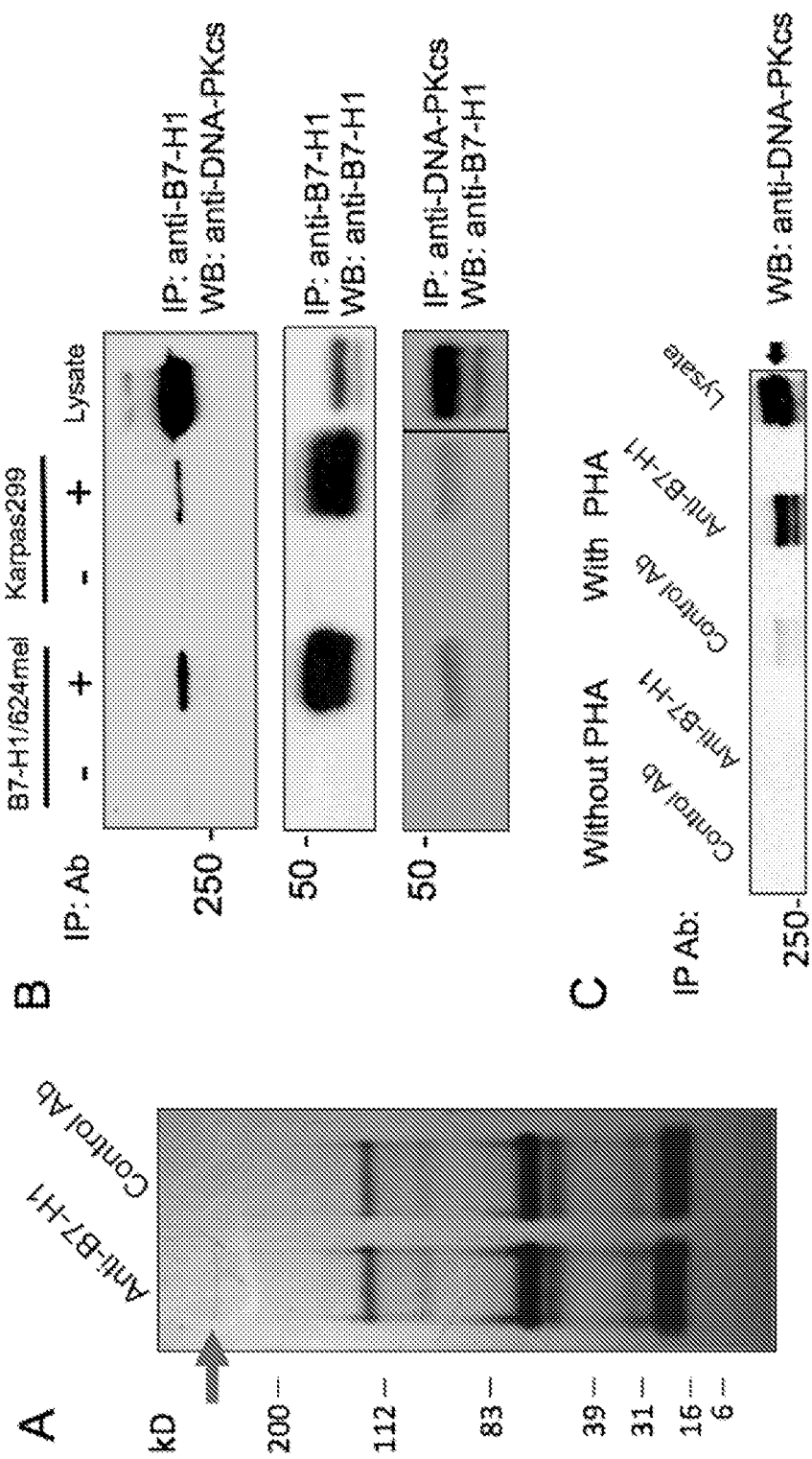
FIGS. 2A-2C are pictures from co-immunoprecipitation and Western blotting (WB) experiments, demonstrating that B7-H1 associates with DNA-PKcs.

A co-immunoprecipitation (Co-IP) assay with tumor cell lysates using anti-B7-H1 monoclonal antibody resulted in identification of a 450-kDa protein band (FIG. 2A). The protein band identified was larger than and distinct from the membrane proteins PD-1 (55 kDa) and CD80 (65 kDa) that also have been reported to interact with B7-H1. The band was excised from the gel, and mass spectroscopy revealed that the major component was DNA-PKcs (DNA dependent protein kinase, catalytic subunit). To confirm the association of B7-H1 with DNA-PKcs, Co-IP assays were performed using anti-DNA-PKcs and anti-B7-H1 monoclonal antibodies in a tumor cell line that constitutively expresses B7-H1 (Karpas299) and in a B7-H1-transfected tumor cell line (B7-H1/624mel). Both DNA-PKcs and B7-H1 were pulled down by their respective antibodies in B7-H1 transfected 624mel cells, as well as in the endogenous B7-H1-positive Karpas299 cells (FIG. 2B), suggesting that DNA-PKcs and B7-H1 indeed associate in vivo. Significantly, an association of DNA-PKcs and B7-H1 was detected in activated (known to up-regulate B7-H1 expression) but not resting human primary T cells (FIG. 2C), suggesting the association of B7-H1 with DNA-PKcs may be a general biological interaction that is not limited to tumor cells.

Figure 3:
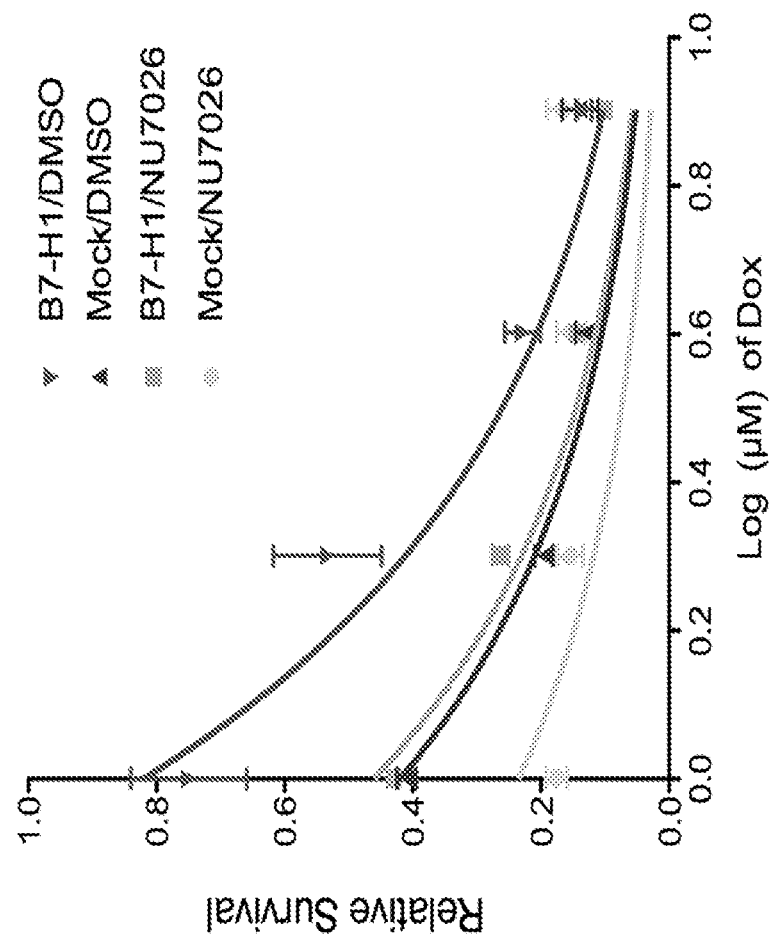
FIG. 3 is a graph plotting relative survival of tumor cells treated with a DNA-PKcs inhibitor, and showing that inhibition of DNA-PKcs reduced tumor drug resistance. Cells were pre-treated with DMSO or NU7026 (10 uM) for 1 hour before treatment with doxorubicin (Dox). The relative survival of tumor cells was measured by MTS assay 72 hours after Dox treatment.

Example 3—Inhibition of DNA-PKcs Activity Abolishes B7-H1-Mediated Chemoresistance To test whether the association of B7-H1 with DNA-PKcs is a mechanism of drug resistance, the effects of NU7026 on drug sensitivity of B7-H1- or Mock-transfected 624mel cells were tested. NU7026 is an ATP-competitive DNA-PKcs inhibitor, and 10 uM NU7026 completely inhibits DNA-PKcs activity (Veuger et al., Cancer Res 63:6008-6015, 2003; and Willmore et al., Blood 103:4659-4665, 2004). Using the same dose (10 uM) of NU7026, experiments were conducted to determine whether NU7026 would affect the drug sensitivity of B7-H1/624mel cells. As shown in FIG. 3, B7-H1/624mel cells demonstrated resistance to doxorubicin, compared with Mock/624mel cells. After pretreatment with NU7026, however, B7-H1/624mel cells lost their resistance to doxorubicin and had comparable drug sensitivity with Mock/624mel cells, suggesting that DNA-PKcs may contribute to B7-H1-mediated drug resistance (FIG. 3). NU7026 also increased the drug sensitivity of Mock/624mel cells, suggesting DNA-PKcs may be a downstream element of B7-H1 signaling pathway.

Figure 4:
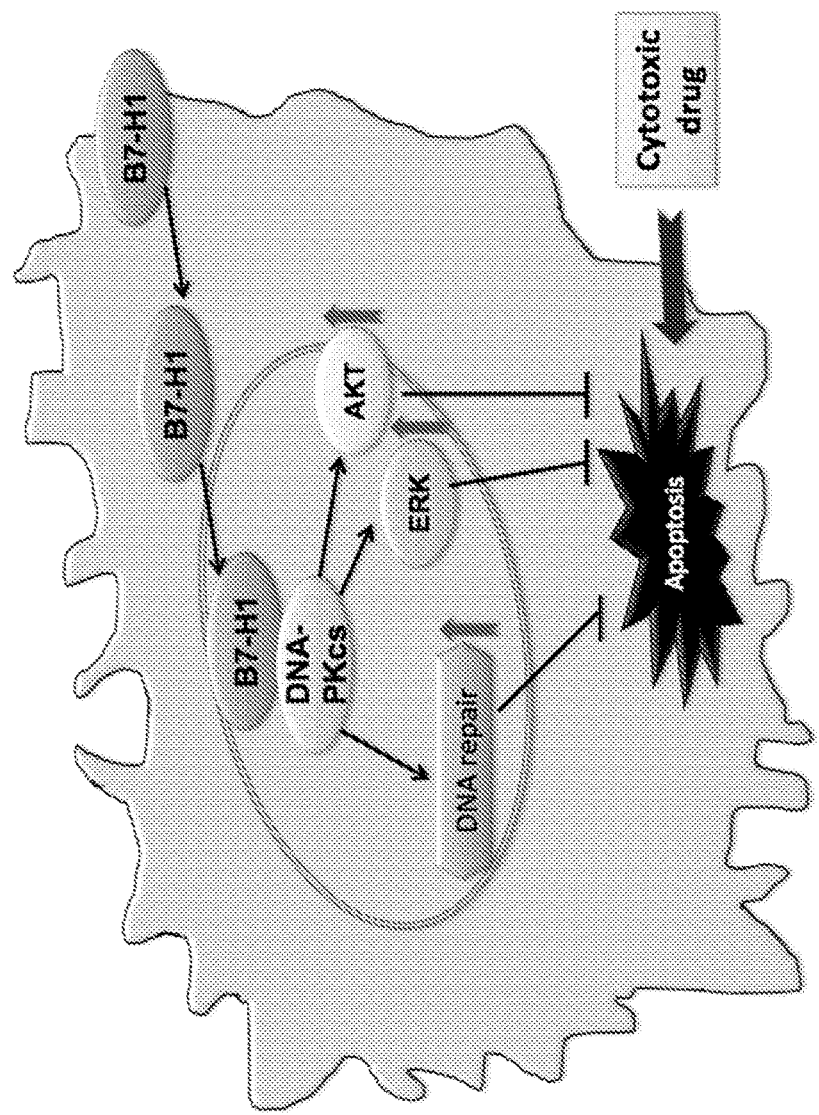
FIG. 4 is a diagram showing potential molecular mechanisms for B7-H1-mediated tumor chemoresistance.

Taken together, these preliminary data strongly suggest that DNA-PKcs plays a key role in B7-H1-mediated tumor chemoresistance, and that B7-H1 is a DNA damage checkpoint molecule that, association with DNA-PKcs, promotes tumor survival via DNA damage repair and activation of pro-survival signaling pathways, thus countering cytotoxic effects of chemotherapeutic agents (FIG. 4). To test this hypothesis, experiments are conducted to (1) define the role of B7-H1 interaction with DNA-PKcs in DNA damage repair and (2) define the role of B7-H1 interaction with DNA-PKcs in the activation of pro-survival signaling pathways. Conceptually, these studies extend the role of B7-H1, originally defined as an immune checkpoint molecule, to a DNA damage checkpoint molecule of tumor cells upon treatment with cytotoxic drugs.

Figure 5:
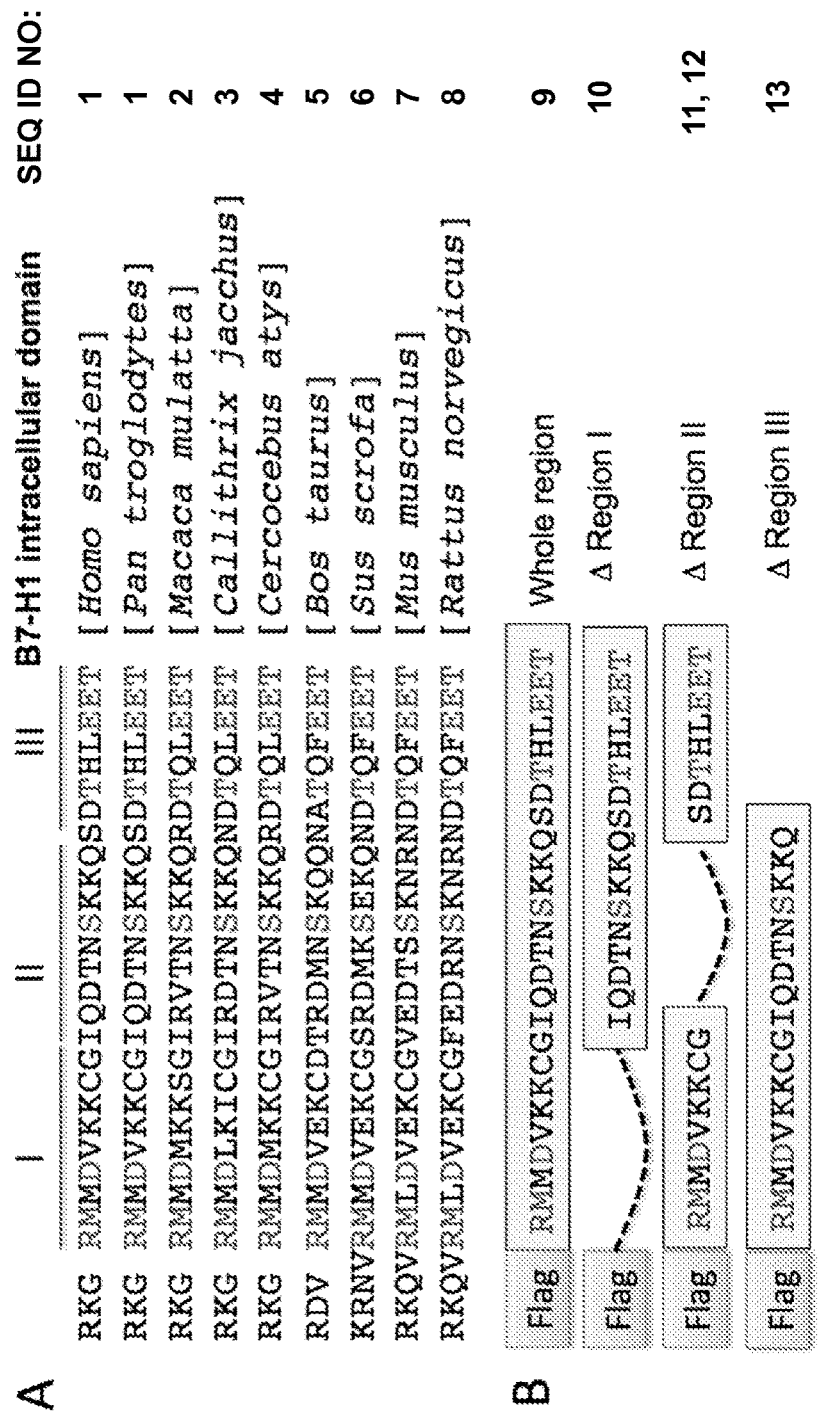
FIG. 5A is a cross-species alignment of the B7-H1 intracellular domains (ICD) from human (SEQ ID NO:1), chimpanzee (SEQ ID NO:1), Rhesus monkey (SEQ ID NO:2), marmoset (SEQ ID NO:3), sooty mangabey (SEQ ID NO:4), cow (SEQ ID NO:5), pig (SEQ ID NO:6), mouse (SEQ ID NO:7), and rat (SEQ ID NO:8). Conserved residues are in red.
FIG. 5B is a diagram of Flag-B7-H1 ICD domain fragments (SEQ ID NOS:9-13).

Example 4—Identifying the Binding Sites(s) of B7-H1 in Association with DNA-PKcs The anti-apoptosis function of B7-H1 has been identified in its intracellular domain (ICD) in tumor cells (Azuma et al., Blood 111:3635-3643, 2008). It is possible that B7-H1 uses its ICD in association with DNA-PKcs to achieve its anti-apoptosis function in tumor cells. The B7-H1 ICD has eight amino acid residues that are conserved across species (FIG. 5A, red font). Based on their distribution and locations, these amino acids can be grouped in three regions (I, II, and III).

To test which region is required for B7-H1 to associate with DNA-PKcs, individual region deletions or truncations are made for the B7-H1 ICD, as shown in FIG. 5B. Next, single residue mutations of each conserved amino acid in the required region are generated to test which amino acid is required for binding. Candidate amino acids are changed to Ala in this mutagenesis assay. Flag-B7-H1 ICD fusion proteins carrying regional truncations or individual mutations are produced. B7-H1-negative 624mel tumor cells are transfected with Flag-B7-H1 ICD, and are used in Co-IP (using anti-Flag antibody in pull-down assays) to assess the association of mutant or truncated B7-H1 ICD with DNA-PKcs. It is noted that the transmembrane domain of B7-H1 may be needed if the association with DNA-PKcs requires anchoring of B7-H1 to the cytoplasm or nuclear membrane. In this case, the transmembrane domain of B7-H1 is included in the Flag-B7-H1 fusion protein for the Co-IP assay.

Example 5—Identifying the Effects of B7-H1 on DNA Repair Function of DNA-PKcs

Figure 6:
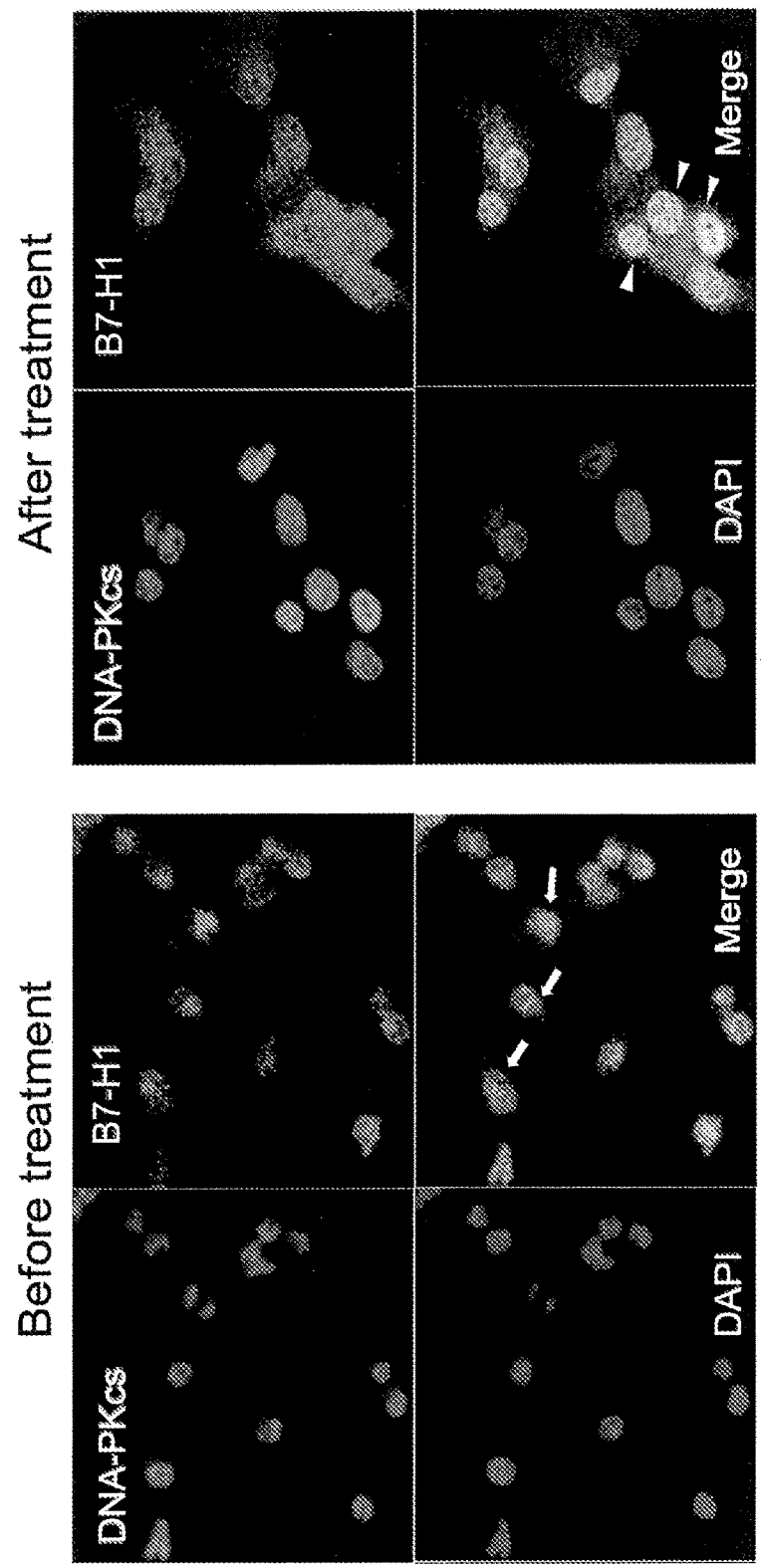
FIG. 6 is a series of pictures showing co-localization of B7-H1 and DNA-PKcs. A human breast tumor cell line (MDA-MB-231) was treated with doxorubicin (2 ug/ml) for 2 hours. Co-localization of B7-H1 and DNA-PKcs was observed in the nuclei. Arrows or arrowheads indicate B7-H1 in plasma or in nuclei, respectively.

B7-H1 undergoes redistribution from the cell surface into the nucleus in human breast tumor cells upon treatment with the cytotoxic drug, doxorubicin (Ghebeh et al., supra). Using the same model (MDA-MB-231, B7-H1 positive cell line), studies were conducted to examine whether translocation of B7-H1 results in close association with DNA-PKcs in the nucleus following drug treatment. The results shown in FIG. 6 demonstrate that before treatment with cytotoxic drug, DNA-PKcs was mainly localized in nuclei and B7-H1 was mainly localized in cytoplasm of tumor cells (arrows). After treatment, B7-H1 was enriched in the nuclei, and co-localization of B7-H1 and DNA-PKcs was observed in the nuclei (arrow heads in FIG. 6), suggesting that B7-H1 may be recruited to the nucleus to regulate DNA-PKcs activity in responses to DNA damage caused by chemotherapeutic drugs.

Figure 7:
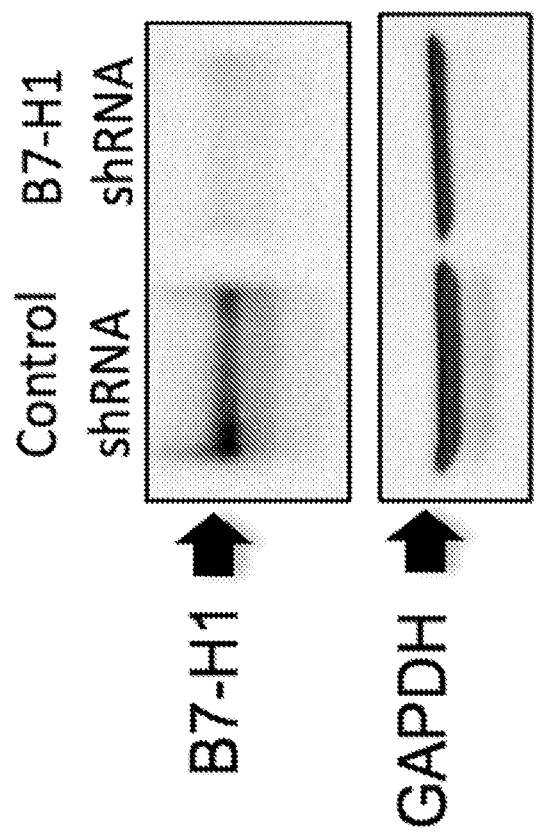
FIG. 7 is a picture of a blot showing B7-H1 or control (GAPDH) expression in human tumor cells (MDA-MB-231) following transfection with control or B7-H1 shRNA.

The phosphorylation of DNA-PKcs is required for rejoining of DNA double-strand breaks (DSBs) (Chan et al., *Genes Dev* 16:2333-2338, 2002), raising the possibility that B7-H1 stimulates DNA-PKcs activity to repair DNA DSBs. To test this, gamma-H2AX (γH2AX) is used. γH2AX has been widely used as a sensitive marker for DSBs (Banath et al., *BMC Cancer* 10:4, 2010; Mah et al., *Leukemia* 24:679-686, 2010; and Yuan et al., *FEBS Lett* 584:3717-3724, 2010). Nuclear γH2AX is measured by anti-phospho-H2AX (Ser139) (Cell Signaling, clone 20E3) in confocal immunofluorescence (IF) assays. A time course examination is conducted, with comparison of the distribution (nuclear foci or nuclear periphery) of γH2AX between B7-H1 positive and B7-H1 negative (knockdown) tumor cells upon treatment with cytotoxic drug (doxorubicin or cisplatin). As shown in FIG. 7, a method to knockdown B7-H1 in human tumor cells has been established. Five different fields are scored for γH2AX distribution and expression. Fisher's exact test is used to calculate the p-value. To quantify γH2AX expression and its relation with a specific cell cycle phase, a flow cytometry-based assay is used to measure the nuclear levels of γH2AX (Kataoka et al., *J Rad Res* 47:245-257, 2006) while measuring DNA content with propidium iodide (Solier et al., *Mol Cell Biol* 29:68-82, 2009).

To measure DNA-PKcs activity, anti-phospho-DNA-PKcs (Thr2609) antibody is used (BioLegend, clone 10B1) to detect auto-phosphorylated DNA-PKcs by Western blotting following treatment with cytotoxic agents over a course of time. To directly measure the DNA repair function of DNA-PKcs, an EJSGFP-based chromosomal break reporter (from the Addgene plasmid repository) is used to measure DNA-PKcs mediated non-homologous end joining (NHEJ; Bennardo et al., *PLoS Genet* 4:e1000110, 2008; and Gunn et al., *J Biol Chem* 286:42470-42482, 2011). EJSGFP contains a promoter that is separated from a GFP coding cassette by a puro gene that is flanked by two I-SceI sites that are in the same orientation. Once the puro gene is excised by NHEJ repair of the two I-SceI-induced DSBs, the promoter is joined to the rest of the expression cassette, leading to restoration of the GFP+ gene. By measuring the frequency of GFP+ cells, the function of DNA-PKcs in DNA repair is determined. Briefly, reporter plasmids are transfected into B7-H1-positive or -negative tumor cells, followed by treatment with one or more cytotoxic agents. The frequency of GFP+ cells is determined and compared between B7-H1-positive and negative-tumor cells using flow cytometry.

If B7-H1 in association with DNA-PKcs stimulates the DNA repair function of DNA-PKcs, expression of γH2AX (a sign of DNA DSBs) will decrease more slowly in B7-H1-positive tumor cells than in B7-H1-negative tumor cells, as a result of sufficient DNA repair by DNA-PKcs. Nuclear foci distributed throughout the nucleus are the most common distribution of γH2AX, but γH2AX expression at the nuclear periphery has been reported in early stage apoptotic cells (Solier et al., supra). Since DNA-PKcs also phosphorylates H2AX during apoptotic DNA fragmentation (Mukherjee et al., *DNA Repair* 5:575-590, 2006), the pattern of γH2AX distribution predicts whether B7-H1 regulates the function of DNA-PKcs in DNA repair or in DNA fragmentation.

Figure 8:
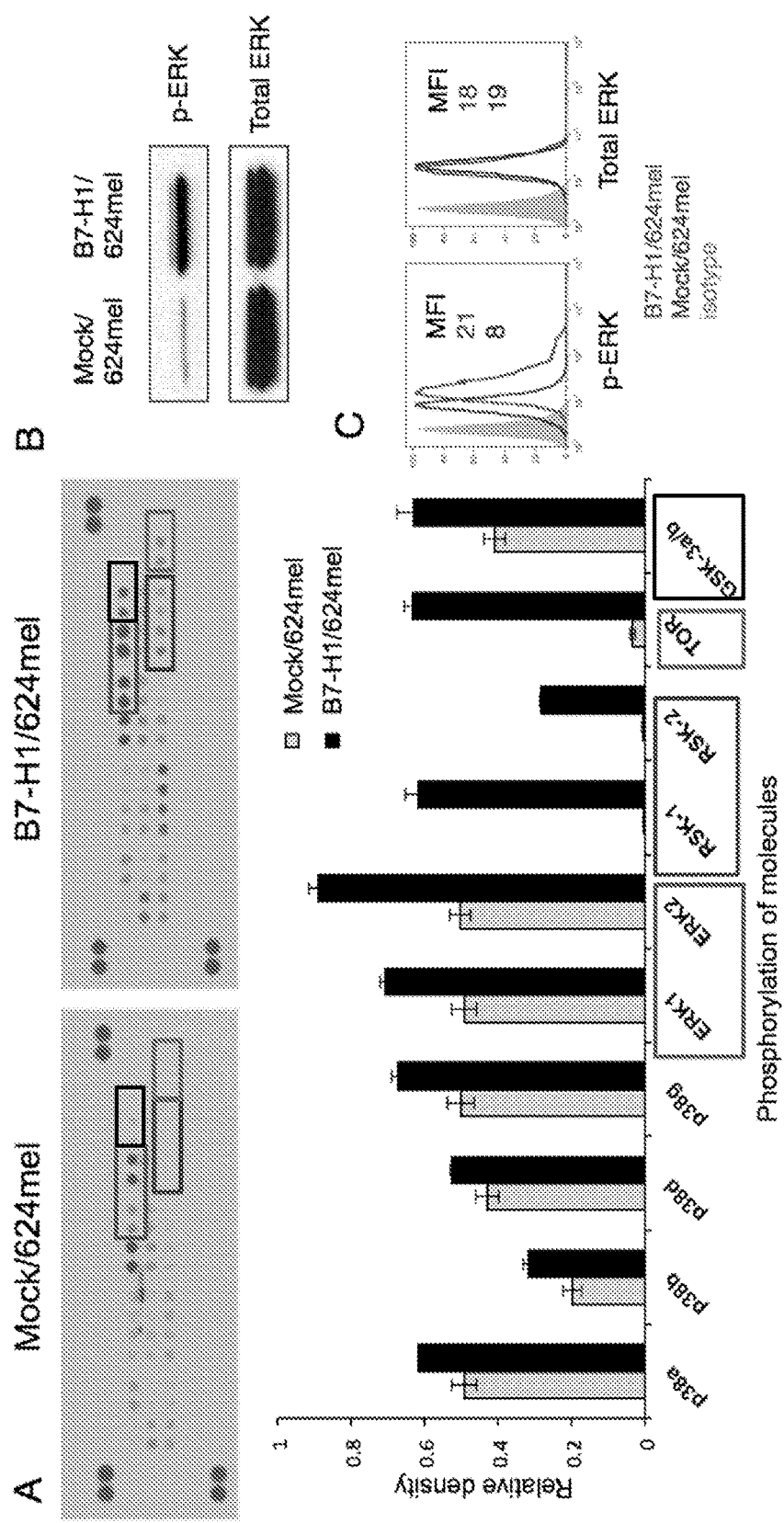
FIGS. 8A-8C demonstrate that B7-H1 enhances activation of the MAPK/ERK pathway.

Example 6—Defining the Role of B7-H1 Interaction with DNA-PKcs in the ERK/Bim Pathway DNA-PKcs as a kinase activates Akt and ERK pro-survival signaling pathways (Dragoi et al., *EMBO J* 24:779-789, 2005; and (Yotsumoto et al., *J Immunol* 180:809-816, 2008). The direct effects of DNA-PKcs on ERK activation are not clear, however. When the relative phosphorylation levels of proteins involved in the MAPK/ERK pathway in B7-H1/624mel cells and Mock/624mel cells was evaluated using antibody arrays (R&D Systems, Minneapolis, Minn.), phosphorylation of mTOR (an element in Akt pathway) and RSK1/2 (an element in ERK pathway) were significantly increased among B7-H1/624mel cells compared with Mock/624mel cells (FIG. 8A). Accordingly, phosphorylation of ERK1/2 and GSK-3 (a downstream element of Akt; Bodine, *Med Science Sports Exercise* 38:1950-1957, 2006) also were increased. Since increased phosphorylation of Akt in the nucleus is associated with B7-H1 re-distribution to the nucleus (Ghebeh et al., supra), and because B7-H1 and DNA-PKcs co-localize in the nucleus (FIG. 6), it is possible that activation of Akt pathway could be regulated by DNA-PKcs in association with B7-H1. Increased ERK1/2 activation was confirmed by Western blotting (FIG. 8B) and an intracellular flow cytometry assay that showed a >2-fold increase of phospho-ERK1/2 (FIG. 8C). In both assays, total ERK levels remained comparable between B7-H1/624mel and Mock/624mel, suggesting that B7-H1 regulates the activation of ERK1/2 rather than the ERK1/2 protein level. Based on these data, it is possible that upon treatment with cytotoxic drugs, B7-H1 is recruited to the nucleus where it functions as a platform for DNA-PKcs to activate ERK and Akt signaling pathways thereby suppressing tumor cell apoptosis.

Figure 9:
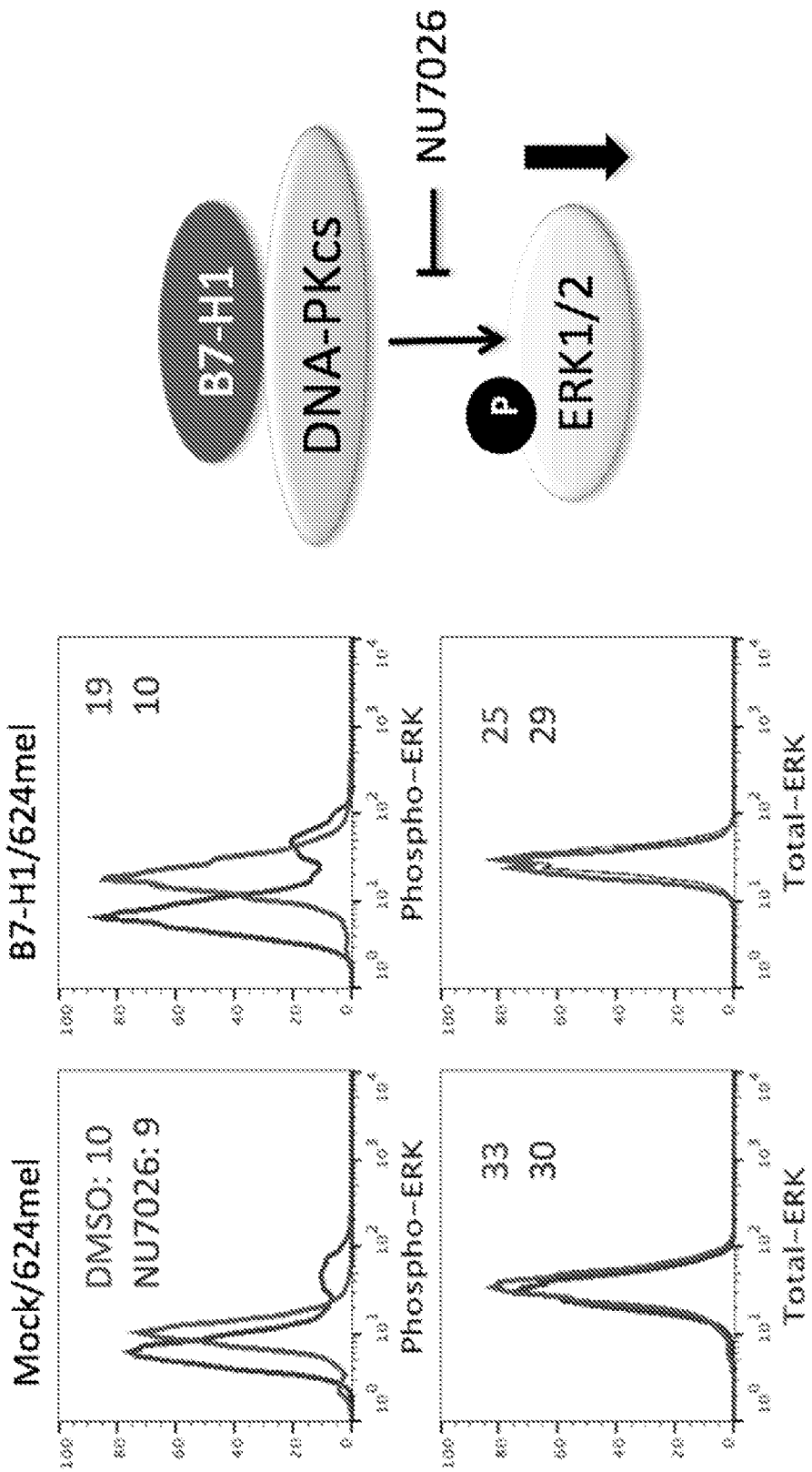
FIG. 9 is a series of graphs plotting the levels of phosphorylated ERK (top graphs) and total ERK (bottom graphs) in Mock/624mel (left) and B7-H1/624mel (right) tumor cells treated with DMSO or NU7026. Cells were treated with DMSO or NU7026 (10 uM) for 24 hours before intracellular staining for phospho-ERK or total ERK. Numbers are MFI Inhibition of DNA-PKcs reduced ERK activation, as indicated in the diagram on the right.
Figure 10:
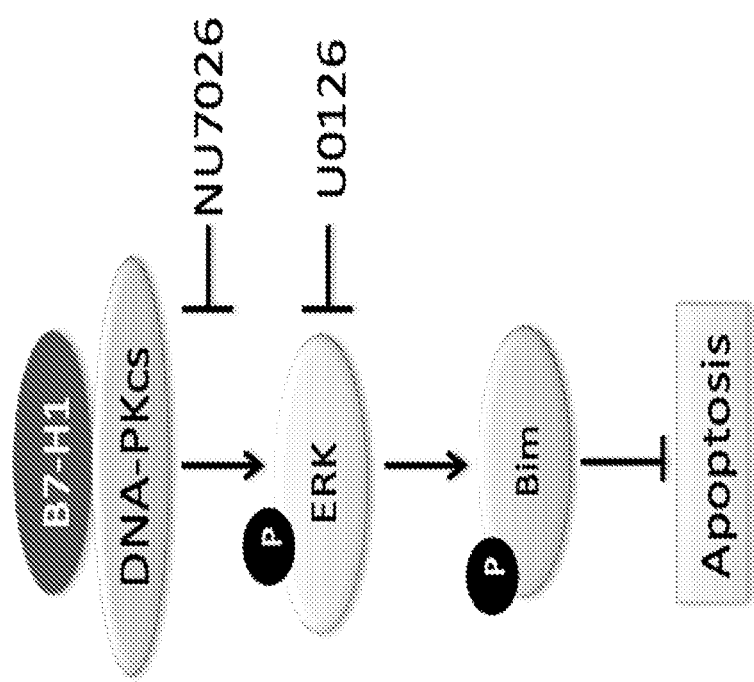
FIG. 10 is a schematic showing a potential DNA-PKcs/ERK/Bim pathway that may be used by B7-H1 to counter tumor cell apoptosis.

To test the role of DNA-PKcs in activation of the MAPK signal cascade, tumor cells were treated with NU7026, a DNA-PKcs specific inhibitor. The results shown in FIG. 9 demonstrate that NU7026 dramatically decreased (~2-fold) the activation of ERK1/2 in B7-H1/624mel cells but not Mock/624mel cells, suggesting DNA-PKcs may be a positive regulator of ERK1/2, and that DNA-PKcs may require B7-H1 in activation of ERK1/2. As a mechanism of action of ERK1/2 in drug resistance, ERK1/2 phosphorylates Bim and enhances degradation of Bim in tumor cells (Gillings, et al., *FEBS J* 276:6050-6062, 2009; and Luciano et al., *Oncogene* 22:6785-6793, 2003). The findings shown in FIG. 9 suggested that B7-H1 in association with DNA-PKcs enhances the activation of ERK1/2 that promotes Bim degradation by phosphorylation, thus countering tumor cell apoptosis (diagrammed in FIG. 10).

To test this, the phosphorylation of Bim in the presence of DNA-PKcs inhibitor (NU7026) is examined in endogenous B7-H1-positive MDA-MB-231 human tumor cells (FIG. 7) following treatment with cytotoxic drugs. The IC50 for NU7026 to inhibit DNA-PKcs is 0.23 uM (while the IC50 for inhibition of PI3K is 13 uM). To specifically examine the effects of NU7026 on Bim phosphorylation, NU7026 is titrated gradually from 10 uM to 0.23 uM (using the same volume of DMSO solvent as a control). To further confirm the role of DNA-PKcs in Bim phosphorylation, DNA-PKcs knockout cell lines (Wu et al., *J Immunol* 174:934-941, 2005) or DNA-PKcs knockdown cell lines are used to measure the levels of ERK1/2 activation in the absence of DNA-PKcs proteins. In both cases, the ERK1/2 inhibitor U0126 (which inhibits MEK, an upstream kinase of ERK1/2) is used to confirm that phosphorylation of Bim is mediated by ERK1/2 activation. To specifically determine whether DNA-PKcs requires B7-H1 to regulate ERK1/2 activation and Bim phosphorylation, the effects of DNA-PKcs inhibitor are examined in B7-H1 knockdown tumor cells (FIG. 7). To measure phosphorylation of Bim, an electrophoretic mobility shift assay of Bim in Western blot is used (Luciano et al., supra; and O'Reilly et al., *J Immunol* 183:261-269, 2009). In this assay, phosphorylated Bim migrates more slowly than non-phosphorylated Bim. To confirm that the slower migrating band of Bim is due to phosphorylation of Bim, lysates are incubated with lambda phosphatase (λ-PPase, 15 ug/200 U for 1 h), which de-phosphorylates modified serine, threonine and tyrosine residues. To specifically identify the phosphorylation of Bim, an anti-phospho-Bim (Ser69 in human) antibody (Cell Signaling Tech. #4581) is used in a Western blotting assay, since phosphorylation of Bim at Ser69 by ERK/1/2 promotes Bim degradation (Luciano et al., supra). Total Bim also is measured to determine to what degree Bim is undergoing degradation. Accordingly, the apoptosis of tumor cells is measured by flow cytometry using antibody against activated caspase-3 as described in FIG. 1.

Figure 11:
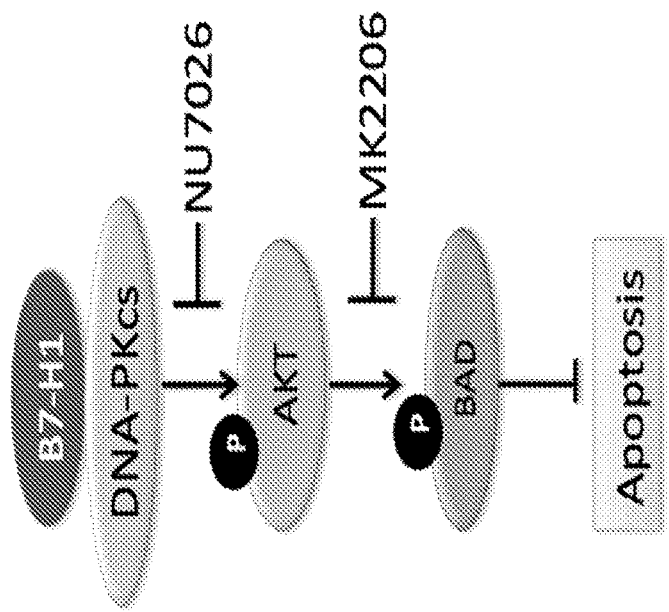
FIG. 11 is a schematic showing a potential DNA-PKcs/Akt/Bad pathway that may be used by B7-H1 to counter tumor cell apoptosis.

Example 7—Defining the Role of B7-H1 Interaction with DNA-PKcs in Akt/Bad Pathway DNA-PKcs enhances Akt activity (Dragoi et al., supra; and Feng et al., *J Biol Chem* 279:41189-41196, 2004). The increase of mTOR activation in B7-H1/624mel cells (FIG. 8) and the association of B7-H1 with DNA-PKcs (FIG. 2) suggest that Akt could be a downstream element in the B7-H1/DNA-PKcs pathway. Since activated Akt promotes cell survival by phosphorylating Bad, and blocks Bad-induced death (Datta et al., *Cell* 91:231-241, 1997; and del Peso et al., *Science* 278:687-689, 1997), it is possible that B7-H1 in association with DNA-PKcs enhances the activation of Akt that decreases Bad via phosphorylation, thus countering tumor cell apoptosis (FIG. 11). To test this hypothesis, the phosphorylation of Bad is examined in B7-H1 positive or negative tumor cells following treatment with cytotoxic agents in the presence of DNA-PKcs inhibitor (NU7026), or in DNA-PKcs knockout cells. In both cases, to confirm that activated Akt mediates the phosphorylation of Bad, the Akt inhibitor MK2206 (Merck) is used to directly inhibit the enzyme activity of activated Akt (Merck data sheet) in the studies. To specifically identify the phosphorylation of Bad, anti-phospho-Bad (Ser136) antibody (Cell Signaling Technology, clone 185D10) is used in a Western blotting assay, since Akt preferentially phosphorylates Bad at Ser136 in tumor cells (Hayakawa et al., *Cancer Res* 60:5988-5994, 2000). Phosphorylation of Bad could be mediated by activated ERK1/2, which phosphorylates Bad at Ser122; an anti-phospho-Bad (Ser122) antibody (Pierce-Antibodies) is used to test this possibility. Total Bad is measured to determine the degree of Bad degradation. If DNA-PKcs functions as an upstream regulator of Bad, reduced phosphorylation of Bad is identified in cells treated with DNA-PKcs inhibitor NU7026 or in cells without DNA-PKcs.

Taken together, these studies provide new insights for overcoming tumor chemoresistance, and a new direction for future combined chemotherapy and immunotherapy targeting B7-H1 expressed by aggressive or refractory human tumor cells.

Example 8—DNA-PKcs Activity is Required for Association of DNA-PKcs with B7-H1

Figure 15A:
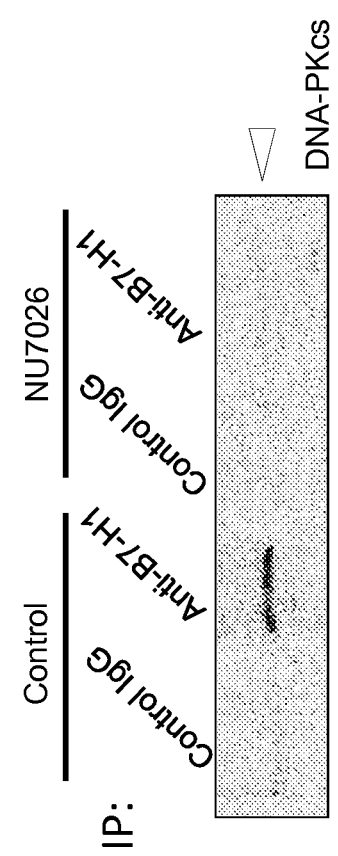
FIGS. 15A and 15B show that DNA-PKcs activity is required for the association of DNA-PKcs with B7-H1. MBA-MD-231 human breast cancer cells, which are positive for B7-H1, were incubated with NU7026, an inhibitor of DNA-PKcs.
Figure 15B:
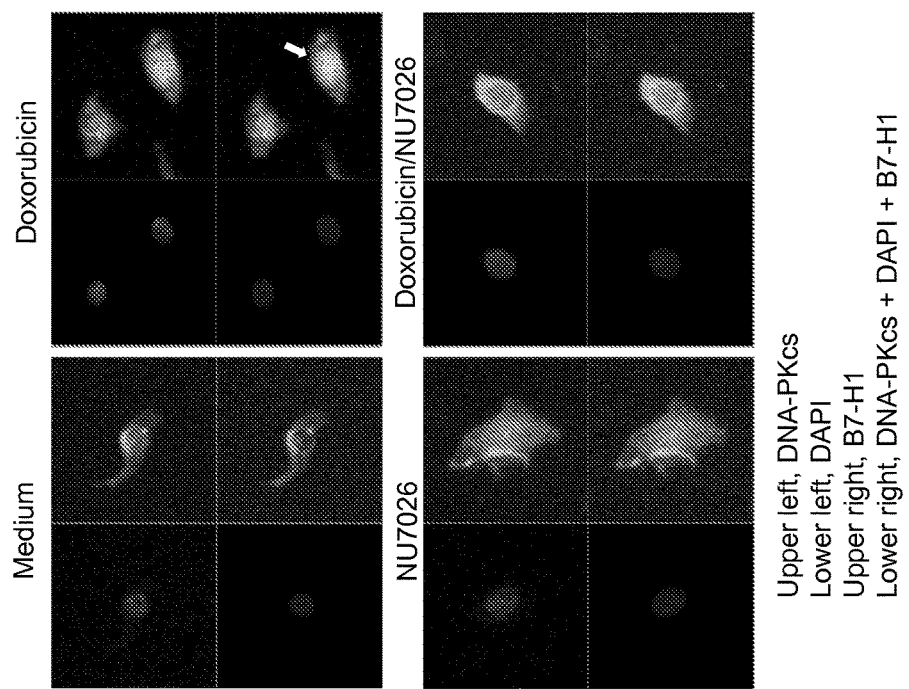

B7-H1 positive human breast cancer cells (MBA-MD-231) were used to examine the association of DNA-PKcs and B7-H1. Immuno-precipitation assays showed that NU7026, an inhibitor of DNA-PKCs, abolished the association of B7-H1 with DNA-PKcs (FIG. 15A), while immunofluorescence staining showed that doxorubicin-induced co-localization of B7-H1 and DNA-PKcs at the nucleus (FIG. 15B, arrow, upper right panel) was blocked by 1 μM NU7026 (lower right panel). The IC50 for inhibiting DNA-PKcs activity is 0.23 μM.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a cancer patient, comprising:
   (a) administering, to a cancer patient to be treated with a chemotherapeutic agent that causes DNA damage, an amount of a molecule targeted to DNA-PKcs sufficient to reduce the interaction of DNA-PKcs with B7-H1, wherein the molecule targeted to DNA-PKcs comprises NU7026, NU7441, IC86621, IC87102, IC87361, OK-1035, SU11752, vanillin, or IC486241; and
   (b) administering the chemotherapeutic agent to the patient.

2. The method of claim 1, wherein the patient is a human.

3. The method of claim 1, wherein the chemotherapeutic agent comprises cisplatin, doxorubicin, SN38, paclitaxel, protein-bound paclitaxel, temozolomide, or carboplatin.

4. The method of claim 1, wherein the molecule targeted to DNA-PKcs and the chemotherapeutic agent are administered simultaneously.

5. The method of claim 1, wherein the molecule targeted to DNA-PKcs and the chemotherapeutic agent are administered sequentially.

6. The method of claim 1, wherein the cancer patient is identified as having a tumor that expresses B7-H1 at an elevated level.

* * * * *

UNITED STATES PATENT AND TRADEMARK OFFICE
CERTIFICATE OF CORRECTION

PATENT NO. : 10,517,875 B2
APPLICATION NO. : 15/325612
DATED : December 31, 2019
INVENTOR(S) : Haidong Dong It is certified that error appears in the above-identified patent and that said Letters Patent is hereby corrected as shown below:

On the Title Page

Column 1 (Assignee), Line 2, delete "Engineering" and insert -- Education --.

Signed and Sealed this
Seventh Day of July, 2020

Andrei Iancu
*Director of the United States Patent and Trademark Office*

SEQUENCE LISTING

<160> NUMBER OF SEQ ID NOS: 19

<210> SEQ ID NO 1
<211> LENGTH: 29
<212> TYPE: PRT
<213> ORGANISM: Homo sapiens

<400> SEQUENCE: 1

Arg Lys Gly Arg Met Met Asp Val Lys Lys Cys Gly Ile Gln Asp Thr
1               5                   10                  15

Asn Ser Lys Lys Gln Ser Asp Thr His Leu Glu Glu Thr
            20                  25

<210> SEQ ID NO 2
<211> LENGTH: 29
<212> TYPE: PRT
<213> ORGANISM: Macaca mulatta

<400> SEQUENCE: 2

```
Arg Lys Gly Arg Met Met Asp Met Lys Lys Ser Gly Ile Arg Val Thr
1               5                   10                  15

Asn Ser Lys Lys Gln Arg Asp Thr Gln Leu Glu Glu Thr
            20                  25
```

<210> SEQ ID NO 3
<211> LENGTH: 29
<212> TYPE: PRT
<213> ORGANISM: Callithrix jacchus

<400> SEQUENCE: 3

```
Arg Lys Gly Arg Met Met Asp Leu Lys Ile Cys Gly Ile Arg Asp Thr
1               5                   10                  15

Asn Ser Lys Lys Gln Asn Asp Thr Gln Leu Glu Glu Thr
            20                  25
```

<210> SEQ ID NO 4
<211> LENGTH: 29
<212> TYPE: PRT
<213> ORGANISM: Cercocebus atys

<400> SEQUENCE: 4

```
Arg Lys Gly Arg Met Met Asp Met Lys Lys Cys Gly Ile Arg Val Thr
1               5                   10                  15

Asn Ser Lys Lys Gln Arg Asp Thr Gln Leu Glu Glu Thr
            20                  25
```

<210> SEQ ID NO 5
<211> LENGTH: 29
<212> TYPE: PRT
<213> ORGANISM: Bos taurus

<400> SEQUENCE: 5

```
Arg Asp Val Arg Met Met Asp Val Glu Lys Cys Asp Thr Arg Asp Met
1               5                   10                  15

Asn Ser Lys Gln Gln Asn Ala Thr Gln Phe Glu Glu Thr
            20                  25
```

<210> SEQ ID NO 6
<211> LENGTH: 30
<212> TYPE: PRT
<213> ORGANISM: Sus scrofa

<400> SEQUENCE: 6

```
Lys Arg Asn Val Arg Met Met Asp Val Glu Lys Cys Gly Ser Arg Asp
1               5                   10                  15

Met Lys Ser Glu Lys Gln Asn Asp Thr Gln Phe Glu Glu Thr
            20                  25                  30
```

<210> SEQ ID NO 7
<211> LENGTH: 30
<212> TYPE: PRT
<213> ORGANISM: Mus musculus

<400> SEQUENCE: 7

```
Arg Lys Gln Val Arg Met Leu Asp Val Glu Lys Cys Gly Val Glu Asp
1               5                   10                  15

Thr Ser Ser Lys Asn Arg Asn Asp Thr Gln Phe Glu Glu Thr
            20                  25                  30
```

<210> SEQ ID NO 8
<211> LENGTH: 30

```
<212> TYPE: PRT
<213> ORGANISM: Rattus norvegicus

<400> SEQUENCE: 8

Arg Lys Gln Val Arg Met Leu Asp Val Glu Lys Cys Gly Phe Glu Asp
1               5                   10                  15

Arg Asn Ser Lys Asn Arg Asn Asp Thr Gln Phe Glu Glu Thr
            20                  25                  30

<210> SEQ ID NO 9
<211> LENGTH: 26
<212> TYPE: PRT
<213> ORGANISM: Homo sapiens

<400> SEQUENCE: 9

Arg Met Met Asp Val Lys Lys Cys Gly Ile Gln Asp Thr Asn Ser Lys
1               5                   10                  15

Lys Gln Ser Asp Thr His Leu Glu Glu Thr
            20                  25

<210> SEQ ID NO 10
<211> LENGTH: 17
<212> TYPE: PRT
<213> ORGANISM: Homo sapiens

<400> SEQUENCE: 10

Ile Gln Asp Thr Asn Ser Lys Lys Gln Ser Asp Thr His Leu Glu Glu
1               5                   10                  15

Thr

<210> SEQ ID NO 11
<211> LENGTH: 9
<212> TYPE: PRT
<213> ORGANISM: Homo sapiens

<400> SEQUENCE: 11

Arg Met Met Asp Val Lys Lys Cys Gly
1               5

<210> SEQ ID NO 12
<211> LENGTH: 8
<212> TYPE: PRT
<213> ORGANISM: Homo sapiens

<400> SEQUENCE: 12

Ser Asp Thr His Leu Glu Glu Thr
1               5

<210> SEQ ID NO 13
<211> LENGTH: 18
<212> TYPE: PRT
<213> ORGANISM: Homo sapiens

<400> SEQUENCE: 13

Arg Met Met Asp Val Lys Lys Cys Gly Ile Gln Asp Thr Asn Ser Lys
1               5                   10                  15

Lys Gln

<210> SEQ ID NO 14
<211> LENGTH: 873
<212> TYPE: DNA
<213> ORGANISM: Homo sapiens
```

<400> SEQUENCE: 14

```
atgaggatat ttgctgtctt tatattcatg acctactggc atttgctgaa cgcatttact        60
gtcacggttc ccaaggacct atatgtggta gagtatggta gcaatatgac aattgaatgc       120
aaattcccag tagaaaaaca attagacctg gctgcactaa ttgtctattg ggaaatggag       180
gataagaaca ttattcaatt tgtgcatgga gaggaagacc tgaaggttca gcatagtagc       240
tacagacaga gggcccggct gttgaaggac cagctctccc tgggaaatgc tgcacttcag       300
atcacagatg tgaaattgca ggatgcaggg gtgtaccgct gcatgatcag ctatggtggt       360
gccgactaca agcgaattac tgtgaaagtc aatgccccat acaacaaaat caaccaaaga       420
attttggttg tggatccagt cacctctgaa catgaactga catgtcaggc tgagggctac       480
cccaaggccg aagtcatctg gacaagcagt gaccatcaag tcctgagtgg taagaccacc       540
accaccaatt ccaagagaga ggagaagctt ttcaatgtga ccagcacact gagaatcaac       600
acaacaacta atgagatttt ctactgcact tttaggagat tagatcctga ggaaaaccat       660
acagctgaat tggtcatccc agaactacct ctggcacatc tccaaatga aaggactcac       720
ttggtaattc tgggagccat cttattatgc cttggtgtag cactgacatt catcttccgt       780
ttaagaaaag ggagaatgat ggatgtgaaa aatgtggca tccaagatac aaactcaaag       840
aagcaaagtg atacacattt ggaggagacg taa                                    873
```

<210> SEQ ID NO 15
<211> LENGTH: 290
<212> TYPE: PRT
<213> ORGANISM: Homo sapiens

<400> SEQUENCE: 15

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Asn Glu Ile Phe Tyr
        195                 200                 205
```

```
Cys Thr Phe Arg Arg Leu Asp Pro Glu Glu Asn His Thr Ala Glu Leu
    210                 215                 220
Val Ile Pro Glu Leu Pro Leu Ala His Pro Pro Asn Glu Arg Thr His
225                 230                 235                 240
Leu Val Ile Leu Gly Ala Ile Leu Cys Leu Gly Val Ala Leu Thr
                245                 250                 255
Phe Ile Phe Arg Leu Arg Lys Gly Arg Met Met Asp Val Lys Lys Cys
                260                 265                 270
Gly Ile Gln Asp Thr Asn Ser Lys Lys Gln Ser Asp Thr His Leu Glu
                275                 280                 285
Glu Thr
    290
```

<210> SEQ ID NO 16
<211> LENGTH: 948
<212> TYPE: DNA
<213> ORGANISM: Homo sapiens

<400> SEQUENCE: 16

```
gcctgagcag tggagaaggc ggcactctgg tggggctgct ccaggcatgc agatcccaca    60
ggcgccctgg ccagtcgtct gggcggtgct acaactgggc tggcggccag gatggttctt   120
agactcccca gacaggccct ggaacccccc caccttctcc ccagccctgc tcgtggtgac   180
cgaagggac aacgccacct tcacctgcag cttctccaac atcggagag cttcgtgct    240
aaactggtac cgcatgagcc ccagcaacca gacggacaag ctggccgctt ccccgagga   300
ccgcagccag cccggccagg actgccgctt ccgtgtcaca caactgccca cgggcgtga   360
cttccacatg agcgtggtca gggcccggcg caatgacagc ggcacctacc tctgtggggc   420
catctccctg gcccccaagg cgcagatcaa agagagcctg cgggcagagc tcagggtgac   480
agagagaagg gcagaagtgc ccacagccca ccccagcccc tcacccaggc agccggcca   540
gttccaaacc ctggtggttg gtgtcgtggg cggcctgctg gcagcctgg tgctgctagt   600
ctgggtcctg gccgtcatct gctcccgggc cgcacgaggg acaataggag ccaggcgcac   660
cggccagccc ctgaaggagg acccctcagc cgtgcctgtg ttctctgtgg actatgggga   720
gctggatttc cagtggcgag agaagacccc ggagcccccc gtgccctgtg tccctgagca   780
gacggagtat gccaccattg tctttcctag cggaatgggc acctcatccc cgcccgcag   840
gggctcagcc gacggccctc ggagtgccca gccactgagg cctgaggatg acactgctc   900
ttggccctc tgaccggctt ccttggccac cagtgttctg cagaccct                948
```

<210> SEQ ID NO 17
<211> LENGTH: 288
<212> TYPE: PRT
<213> ORGANISM: Homo sapiens

<400> SEQUENCE: 17

```
Met Gln Ile Pro Gln Ala Pro Trp Pro Val Val Trp Ala Val Leu Gln
1               5                   10                  15
Leu Gly Trp Arg Pro Gly Trp Phe Leu Asp Ser Pro Asp Arg Pro Trp
            20                  25                  30
Asn Pro Pro Thr Phe Ser Pro Ala Leu Leu Val Val Thr Glu Gly Asp
                35                  40                  45
Asn Ala Thr Phe Thr Cys Ser Phe Ser Asn Thr Ser Glu Ser Phe Val
        50                  55                  60
Leu Asn Trp Tyr Arg Met Ser Pro Ser Asn Gln Thr Asp Lys Leu Ala
```

```
Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 18
<211> LENGTH: 2757
<212> TYPE: DNA
<213> ORGANISM: Homo sapiens

<400> SEQUENCE: 18

```
gacaagtact gagtgaactc aaaccctctg taaagtaaca gaagttagaa ggggaaatgt    60
cgcctctctg aagattaccc aaagaaaaag tgatttgtca ttgctttata gactgtaaga   120
agagaacatc tcagaagtgg agtcttaccc tgaaatcaaa ggatttaaag aaaaagtgga   180
attttcttc agcaagctgt gaaactaaat ccacaacctt tggagaccca ggaacaccct   240
ccaatctctg tgtgttttgt aaacatcact ggagggtctt ctacgtgagc aattggattg   300
tcatcagccc tgcctgtttt gcacctggga agtgccctgg tcttacttgg gtccaaattg   360
ttggctttca cttttgaccc taagcatctg aagccatggg ccacacacgg aggcagggaa   420
catcaccatc aagtgtcca tacctcaatt tctttcagct cttggtgctg ctggtctttt   480
ctcacttctg ttcaggtgtt atccacgtga ccaaggaagt gaaagaagtg caacgctgt   540
cctgtggtca aatgtttct gttgaagagc tggcacaaac tcgcatctac tggcaaaagg   600
agaagaaaat ggtgctgact atgatgtctg gggacatgaa tatatggccc gagtacaaga   660
accggaccat ctttgatatc actaataacc tctccattgt gatcctggct ctgcgcccat   720
ctgacgaggg cacatacgag tgtgttgttc tgaagtatga aaaagacgct ttcaagcggg   780
aacacctggc tgaagtgacg ttatcagtca aagctgactt ccctacacct agtatatctg   840
actttgaaat tccaacttct aatattagaa ggataaattg ctcaacctct ggaggttttc   900
```

| | | | | |
|---|---|---|---|---|
| cagagcctca | cctctcctgg | ttggaaaatg | gagaagaatt | aaatgccatc aacacaacag | 960 |
| tttcccaaga | tcctgaaact | gagctctatg | ctgttagcag | caaactggat ttcaatatga | 1020 |
| caaccaacca | cagcttcatg | tgtctcatca | agtatggaca | tttaagagtg aatcagacct | 1080 |
| tcaactggaa | tacaaccaag | caagagcatt | tcctgataa | cctgctccca tcctgggcca | 1140 |
| ttaccttaat | ctcagtaaat | ggaattttg | tgatatgctg | cctgacctac tgctttgccc | 1200 |
| caagatgcag | agagagaagg | aggaatgaga | gattgagaag | ggaaagtgta cgccctgtat | 1260 |
| aacagtgtcc | gcagaagcaa | ggggctgaaa | agatctgaag | gtcccacctc catttgcaat | 1320 |
| tgacctcttc | tgggaacttc | ctcagatgga | caagattacc | ccaccttgcc ctttacgtat | 1380 |
| ctgctcttag | gtgcttcttc | acttcagttg | ctttgcagga | agtgtctaga ggaatatggt | 1440 |
| gggcacagaa | gtagctctgg | tgaccttgat | caaggtgttt | tgaaatgcag aattcttgag | 1500 |
| ttctggaagg | gactttagag | aataccagtg | ttattaatga | caaaggcact gaggcccagg | 1560 |
| gaggtgaccc | gaattataaa | ggccagcgcc | agaacccaga | tttcctaact ctggtgctct | 1620 |
| ttccctttat | cagtttgact | gtggcctgtt | aactggtata | tacatatata tgtcaggcaa | 1680 |
| agtgctgctg | gaagtagaat | ttgtccaata | acaggtcaac | ttcagagact atctgatttc | 1740 |
| ctaatgtcag | agtagaagat | tttatgctgc | tgtttacaaa | agcccaatgt aatgcatagg | 1800 |
| aagtatggca | tgaacatctt | taggagacta | atggaaatat | tattggtgtt tacccagtat | 1860 |
| tccattttt | tcattgtgtt | ctctattgct | gctctctcac | tcccccatga ggtacagcag | 1920 |
| aaaggagaac | tatccaaaac | taatttcctc | tgacatgtaa | gacgaatgat ttaggtacgt | 1980 |
| caaagcagta | gtcaaggagg | aaagggatag | tccaaagact | taactggttc atattggact | 2040 |
| gataatctct | ttaaatggct | ttatgctagt | ttgacctcat | ttgtaaaata tttatgagaa | 2100 |
| agttctcatt | taaaatgaga | tcgttgttta | cagtgtatgt | actaagcagt aagctatctt | 2160 |
| caaatgtcta | aggtagtaac | tttccatagg | gcctccttag | atccctaaga tggctttttc | 2220 |
| tccttggtat | ttctgggtct | ttctgacatc | agcagagaac | tggaaagaca tagccaactg | 2280 |
| ctgttcatgt | tactcatgac | tcctttctct | aaaactgcct | tccacaattc actagaccag | 2340 |
| aagtggacgc | aacttaagct | gggataatca | cattatcatc | tgaaaatctg gagttgaaca | 2400 |
| gcaaaagaag | acaacatttc | tcaaatgcac | atctcatggc | agctaagcca catggctggg | 2460 |
| atttaaagcc | tttagagcca | gcccatggct | ttagctacct | cactatgctg cttcacaaac | 2520 |
| cttgctcctg | tgtaaaacta | tattctcagt | gtagggcaga | gaggtctaac accaacataa | 2580 |
| ggtactagca | gtgtttcccg | tattgacagg | aatacttaac | tcaataattc ttttcttttc | 2640 |
| catttagtaa | cagttgtgat | gactatgttt | ctattctaag | taattcctgt attctacagc | 2700 |
| agatactttg | tcagcaatac | taagggaaga | aacaaagttg | aaccgtttct ttaataa | 2757 |

<210> SEQ ID NO 19
<211> LENGTH: 288
<212> TYPE: PRT
<213> ORGANISM: Homo sapiens

<400> SEQUENCE: 19

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

```
Ser Cys Gly His Asn Val Ser Val Glu Glu Leu Ala Gln Thr Arg Ile
    50              55                  60

Tyr Trp Gln Lys Glu Lys Lys Met Val Leu Thr Met Met Ser Gly Asp
65              70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
            245                 250                 255

Ile Phe Val Ile Cys Cys Leu Thr Tyr Cys Phe Ala Pro Arg Cys Arg
                260                 265                 270

Glu Arg Arg Arg Asn Glu Arg Leu Arg Arg Glu Ser Val Arg Pro Val
        275                 280                 285
```